United States Patent [19]

Mc Donald et al.

[11] Patent Number: 5,677,459

[45] Date of Patent: Oct. 14, 1997

[54] METHODS FOR THE PREPARATION OF MODULATORS OF ACETYLCHOLINE RECEPTORS

[75] Inventors: Ian A. Mc Donald; Jeffrey P. Whitten, both of San Diego; Nicholas D. Cosford, La Jolla, all of Calif.

[73] Assignee: Sibia Neurosciences, Inc., La Jolla, Calif.

[21] Appl. No.: 484,721

[22] Filed: Jun. 7, 1995

Related U.S. Application Data

[63] Continuation-in-part of Ser. No. 337,640, Nov. 10, 1994, Pat. No. 5,594,011.

[51] Int. Cl.$^6$ ............................................. C07D 401/04
[52] U.S. Cl. ............................................ 546/193; 546/276.4
[58] Field of Search ................................... 546/193, 276.4

[56] References Cited

U.S. PATENT DOCUMENTS

| | | | |
|---|---|---|---|
| 3,247,213 | 4/1966 | Büchel et al. | 514/340 |
| 4,155,909 | 5/1979 | Sanders et al. | 546/193 |
| 4,321,387 | 3/1982 | Chavdarian et al. | 546/281 |
| 4,965,074 | 10/1990 | Leeson | 424/449 |
| 5,248,690 | 9/1993 | Caldwel et al. | 514/343 |
| 5,278,176 | 1/1994 | Lin | 514/220 |
| 5,399,575 | 3/1995 | Friebe et al. | 514/408 |
| 5,418,229 | 5/1995 | Alker et al. | 514/220 |

FOREIGN PATENT DOCUMENTS

| | | |
|---|---|---|
| 0 537 993 A1 | 4/1993 | European Pat. Off. . |
| 0 567 251 A1 | 10/1993 | European Pat. Off. . |
| WO 92/15306 | 9/1992 | WIPO . |
| WO 92/21339 | 12/1992 | WIPO . |
| WO 94/05288 | 3/1994 | WIPO . |

OTHER PUBLICATIONS

Aislaitner et al., "The Synthesis Of 1'-N-Methyl-2'-Oxoanabasine, An Analogue Of Cotinine" *Bioorganic Med. Chem. Lett.* 4:515–520 (1994).

Albanese et al.,"Chronic Administration Of 1-Methyl-4-Phenyl-1,2,3,6-Tetrahydropyridine To Monkeys: Behavioural, Morphological And Biochemical Correlates" *Neuroscience* 55: 823–832 (1993).

Alkondon and Albuquerque, "Diversity of Nicotinic Acetylcholine Receptors in Rat Hippocampal Neurons. III. Agonist Actions of the Novel Alkaloid Epibatidine and Analysis of Type II Current" *J. Pharmacol. Exper. Therap.* 274:771–782 (1995).

Anderson et al., "Characterization of [$^3$H]ABT–418: A Novel Cholinergic Channel Ligand" *J. Pharmacol. Exper. Therap.* 273:1434–1441 (1995).

Arneric, Stephen P., "New Nicotinic Agonists And Cerebral Blood Flow" Abbott Laboratories, *Neuroscience* 386–394, 1991.

Aubert et al., "Comparative Alterations of Nicotinic and Muscarinic Binding Sites in Alzheimer's and Parkinson's Diseases" *J. Neurochem.* 58:529–541 (1992).

Brioni et al., "Nicotinic receptor agonists exhibit anxiolytic-like effects on the elevated plus-maze test" *Eur. J. Pharmacol.* 238:1–8 (1993).

Burk et al., "Catalytic Asymmetric Reductive Amination of Ketones via Highly Enantioselective Hydrogenation of the C=N Double Bond" *Tetrahedron* 50:4399–4428 (1994).

Burk et al., "Preparation and Use of C$_2$–Symmetric Bis-(phospholanes): Production of α–Amino Acid Derivatives via Highly Enantioselective Hydrogenation Reactions" *J. Am. Chem. Soc.* 115:10125 (1993).

Chaki et al., "Design and Syntheses of 4–Acylaminopyridine Derivatives: Novel High Affinity Choline Uptake Enhancers I" *Bioorgan. & Med. Chem. Let.* 5:1489–1494 (1995).

Chavdarian et al., "Synthesis of Optically Active Nicotinoids" *J. Org. Chem.* 47:1069–1073 (1982).

Cho and Chun, "Asymmetric Reduction of N–Substituted Ketimines with the Reagent prepared from Borane and (S)–(–)–2–Amino–3–methyl–1, 1–diphenylbutan–1–ol (Itsuno's Reagent): Enantioselective Synthesis of Optically Active Secondary Amines" *Chem. Soc. Perk.* 1:3200–3201 (1990).

Christensen et al., "On the Supersensitivity of Dopamine Receptors, Induced by Neuroleptics" *Psychoparmacol.* 48:1–6 (1976).

Clow et al., "Changes In Dopamine–Mediated Behaviour During One Year's Neuroliptic Administration" *Euro. J. Pharmacol.* 57:365–375 (1979).

(List continued on next page.)

*Primary Examiner*—Zinna Northington Davis
*Attorney, Agent, or Firm*—Gray Cary Ware & Freidenrich; Stephen E. Reiter

[57] ABSTRACT

In accordance with the present invention, there is provided a class of pyridine compounds which are modulators of acetylcholine receptors. The compounds of the invention displace acetylcholine receptor ligands from their binding sites. Invention compounds may act as agonists, partial agonists, antagonists or allosteric modulators of acetylcholine receptors, and are useful for a variety of therapeutic applications, such as the treatment of Alzheimer's disease and other disorders involving memory loss and/or dementia (including AIDS dementia); disorders of attention and focus (such as attention deficit disorder); disorders of extrapyramidal motor function such as Parkinson's disease, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulimia and anorexia; disorders of nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardia arrhythmias, comedication in surgical procedures, and the like.

27 Claims, No Drawings

OTHER PUBLICATIONS

Coyle et al., "Kainic Acid: Insights From a Neurotoxin into the Pathophysiology of Huntington's Disease" *Neurobehav. Toxicol. Tetatol.* 5:617–624 (1983).

Cushman and Castagnoli, Jr., "The Synthesis of trans-3'-Methylnicotine" *J. Org. Chem.* 37:1268–1271 (1972).

D'Amour and Smith, "A Method For Determining Loss Of Pain Sensation" *J. Pharmacol. Exp. Ther.* 72:74–79 (1941).

De Fiebre et al., "Characterization of a Series of Anabaseine–Derived Compounds Reveals That the 3–(4)–Dimethylaminocinnamylidine Derivative Is a Selective Agonist at Neuronal Nicotinic $\alpha 7/^{125}I-\alpha$–Bungarotoxin Receptor Subtypes" *Mol. Pharmacol.* 47:164–171 (1995).

Dwoskin et al., "Inhibition of [$^3$H]Dopamine Uptake Into Rat Striatal Slices By Quarternary N–Methylated Nicotine Metabolites" *Life Sciences* 50:PL–233 —PL–237 (1992).

Emerich et al., "Nicotine Potentiates Haloperidol–Induced Catalepsy and Locomotor Hypoactivity" *Pharmacol. Biochem. Behav.* 38: 875–880 (1991).

Estrella et al., "A further study of the neuromuscular effects of vesamicol (AH5183) and its enantiomer specificity" *Br. J. Pharmacol.* 93:759–768 (1988).

Flynn and Mash, "Characterization of L–[$^3$H]Nicotine Binding in Human Cerebral Cortex: Comparison Between Alzheimer's Disease and the Normal" *J. Neurochem.* 47:1948 (1986).

Haglid, F., "The Methylation of Nicotine with Methyl–lithium" *Acta Chem. Scand.* 21:329–334 (1967).

Hansson et al., "On the Quantitative Structure—Activity Relationships of Meta–Substituted (S)–Phenylpiperidines, a Class of Preferential Dopamine $D_2$ Autoreceptor Ligands: Modeling of Dopamine Synthesis and Release in Vivo by Means of Partial Least Squares Regression" *J. Med. Chem.* 38:3121–3131 (1995).

Hwang et al., "A Synthesis of $\alpha$–Substituted Amines" *J. Org. Chem.* 50:3885–3890 (1985).

Iwamoto, Edgar T., "Antinociception after Nicotine Administration into the Mesopontine Tegmentum of Rats: Evidence for Muscarinic Actions[1]" *J. Pharmacol. Exp. Ther.* 251:412–421 (1989).

Janson et al., "Differential effects of acute and chronic nicotine treatment on MPTP–(1–methyl–4–phenyl–1,2,3,6–tetrahydropyridine) induced degeneration of nigrostriatal dopamine neurons in the black mouse" *Clin. Investig.* 70:232–238 (1992).

Jacob III, Peyton, "Resolution of ($\pm$)–5–Bromonornicotine. Synthesis of (S)–Nornicotine of High Enantiomeric Purity" *J. Org. Chem.* 47:4165–4167 (1982).

Kashiwabara et al., "Comparative Vasodepressor Effects of 3–Pyridine Derivatives Possessing the Cyanoamidine or Amide Structure in Pithed Rats" *Arch. int. Pharmacodyn* 328:297–306 (1994).

Kawate et al., "Asymmetric Reduction of Imines with Chiral Dialkoxyboranes" *Tetrahedron Asym.* 3:227–230 (1992).

Kitamura et al., "General Asymmetric Synthesis of Isoquinoline Alkaloids. Enantioselective Hydrogenation of Enamides Catalyzed by BINAP–Ruthenium(II) Complexes" *J. Org. Chem.* 59:297–310 (1994).

Klockgether–and Turski, "NMDA Antagonists Potentiate Antiparkinsonian Actions of $_L$–Dopa in Monoamine–depleted Rats" *Ann. Neurol.* 28:539–546 (1990).

Lange et al., "Altered Muscarinic and Nicotinic Receptor Densities in Cortical and Subcortical Brain Regions in Parkinson's Disease" *J. Neurochem.* 60:197–203 (1993).

Leete et al., "Formation Of 5–Fluoronicotine From 5–Fluoronicotinic Acid In Nicotiana Tabacum" *Phytochem.* 10:2687–2692 (1971).

Lin et al., "Synthesis and Evaluation of Nicotine Analogs as Neuronal Nicotinic Acetylcholine Receptor Ligands" *J. Med. Chem.* 37:3542–3553 (1994).

Manescalchi et al., "Reductive Amination of 1,4–and 1,5–Dicarbonyl Compounds with (S)–Valine Methyl Ester. Synthesis of (S)–2–Phenylpyrrolidine and (S)–2–Phenylpiperidine." *Tetrahedron Letters* 35:2775–2778 (1994).

Mathre et al., "A Practical Process for the Preparation of Tetrahydro–1–methyl–3,3–diphenyl–1H,3H–pyrrolo [1,2–c]–[1,3,2]oxazaborole—Borane. A Highly Enantioselective Stoichiometric and Catalytic Reducing Agent" *J. Org. Chem.* 58:2880–2888 (1993).

Miyata et al., "Role of the Serotonin$_3$ Receptor in Stress-–Induced Defecation" *J. Pharmacol. Exp. Ther.* 261:297–303 (1992).

Natsugari et al., "Novel, Potent, and Orally Active Substance P Antagonists: Synthesis and Antagonist Activity of N–Benzylcarboxamide Derivatives of pyrido [3,4–b]pyridine" 38: 3106–3120 (1995).

Nilsson and Hallberg, "Regioselective Palladium–Catalyzed Tandem $\alpha$–Arylation/Isomerization of Cyclic Enamides" *J. Org. Chem.* 55:2464–2470 (1990).

O'Neill et al., "Evidence for an involvement of D1 and D2 dopamine receptors in mediating nicotine–induced hyeractivty in rats" *Psychopharmacology* 104: 343–350 (1991).

Ozawa et al., "Palladium–Catalyzed Asymmetric Alkenylation of Cyclic Olefins" *Tetrahedron Letters* 34:2505–2508 (1993).

Pellow et al., "Validation of open: closed arm entries in an elevated plus–maze as a measure of anxiety in the rat" *Neurosci. Meth.* 14:149–167 (1985).

Rondahl, Lars, "Synthetic analogues of nicotine VI Nicotine substituted in the 5–position" *Acta Pharma. Suecica* 14:113–118 (1977).

Rueppel and Rapoport, "Aberrant Alkaloid Biosysthese. Formation of Nicotine Analogs from Unnatural Precursors in *Nicotiana glutinosa*" *J. Am. Chem. Soc.* 93:7021–7028 (1971).

Rupniak et al., "Cholinergic Manipulation of Perioral Behaviour Induced by Chronic Neuroleptic Administration to Rats" *Psychopharmacol.* 79:226–230 (1983).

Sacaan et al., "Metabotropic Glutamate Receptor Activation Produces Extrapyramidal Motor System Activation That Is Mediated by Striatal Dopamine" *J. Neurochem.* 59:245 (1992).

Scharcz et al., "Quinolinic Acid: An Endogenous Metabolite That Produces Axon–Sparing Lesions in Rat Brain" *Science* 219:316–318 (1983).

Sershen et al., "Behavioral and Biochemical Effects of Nicotine in an MPTP–Induced Mouse Model of Parkinson's Disease" *Pharmacol. Biochem. Behav.* 28:299–303 (1987).

Shibagaki et al., "The Syntheses Of 4–Aminonicotine And 4–Aminocotinine" *Heterocycles* 23:1681–1684 (1985).

Sundstrom et al., "Chronic neurochemical and behavioral changes in MPTP–lesioned C57BL/6 mice: a model for Parkinson's disease" *Brain Res.* 528:181–188 (1990).

Ungerstedt and Arbuthknott, "Quantitative Recording of Rotational Behavior In Rats After 6–Hydroxy–Dopamine Lesions Of The Nigrostriatal Dopamine System" *Brain Res.* 24:485–493 (1970).

Ungerstedt et al., "Animal Models of Parkinsonism" *Adv. Neurol.* 3:257–271 (1973).

Von Voigtlander and Moore, "Turning Behavior Of Mice With Unilateral 6–Hydroxydopamine Lesions In The Striatum: Effects Of Apomorphine, $_L$–Dopa, Amantadine, Amphetamine And Other Psychomotor Stimulants" *Neuropharmacology* 12:451–462 (1973).

Waddington et al., "Spontaneous Orofacial Dyskinesia and Dopaminergic Function in Rats After 6 Months of Neuropeptic Treatment" *Science* 220:530–532 (1983).

Whitehouse et al., "Reductions in [$^3$H]nicotinic acetylcholine binding in Alzheimer's disease and Parkinson's desease: An autoradiographic study" *Neurology* 38:720–723 (1988).

Williams et al., "Neuronal Nicotinic Acetylcholine Receptors" *Drug News & Perspectives* 7(4):205–223 (1994).

Williams et al., "Stress–Induced Changes in Intestinal Transit in the Rat: A Model for Irritable Bowel Syndrome" *Gastroenterology* 94:611–621 (1988).

Willoughby and Buchwald, "Synthesis of Highly Enantiomerically Enriched Cyclic Amines by the Catalytic Asymmetric Hydrogenation of Cyclic Imines" *J. Org. Chem.* 58:7627–7629 (1993).

Willoughby and Buchwald, "Asymmetric Titanocene–Catalyzed Hydrogenation of Imines" *J. Am. Chem. Soc.* 114:7562–7564 (1992).

Wonnacott, S., "Neuronal nicotinic receptors: functional correlates of ligand binding sites" *Biochem. Soc. Trans.* 19:121–124 (1991).

Yamada et al., "Asymmetric Reduction of Cyclic Imines with Chiral Sodium Acyloxyborohydrides" *J. Chem. Soc., Perk.* 1:265–270 (1983).

Yamada et al., "Effects of a thienylalkylamine derivative, T–1815, on colonic propulsion in mice and rats" *Jpn. J. Pharmacol.* 58(Suppl.):131 (1992).

Zoltewicz at al., "Hydrolysis of Cholinergic Anabaseine and N–Methylanabaseine: Influence of Cosolvents on the Position of the Ring–Chain Equilibrium—Compensatory Changes" *Bioorganic Chem.* 18:395–412 (1990).

METHODS FOR THE PREPARATION OF MODULATORS OF ACETYLCHOLINE RECEPTORS

RELATED APPLICATIONS

This application is a continuation-in-part of U.S. Ser. No. 08/337,640, filed Nov. 10, 1994, now U.S. Pat. No. 5,594,011, the entire contents of which are hereby incorporated by reference herein.

FIELD OF THE INVENTION

The present invention relates to novel compounds which are capable of modulating acetylcholine receptors. Invention compounds are useful, for example, for treatment of dysfunction of the central or autonomic nervous systems including dementia, cognitive disorders, neurodegenerative disorders, extrapyramidal disorders, convulsive disorders, cardiovascular disorders, endocrine disorders, pain, gastrointestinal disorders, eating disorders, affective disorders, and drug abuse. In addition, the present invention relates to pharmaceutical compositions containing these compounds, as well as various uses therefor.

BACKGROUND OF THE INVENTION

By modulation of neurotransmitter release (including dopamine, norepinephrine, acetylcholine and serotonin) from different brain regions, acetylcholine receptors are involved in the modulation of neuroendocrine function, respiration, mood, motor control and function, focus and attention, concentration, memory and cognition, and the mechanisms of substance abuse. Ligands for acetylcholine receptors have been demonstrated to have effects on attention, cognition, appetite, substance abuse, memory, extrapyramidal function, cardiovascular function, pain and gastrointestinal motility and function. The distribution of acetylcholine receptors that bind nicotine, i.e., nicotinic acetylcholine receptors, is widespread in the brain, including the basal ganglia, limbic system, cerebral cortex and mid- and hind-brain nuclei. In the periphery, the distribution includes muscle, autonomic ganglia, the gastrointestinal tract and the cardiovascular system.

Acetylcholine receptors have been shown to be decreased, inter alia, in the brains of patients suffering from Alzheimer's disease or Parkinson's disease, diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. Thus, there is a continuing need for compounds which can selectively modulate the activity of acetylcholine receptors. In response to such need, the present invention provides a new family of compounds which modulate acetylcholine receptors.

BRIEF DESCRIPTION OF THE INVENTION

In accordance with the present invention, we have discovered that the class of pyridine compounds defined herein are modulators of acetylcholine receptors.

The compounds of the present invention are capable of displacing one or more acetylcholine receptor ligands, e.g., $^3$H-nicotine, from mammalian cerebral membrane binding sites. Invention compounds may act as agonists, partial agonists, antagonists or allosteric modulators of acetylcholine receptors. Therapeutic indications for compounds with activity at acetylcholine receptors include diseases of the central nervous system such as Alzheimer's disease and other disorders involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulemia and anorexia; disorders of nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardia arrhythmias, as well as co-medication uses in surgical applications.

DETAILED DESCRIPTION OF THE INVENTION

In accordance with the present invention, there are provided compounds having the structure (Formula I):

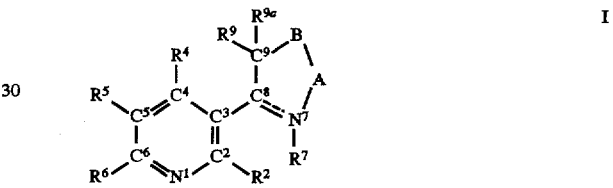

wherein:

A is a 1, 2 or 3 atom bridging species which forms part of a saturated or monounsaturated 5-, 6- or 7-membered ring including $N^7$, $C^8$, $C^9$ and B;

B is selected from —O—, —S—, —$NR^{10}$—, wherein $R^{10}$ is selected from hydrogen, lower alkyl, aryl, substituted aryl, alkylaryl, substituted alkylaryl, arylalkyl, substituted arylalkyl; —$C^{10}HR^{10a}$—, wherein $R^{10a}$ is selected from hydrogen, lower alkyl, hydroxyalkyl, aryl, aryloxyalkyl, fluoro, trifluoromethyl, cyano, cyanomethyl, —OR', —$NR'_2$, or —SR', wherein each R' is independently hydrogen, lower alkyl, alkenyl, alkynyl or aryl, provided, however, that neither the —$NR'_2$ nor the —SR' functionality is conjugated with an alkenyl or alkynyl functionality; or B is =$C^{10}R^{10a}$— or =N—, provided there is no double bond in the ring between A and B, or between B and $C^9$ when there is a double bond between $N^7$ and $C^8$, and provided that B is not a heteroatom when A is a 1 atom bridging species;

$R^2$, $R^4$, $R^5$ and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is —S(O)$_2$NHR', R' is not alkenyl or alkynyl;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''$_2$, wherein each R''' is independently as defined above, or each R''' and the N to which they are attached can cooperate to form a 4-, 5-, 6- or 7-membered ring; provided, however, that the —NR'''$_2$ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR''''$_3$, wherein R'''' is selected from alkyl or aryl;

$R^7$ is selected from hydrogen, lower alkyl, aryl, substituted aryl, alkylaryl, or substituted alkylaryl, or $R^7$ is absent when there is a double bond between $N^7$ and $C^8$; and $R^9$ and $R^{9a}$ are each independently selected from hydrogen, lower alkyl, hydroxyalkyl, aryl, aryloxyalkyl, fluoro, trifluoromethyl, cyano, cyanomethyl, —OR', —NR'$_2$, or —SR', wherein each R' is as defined above, provided, however, that neither the —NR'$_2$ nor the —SR' functionality is conjugated with an alkenyl or alkynyl functionality.

Specifically excluded from the above definition of compounds embraced by Formula I are nicotine (i.e., wherein A=—CH$_2$—, B=—CH$_2$—, $R^2$, $R^4$, $R^5$, $R^6$, $R^9$ and $R^{9a}$=H and $R^7$=methyl); nornicotine (i.e., wherein A=—CH$_2$—, B=—CH$_2$—, and $R^2$, $R^4$, $R^5$, $R^6$, $R^7$, $R^9$ and $R^{9a}$ are each H; anabasine and N-methyl anabasine (i.e., wherein A=—CH$_2$CH$_2$—, B=—CH$_2$—, $R^2$, $R^4$, $R^5$, $R^6$, $R^9$ and $R^{9a}$=H, and $R^7$=H or methyl, respectively); anahaseine (i.e., wherein A=—CH$_2$CH$_2$—, B=—CH$_2$—, $R^2$, $R^4$, $R^5$, $R^6$, $R^9$ and $R^{9a}$ are hydrogen and $R^7$ is absent, due to the presence of a double bond between $N^7$ and $C^8$); anatahine (i.e., wherein A=—CH$_2$CH=, B=—CH=, and each of $R^2$, $R^4$, $R^5$, $R^6$, $R^7$, $R^9$ and $R^{9a}$ are hydrogen); N-methyl-2-oxoanabasine (i.e., wherein A=—C(O)CH$_2$—, B=—CH$_2$—, $R^2$, $R^4$, $R^5$, $R^6$, $R^9$ and $R^{9a}$ are hydrogen and $R^7$=methyl); myosmine (i.e., wherein A=—CH$_2$—, B=—CH$_2$—, $R^2$, $R^4$, $R^5$, $R^6$, $R^9$ and $R^{9a}$ are hydrogen, and $R^7$ is absent, due to the presence of a double bond between $N^7$ and $C^8$); cotinine (i.e., wherein A=—C(O)—, B=—CH$_2$—, $R^2$, $R^4$, $R^5$, $R^6$, $R^9$ and $R^{9a}$=H, and $R^7$=methyl); as well as the compounds wherein A=—CH$_2$—, B=—CH$_2$—, $R^2$=H or Br, $R^4$, $R^6$, $R^9$ and $R^{9a}$=H, $R^5$=H or methyl, and $R^7$=methyl; compounds wherein A=—CH$_2$—, B=—CH$_2$—, $R^2$, $R^4$, $R^5$ and $R^6$=H or alkyl, $R^7$ is alkyl and $R^9$ and $R^{9a}$=hydrogen; compounds wherein A=—CH$_2$—, —C(O)— or —CH(CH$_2$F)—, B=—CHR$^{10a}$— (wherein $R^{10a}$ is H, lower alkyl, hydroxyalkyl, F, cyano, cyanomethyl or —OR', wherein R'=hydrogen or methyl), $R^2$, $R^4$, $R^5$ and $R^6$=H, $R^7$ is methyl and $R^9$ and $R^{9a}$=hydrogen, methyl, fluorine, cyanomethyl, cyano or hydroxyalkyl; compounds wherein A=—CH$_2$—, —CH$_2$CH$_2$— or —CH$_2$CH=, B=—CH$_2$— or —CH=, $R^2$ and $R^6$=lower alkyl or arylalkyl, $R^4$, $R^5$, $R^9$ and $R^{9a}$=H and $R^7$=hydrogen or methyl; compounds wherein A=—CH$_2$—, B=—CH$_2$—, $R^2$, $R^4$, $R^5$ and $R^6$=H, $R^7$ and $R^9$ are methyl and $R^{9a}$=hydrogen or methyl; compounds wherein A=—CH$_2$—, B=—CH$_2$—, $R^2$, $R^4$ and $R^6$=H or methyl, $R^5$, $R^9$ and $R^{9a}$ are hydrogen, and $R^7$=methyl; compounds wherein A=—CH$_2$— or —C(O)—, B=—CH$_2$—, $R^2$, $R^5$, $R^6$, $R^9$ and $R^{9a}$ are hydrogen, $R^4$=—NH$_2$ and $R^7$=methyl; compounds wherein A=—CH$_2$—, B=—CH$_2$—, $R^2$, $R^4$, $R^6$, $R^7$, $R^9$ and $R^{9a}$ are hydrogen and $R^5$=bromine; compounds wherein A=—CH$_2$—, B=—CH$_2$—, $R^2$, $R^4$, $R^6$, $R^9$ and $R^{9a}$ are hydrogen, $R^5$=fluorine, chlorine, bromine, iodine, or —NH$_2$, and $R^7$=hydrogen or methyl; compounds wherein A=—CH$_2$— or —CH$_2$CH$_2$—, B=—CH$_2$—, $R^2$, $R^4$, $R^5$ and $R^6$ are alkyl or halogen, $R^7$=H or alkyl, and $R^9$ and $R^{9a}$ are alkyl; compounds wherein A=—CH$_2$CH$_2$—, B=—CH$_2$—, $R^2$, $R^4$, $R^5$ and $R^6$ are H or lower alkyl, $R^7$=absent or H if the pyrrolidone ring contains no unsaturation, and $R^9$ and $R^{9a}$ are H or lower alkyl.

As employed herein, "lower alkyl" refers to straight or branched chain alkyl radicals having in the range of about 1 up to 4 carbon atoms; "alkyl" refers to straight or branched chain alkyl radicals having in the range of about 1 up to 12 carbon atoms; "substituted alkyl" refers to alkyl radicals further bearing one or more substituents such as aryl, heterocyclic, hydroxy, alkoxy (of a lower alkyl group), mercapto (of a lower alkyl group), aryloxy, halogen, trifluoromethyl, cyano, nitro, as well as:

—S(O)R', —S(O)R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is —S(O)$_2$NHR', R' is not alkenyl or alkynyl;

—C(O)R'', wherein R'' is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''$_2$, wherein each R''' is independently as defined above, or each R''' and the N to which they are attached can cooperate to form a 4-, 5-, 6- or 7-membered ring; provided, however, that the —NR'''$_2$ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR'''₃, wherein R''' is selected from alkyl or aryl; and the like;

"cycloalkyl" refers to cyclic ring-containing radicals containing in the range of about 3 up to 8 carbon atoms, and "substituted cycloalkyl" refers to cycloalkyl radicals further bearing one or more substituents as set forth above;

"alkenyl" refers to straight or branched chain hydrocarbyl radicals having at least one carbon—carbon double bond, and having in the range of about 2 up to 12 carbon atoms and "substituted alkenyl" refers to alkenyl radicals further bearing one or more substituents as set forth above;

"alkynyl" refers to straight or branched chain hydrocarbyl radicals having at least one carbon—carbon triple bond, and having in the range of about 2 up to 12 carbon atoms, and "substituted alkynyl" refers to alkynyl radicals further bearing one or more substituents as set forth above;

"aryl" refers to aromatic radicals having in the range of 6 up to 14 carbon atoms and "substituted aryl" refers to aryl radicals further bearing one or more substituents as set forth above;

"alkylaryl" refers to alkyl-substituted aryl radicals and "substituted alkylaryl" refers to alkylaryl radicals further bearing one or more substituents as set forth above;

"arylalkyl" refers to aryl-substituted alkyl radicals and "substituted arylalkyl" refers to arylalkyl radicals further bearing one or more substituents as set forth above;

"arylalkenyl" refers to aryl-substituted alkenyl radicals and "substituted arylalkenyl" refers to arylalkenyl radicals further bearing one or more substituents as set forth above;

"arylalkynyl" refers to aryl-substituted alkynyl radicals and "substituted arylalkynyl" refers to arylalkynyl radicals further bearing one or more substituents as set forth above;

"aroyl" refers to aryl-carbonyl species such as benzoyl and "substituted aroyl" refers to aroyl radicals further bearing one or more substituents as set forth above;

"heterocyclic" refers to cyclic (i.e., ring-containing) radicals containing one or more heteroatoms (e.g., N, O, S, or the like) as part of the ring structure, and having in the range of 3 up to 14 carbon atoms and "substituted heterocyclic" refers to heterocyclic radicals further bearing one or more substituents as set forth above;

"acyl" refers to alkyl-carbonyl species; and

"halogen" refers to fluoride, chloride, bromide or iodide radicals.

In one aspect of the present invention, bridging group A is a 1, 2 or 3 atom bridging species selected from alkylene, or —O—, —C(O)—, —N(R¹¹)—, and/or —S-containing alkylene moiety, wherein R¹¹ is hydrogen or a lower alkyl moiety; provided however that the ring formed by N⁷, C⁸, C⁹, A and B does not contain any covalent heteroatom— heteroatom single bonds, or any heteroatom-methylene-heteroatom bonding relationships. Thus, A can be selected, for example, from —CH₂—, —CH₂CH₂—, —CH₂CH₂CH₂—, —C(O)—, —C(O)—CH₂—, —C(O)—CH₂CH₂—, and the like. Presently preferred compounds of the invention are those wherein A is selected from —CH₂—, —CH₂CH₂— or —C(O)—, with compounds having A as —CH₂— being the presently most preferred.

In accordance with another aspect of the present invention, bridging group B is selected from —O—, —S—, —NR¹⁰—, wherein R¹⁰ is selected from hydrogen, lower alkyl, aryl, substituted aryl, alkylaryl, substituted alkylaryl, arylalkyl, substituted arylalkyl; —C¹⁰HR¹⁰ᵃ—, wherein R¹⁰ᵃ is selected from hydrogen, lower alkyl, hydroxyalkyl, aryl, aryloxyalkyl, fluoro, trifluoromethyl, cyano, cyanomethyl, —OR', —NR'₂, or —SR', wherein each R' is independently hydrogen, lower alkyl, alkenyl, alkynyl or aryl, provided, however, that neither the —NR'₂ nor the —SR' functionality is conjugated with an alkenyl or alkynyl functionality; or B is =C¹⁰R¹⁰ᵃ— or =N—, provided there is no double bond in the ring between A and B, or between B and C⁹ when there is a double bond between N⁷ and C⁸, and provided that B is not a heteroatom when A is a one-atom bridging species. Thus, B can be selected, for example, from —CH₂—, —O—, —N(R¹⁰)—, —S—, and the like. Presently preferred compounds of the invention are those wherein B is —CH₂—.

In accordance with yet another aspect of the present invention, R⁵ is alkynyl or substituted alkynyl having the structure:

wherein R⁵' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, halogen, cyano, nitro;

—S(O)R', —S(O)₂R' or —S(O)₂NHR', wherein each R' is as defined above, provided, however, that when R², R⁴, R⁵ or R⁶ is —S(O)R', R' is not hydrogen, alkenyl or alkynyl, and provided that when R², R⁴, R⁵ or R⁶ is —S(O)₂NHR', R' is not alkenyl or alkynyl;

—C(O)R'', wherein R'' is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''₂, wherein each R''' is independently as defined above, or each R''' and the N to which they are attached can cooperate to form a 4-, 5-, 6- or 7-membered ring; provided, however, that the —NR'''₂ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR''''₃, wherein R'''' is selected from alkyl or aryl, and the like.

In addition, R⁵' can also be alkylene, substituted alkylene, arylene, substituted arylene, and the like, so that the resulting compound is a polyfunctional species, bearing two or more of the substituted pyridyl structures contemplated by structure I. Thus, R⁵ serves as a bridge or linking moiety to couple two or more of the substituted pyridyl structures contemplated by structure I in a single compound.

Presently preferred $R^{5'}$ groups include hydrogen, methyl, ethyl, propyl, hydroxymethyl, 1-hydroxyethyl, 2-hydroxyethyl, methoxymethyl, 2-hydroxy-2-isopropyl, dimethylaminomethyl, phenyl, and the like.

Additional preferred compounds of the invention are those wherein $R^2$ is selected from hydrogen or amino; wherein $R^4$ is hydrogen, aryl, alkoxy or aryloxy; wherein $R^5$ is selected from aryl, substituted aryl (wherein substituents on the aryl ring are independently selected from one or more of bromine, chlorine, fluorine, phenyl, methoxy, hydroxy, mercaptomethyl and trifluoromethyl substituents being especially preferred), trialkylsilyl, arylalkyl, arylalkenyl or arylalkynyl; wherein $R^6$ is selected from hydrogen, chlorine, amino, alkyl or alkoxy (with hydrogen, methyl or methoxy being especially preferred); wherein $R^7$ is absent or selected from hydrogen or methyl; and wherein $R^9$ and $R^{9a}$ are each independently selected from hydrogen, lower alkyl, alkoxy or aryloxy.

Particularly preferred compounds of the invention include the compound wherein A=—$CH_2$— or —$CH_2CH_2$—, B=—$CH_2$—, $R^2$=H, $R^4$=H, $R^5$ is selected from ethynyl, methylethynyl, ethylethynyl, propylethynyl, hydroxymethylethynyl, 1-hydroxyethylethynyl, 2-hydroxyethylethynyl, methoxymethylethynyl, 2-hydroxy-2-propylethynyl, dimethylaminomethylethynyl, 3-chloro-4-hydroxyphenyl, 3-chlorophenyl, 3-fluoro-4-methoxyphenyl, 4-hydroxyphenyl, 4-biphenyl, phenylethynyl, 4-methoxyphenyl, 4-fluorophenyl, 3-fluoro-4-hydroxyphenyl, 4-methylphenyl, 3-chloro-4-methoxyphenyl, 4-aminophenyl, 4-acetamidophenyl, 4-acetoxyphenyl, 3-chloro-4-acetoxyphenyl, 3-chloro-4-acetamidophenyl, 4-methanesulfonanilido, or 3-chloro-4-methanesulfonanilido, $R^6$=H, $R^7$=H, methyl, or $R^7$ is absent when there is a double bond between $N^7$ and $C^8$, $R^9$=H, and $R^{9a}$=H.

Invention compounds have affinity for acetylcholine receptors. As employed herein, the term "acetylcholine receptor" refers to both nicotinic and muscarinic acetylcholine receptors. Affinity of invention compounds for such receptors can be demonstrated in a variety of ways, e.g., via competitive radioligand binding experiments in which the test compounds displace isotopically labelled ligands (such as nicotine, cytisine, methylcarbamylcholine, quinuclidinyl benzilate, and the like) from binding sites in mammalian cerebral membranes. Furthermore, the binding of compounds to acetylcholine receptors can be evaluated as a functional response. For example, the activity of invention compounds can be evaluated employing functional assays based on recombinant neuronal acetylcholine receptor expression systems (see, for example, Williams et al., *Drug News & Perspectives* 7:205–223 (1994)). Test compounds can also be evaluated for their ability to modulate the release of neurotransmitters (e.g., dopamine, norepinephrine, and the like) from rat brain slices (e.g., striatum, hippocampus, and the like). See Examples 24 and 25 for further detail on such techniques. Moreover, test compounds can also be evaluated by way of behavioral studies employing animal models of various CNS, autonomic and cardiovascular disorders (see, for example, D'Amour and Smith, *J. Pharmacol. Exp. Ther.* 72:74–79 (1941) and Iwamoto, *J. Pharmacol. Exp. Ther.* 251:412–421 (1989) for animal models of pain; Klockgether and Turski, *Ann. Neurol.* 28:539–546 (1990), Colpaert, F., *Neuropharmacology* 26:1431–1440 (1987), Ungerstedt and Arbuthknott, *Brain Res.* 24:485–493 (1970), Von Voigtlander and Moore, *Neuropharmacology* 12:451–462 (1973), Ungerstedt et al., *Adv. Neurol.* 3:257–279 (1973), Albanese et al., *Neuroscience* 55:823–832 (1993), Janson et al., *Clin. Investig.* 70:232–238 (1992), Sundstrom et al., *Brain Res.* 528:181–188 (1990), Sershen et al., *Pharmacol. Biochem. Behav.* 28:299–303 (1987) for animal models of Parkinson's disease; Williams et al., *Gastroenterology* 94:611–621 (1988), Miyata et al., *J. Pharmacol. Exp. Ther.* 261:297–303 (1992), Yamada et al., *Jpn. J. Pharmacol.* 58 (Suppl.):131 (1992) for animal models of irritable bowel syndrome; Coyle et al., *Neurobehav. Toxicol. Tetatol.* 5:617–624 (1983), Schartz et al., *Science* 219:316–318 (1983) for animal models of Huntington's disease; Clow et al., *Euro. J. Pharmacol.* 57:365–375 (1979), Christensen et al., *Psychoparmacol.* 48:1–6 (1976), Rupniak et al., *Psychopharmacol.* 79:226–230 (1983), Waddington et al., *Science* 220:530–532 (1983) for animal models of tardive dyskinesia; Emerich et al., *Pharmacol. Biochem. Behav.* 38:875–880 (1991) for animal models of Gilles de la Tourette's syndrome; Brioni et al., *Eur. J. Pharmacol.* 238:1–8 (1993), Pellow et al., *J. Neurosci. Meth.* 14:149 (1985) for animal models of anxiety; and Estrella et al., *Br. J. Pharmacol* 93:759–768 (1988) for the rat phrenic nerve model which indicates whether a compound has muscle effects that may be useful in treating neuromuscular disorders).

Those of skill in the art recognize that invention compounds typically contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

In accordance with still another embodiment of the present invention, there are provided methods for the preparation of pyridine compounds as described above. For example, many of the pyridine compounds described above can be prepared using synthetic chemistry techniques well known in the art from the acyl pyridine precursor of Formula II as outlined in Scheme I.

Scheme I

Step A

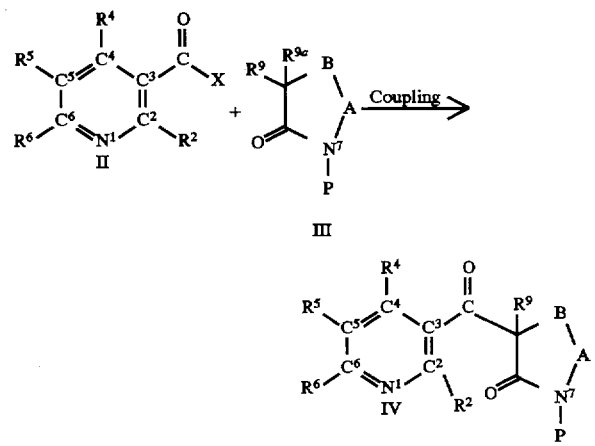

-continued
Scheme I

Step B

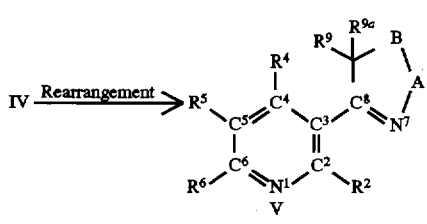

Step C

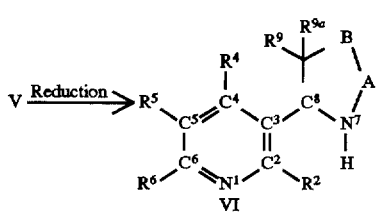

Step D

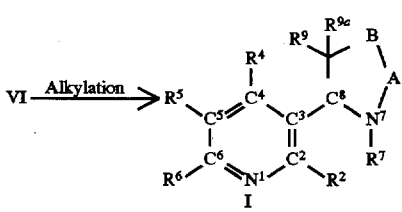

In the above scheme, $R^2$, $R^4$, $R^5$, $R^6$, $R^7$, $R^9$, $R^{9a}$, A and B are as defined above, P is a nitrogen protecting group, and X is a carboxylic acid activating group. Nitrogen protecting groups contemplated for use herein are functional groups which are stable under basic conditions, but which are readily removed under acidic conditions. Examples of suitable protecting groups include vinyl groups, tert-butylcarbonyl groups, benzyloxycarbonyl groups, formyl groups, and the like. Carboxylic acid activating groups, X, contemplated for use herein can be readily identified by those of skill in the art, and include esters, acid chlorides, mixed anhydrides, the Weinreb amide, and the like.

In step A of Scheme I, acyl pyridine of Formula II is coupled in the presence of strong base with a lactam of Formula III to produce a pyridoyllactam of Formula IV. The choice of base for use in this coupling reaction depends, at least in part, on the acidity of the hydrogen atoms adjacent to the carbonyl group of compound III. In general, strong bases such as sodium hydride, sodamide, lithium diisopropylamide, lithium hexamethyldisilazide, and the like, are used. The presently preferred base for use in the practice of the present invention is lithium hexamethyldisilazide.

The above-described coupling reaction is typically carried out in aprotic solvent, such as, for example, tetrahydrofuran (THF), diethyl ether, tert-butyl methyl ether, 1,2-dimethoxyethane, toluene, and the like. Presently preferred solvents for use in the practice of the present invention are THF and tert-butyl methyl ether. The coupling reaction can be carried out over a wide range of temperatures. Typically reaction temperatures fall in the range of about −78° C. up to reflux. Temperatures in the range of about −78° C. up to ambient are presently preferred. Reaction times required to effect the desired coupling reaction can vary widely, typically falling in the range of about 15 minutes up to about 24 hours. Preferred reaction times fall in the range of about 4 up to 12 hours. It is not necessary to purify the product of the above-described coupling reaction (i.e., compound of Formula IV), and the resulting reaction product is typically subjected directly to the rearrangement step described below as step B.

In Step B of Scheme I, pyridoyllactam of Formula IV is rearranged to produce the cyclic imine V. Concomitantly with this rearrangement, protective group P is removed (although, if desired, the protecting group can be selectively removed from compound IV prior to the rearrangement). The desired rearrangement is typically effected by contacting pyridoyllactam with aqueous media containing strong acid (e.g., hydrochloric acid, hydrobromic acid, sulfuric acid, trifluoroacetic acid, and the like) under reflux conditions. Presently preferred media for the above-described rearrangement reaction is 19% aqueous hydrochloric acid. The desired rearrangement reaction is typically complete within about 1 up to 24 hours, with 4 up to 12 hours generally being sufficient.

Cyclic imine of Formula V can then be recovered from the reaction media by basification, followed by extraction, filtration, and the like. Purification can be achieved by a variety of techniques, such as, for example, chromatography, recrystallization, and the like.

Conversion of cyclic imine V into compounds of the invention (as defined by structure I) can be accomplished employing numerous synthetic procedures, such as, for example, the procedures set forth is steps C and D of Scheme I. Thus, as shown in Step C, cyclic imine V is converted into cyclic amine VI by reduction of the imine. This reduction reaction can be promoted, for example, by hydride addition, employing a suitable hydride source (e.g., sodium borohydride, sodium cyanoborohydride, lithium aluminum hydride, sodium triacetoxyborohydride, lithium tri-tert-butoxy aluminum hydride, sodium trimethoxyborohydride, diisobutylaluminum hydride, formic acid, and the like) or by contacting the imine with hydrogen in the presence of a transition metal catalyst (such as, for example, palladium on carbon, Raney Nickel, platinum oxide, tris (triphenylphosphine)rhodium (I) chloride (i.e., Wilkinson's catalyst), palladium hydroxide, and the like). Presently preferred reducing conditions comprise treating imine V with sodium borohydride in a solvent mixture such as methanol/acetic acid, at a reaction temperature in the range of about −60° C. up to about ambient temperature, for in the range of about 1 up to 24 hours. As recognized by those of skill in the art, the selection of reducing agent, reaction time, reaction temperature and reaction media will depend on the specific compound having the Formula V which is being treated.

Cyclic amine VI can be isolated from the reaction mixture employing standard separation techniques which are well known to those of skill in the art. Similarly, purification of amine can be achieved employing standard purification techniques, such as, for example, chromatography, recrystallization, distillation, and the like. If desired, cyclic amine VI can be further converted into an acid addition salt.

Since cyclic amine VI has a center of asymmetry, reagents for the above-described reduction reaction can be chosen so as to promote selective reduction to produce amine VI which is substantially enriched in one of the possible enantiomers. In some instances, by judicious choice of reducing agents, each of the possible enantiomers can be prepared in high optical purity. For example, chiral borohydride reducing agents can be employed, as described, for example, by Yamada et al. in *J. Chem. Soc., Perk.* 1 265 (1983), Kawate et al., in *Tetrahedron Asym.* 3, 227 (1992), Mathre et al., *J. Org. Chem.* 58:2880 (1993), or Cho and Chun in *J. Chem. Soc. Perk.* 1 3200 (1990). Alternatively, catalytic hydrogenation in the presence of chiral catalyst can be employed, as described, for example, by Kitamura et al., in *J. Org. Chem.* 59:297 (1994), Burk et al., in *Tetrahedron* 50:4399 (1994), Burk et al, in *J. Am. Chem. Soc.* 115:10125 (1993), Willoughby and Buchwald in *J. Org. Chem.* 58:7627 (1993), or Willoughby and Buchwald in *J. Am. Chem. Soc.* 114:7562 (1992). As yet another alternative, optically pure enantiomers of compounds of Formula I can be prepared by resolution of a mixture of enantiomers by selective crystallization of a single enantiomer in the presence of an optically pure acid addition salt. Such methods are well known in the art, such as, for example, the preparation of optically pure addition salts with each isomer of tartaric acid, tartaric acid derivatives (e.g., D- or L-dibenzoyl and di-p-tolyltartaric acid, and the like. Another method which is widely used in the art involves the preparation of diastereomeric derivatives of racemic amines (e.g., α-methoxy-α-(trifluoromethyl) phenylacetic acid (i.e., Mosher's acid) amide derivatives). The resulting diastereomeric derivatives can then be separated by well known techniques, such as chromatography.

The separation of the respective enantiomers of a racemic mixture can be accomplished employing chromatographic techniques which utilize a chiral stationary phase. Examples include chiral gas chromatography (chiral GC), chiral medium performance liquid chromatography (chiral MPLC), chiral high performance liquid chromatography (chiral HPLC), and the like.

For compounds of Formula I, where $R^7$ is not hydrogen, alkylation step D of Scheme I is carried out. Those of skill in the art can readily identify suitable N-alkylation reactions suitable for such purpose. For example, cyclic amine of Formula VI can be contacted with an aldehyde (e.g., formaldehyde, acetaldehyde, benzaldehyde, and the like) in the presence of a suitable reducing agent (such as the reducing agents described above with reference to Step C).

The substituted amines of Formula I produced by the above-described alkylation/reduction reaction can be isolated and purified employing standard methods which are well known in the art (e.g., extraction, chromatography, and the like). A presently preferred technique for recovery of reaction product is extraction of amine I from basified reaction medium with dichloromethane. Alternatively, crude amine can be converted into an acid addition salt (e.g., hydrochloride, hydrobromide, fumarate, tartrate, and the like), then purified by recrystallization.

Where $R^7$ of Formula I is a methyl group, it is possible to carry out the steps set forth in Scheme I wherein protecting group P is methyl (see, for example, Spath & Bretschneider in *Chem. Ber.* 61:327 (1928)).

Another method for the preparation of compounds of Formula I is depicted in Scheme II.

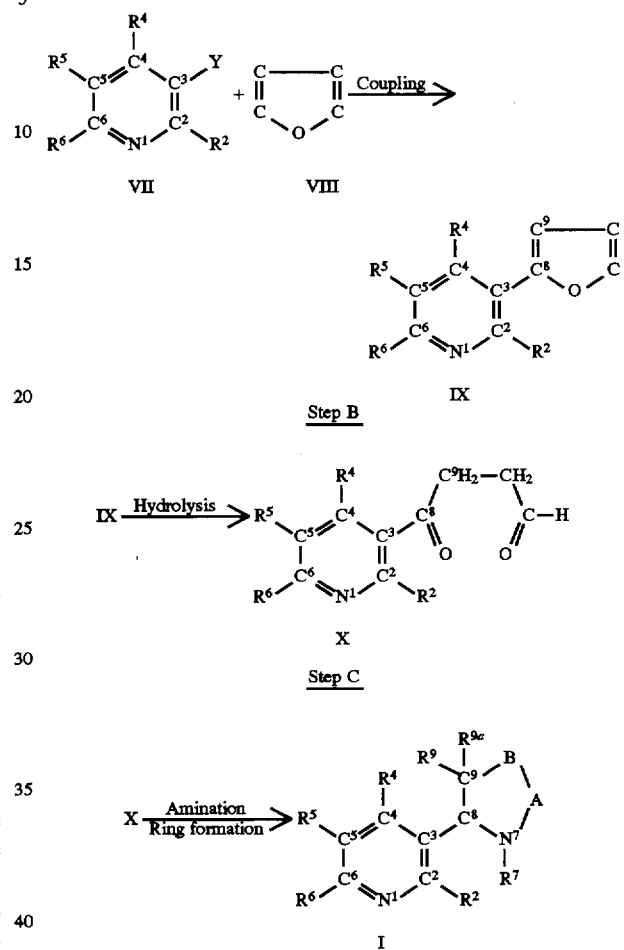

In the above scheme, Y is an active functionality which is capable of undergoing a transition metal catalyzed coupling reaction. Examples of Y include bromine, iodine, trifluoromethylsulfonyloxy, and the like. In Step A of Reaction Scheme II, a coupling reaction is carried out, typically promoted by an organometallic coupling catalyst. A presently preferred method for carrying out the desired coupling reaction is to metallate furan VIII with a suitable organometallic reagent (e.g., tert-butyllithium followed by zinc chloride, tributyltin chloride, trimethyltin chloride, triisopropylborate, and the like), followed by coupling of the metallated species with pyridine derivative VII in the presence of a transition metal catalyst (e.g., $PdCl_2(PPh_3)_2$) in a suitable solvent (e.g., ether or THF).

The coupling reaction is typically allowed to proceed by allowing the reaction temperature to warm slowly from about −78° C. up to ambient temperature over a period of several hours. The reaction mixture is then maintained at ambient temperature for a time in the range of about 4 up to 24 hours, with about 12 hours typically being sufficient.

The coupling product, pyridylfuran IX, can be isolated and purified employing standard techniques, such as solvent extraction, chromatography, crystallization, distillation, and the like.

Conversion of pyridylfuran IX to the pyridylpyrrolidine of Formula I (wherein A and B each are $CH_2$ and $R^9$ and $R^{9a}$ are each H) can be achieved in a two-step process, as illustrated in Steps B and C of Scheme II. Thus, in Step B, the furan group is hydrolyzed by contacting pyridylfuran IX with aqueous media containing a strong acid (e.g., sulfuric acid) under reflux conditions for a time in the range of about 1 up to 48 hours. The resulting dicarbonyl compound of Formula X can then be cyclized to the pyrrolidine of Formula I by treatment with a suitable amine, such as $R^7NH_2$. Amination/ring formation contemplated by Step C of Scheme II is typically carried out in the presence of a suitable reducing agent (such as described above with reference to Scheme I, Step C).

As is known in the art, cyclization of dicarbonyl compound X can be carried out under conditions which promote stereoselective ring formation, thereby producing substantially optically pure products. See, for example, Manescalchi, Nardi and Savoia in Tetrahedron Letters 35:2775 (1994).

When any one or more of $R^2$, $R^4$, $R^5$ or $R^6$ of compounds of Formula I are reactive substituents (e.g., bromine, iodine, trifluoromethylsulfonyloxy, and the like), it is possible to further modify such compounds taking advantage of the presence of the reactive functionality. One such modification is shown in Scheme III.

Scheme III

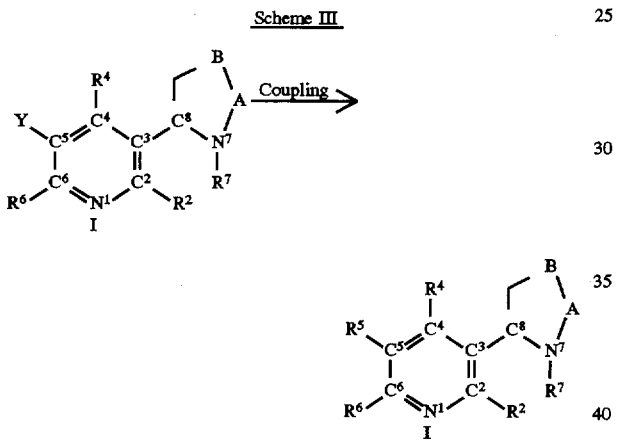

In Scheme III, the starting material employed is a compound of the Formula I, wherein Y is as defined above. If $R^5$ in the desired final product is an aryl or substituted aryl group, such products can be prepared employing well known organometallic procedures, such as, for example, by coupling with an arylzinc compound (prepared by reaction of an arylbromide with an alkyllithium reagent such as n-butyllithium or tert-butyllithium, followed by addition of zinc chloride) with compound of Formula I, wherein Y is as defined above, in the presence of a catalytic amount of a suitable coupling catalyst (e.g., $PdCl_2(PPh_3)_2$, and the like) in a suitable solvent such as toluene, dimethylformamide, THF, and the like. Suitable reaction temperatures fall in the range of about 0° C. to 140° C. (with temperatures in the range of about 0° C. up to 80° C. being preferred), with reaction times in the range of about 4 up to 24 hours.

Similarly, coupling procedures can be used to prepare compounds of Formula I in which $R^2$, $R^4$, $R^5$ and $R^6$ are independently alkyl, alkenyl, alkynyl, arylalkyl, alkylaryl, and the like. An alternative method to promote the desired coupling reaction employs organoborane chemistry, wherein arylboronic acids, in the presence of a suitable catalyst (e.g., $Pd(Ph_3)_4$) in basic aqueous dimethoxyethane are coupled with compounds of Formula I wherein one or more of $R^2$, $R^4$, $R^5$ and $R^6$ is Y. The reaction is typically carried out at a temperature in the range of about 40° C. up to 150° C. (with a temperature in the range of about 80° C. being preferred), for a time in the range of about 1 up to 24 hours (with about 8 hours being preferred). Arylboronic acids are well known in the art and can be readily obtained by those of skill in the art.

Yet another method for the preparation of compounds of Formula I is described in Scheme IV.

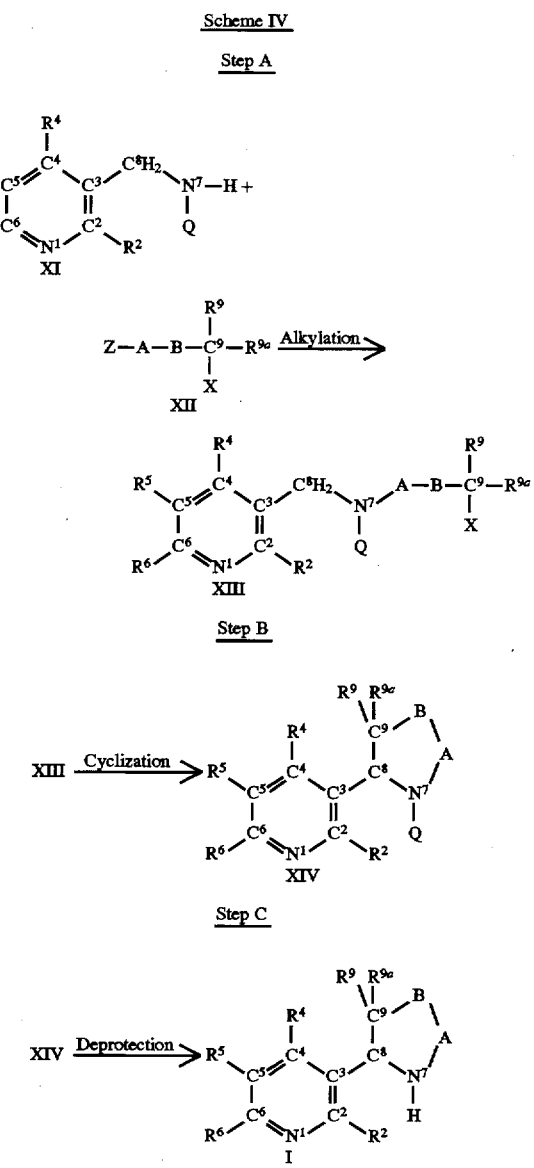

In Scheme IV, Q represents a protecting group that enhances the acidity of the adjacent hydrogen atom, and X and Z are leaving groups (such as halogen). An example of Q is the tert-butyloxycarbonyl group. Groups X and Z are independently selected from I, Br or Cl. It is preferred that in X is Br, then Z is I, or, alternatively, if X is Cl, Z is Br or I.

In Step A of Scheme IV, the protected pyridylamine of Formula XI is alkylated with alkylating moiety XII. This reaction proceeds in the presence of a strong base (e.g., sodium hydride, lithium hexamethyldisilazide, lithium diisopropylamide, and the like) in polar aprotic solvent (e.g., THF, diethyl ether, tert-butyl methyl ether, and the like).

Reaction is typically carried out at a temperature in the range of about −78° C. up to 100° C., where the actual temperature employed varies depending on the nature of X, Z and the substituents on XII. Typically, the reaction is carried out at ambient temperature for a period of time ranging from about 1 to 24 hours.

The resulting alkylated pyridylamine of Formula XIII can then be isolated and purified using techniques known in the art such as extraction with an organic solvent and concentration, followed by chromatography, recrystallization, and the like.

The ring forming cyclization contemplated by Step C is promoted by strong base (e.g., alkyllithiums, sec-butyllithium, tert-butyllithium, and the like). Reaction is carried out in suitable solvent (e.g., THF, diethyl ether, tert-butyl methyl ether, and the like), initially at low temperature (e.g., −78° C.), then allowed to warm gradually to ambient temperature. Reaction time varies as a function of the substituents present on the reacting species. Generally, where $R^9$ is a large (bulky) group, longer reaction times will be required. Typical reaction times fall in the range of about 1 up to 24 hours, with 4 hours generally being sufficient.

The resulting protected cyclic amine of Formula XIV can be isolated and purified by standard techniques well known by those of skill in the art, e.g., chromatographic techniques such as flash chromatography.

The deprotection reaction depicted in Step C can be carried out using techniques known in the art. This deprotection reaction is typically achieved by acid treatment (e.g., employing trifluoroacetic acid or hydrogen chloride in a suitable solvent such as diethyl ether). The resulting cyclic amine can then be isolated and purified by well known procedures, as described above.

In another example, compounds of Formula I in which $R_7$ is hydrogen can be prepared using methodology depicted in Scheme V. See, for example, Nilsson and Hallberg in *J. Org. Chem.* 55:2464 (1990).

Scheme V

Step A

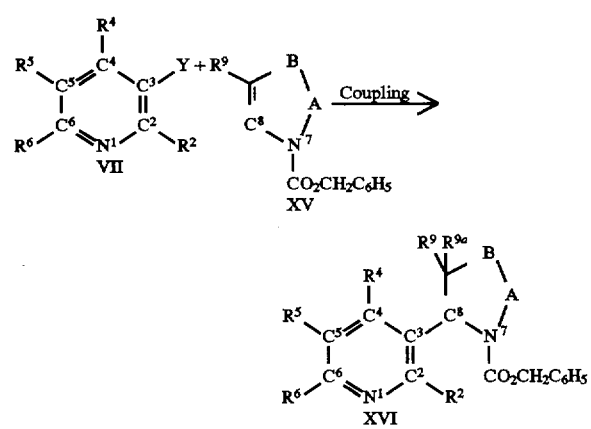

Step B

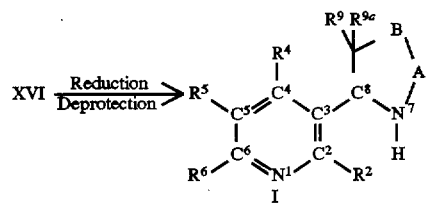

Step A of Scheme V is an organometallic catalyzed coupling reaction (also known as the Heck reaction). Typically, a pyridine of Formula VII is contacted with a protected, cyclic enamine of Formula XV in the presence of $Pd(OAc)_2$ and triethylamine in a suitable solvent. The reaction temperature typically falls in the range of about 0° C. up to 140° C. (with a temperature of about 80° C. being preferred). Reaction time can vary widely, typically falling in the range of about 8 hours up to several days (with at least about 24 hours generally being required to allow the coupling reaction to go to completion).

The resulting unsaturated cyclic amine of Formula XVI can then be isolated and purified employing standard techniques (e.g., distillation, chromatography, and the like).

If enantiomerically enriched compound of Formula XVI is desired, asymmetric Heck reactions, which are well known in the art, can be employed. Thus, a chiral catalyst (e.g., (R)-BINAP, i.e., the (R) configuration of 2,2'-bis (diphenylphosphino)-1,1'-binaphthyl) can be used to induce the formation of chiral product. See, for example, Ozawa, Kobatake and Hayashi in *Tetrahedron Letters* 34:2507 (1993).

Conversion of the unsaturated, protected cyclic amine to compounds of Formula I can be achieved in a single step, as illustrated in Step B. Thus, catalytic hydrogenation in the presence of a suitable catalyst (e.g., $PtO_2$, Pd/C, and the like), in a suitable solvent (e.g., ethanol, acetic acid, and the like), provides compounds of Formula I. Alternatively, sequential deprotection, followed by reduction can be carried out (employing methods described above with respect to Scheme I, Step C).

Another procedure which can be used to prepare compounds embraced by Formula I is set forth in Scheme VI below.

Scheme VI

Step A

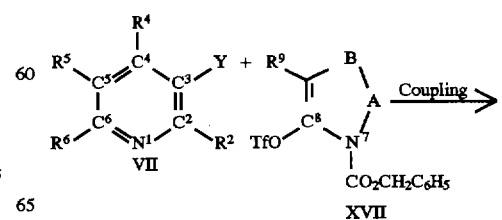

-continued
Scheme VI

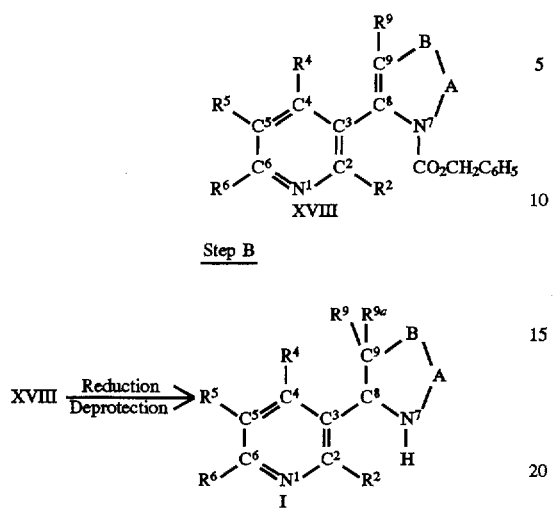

Scheme VII

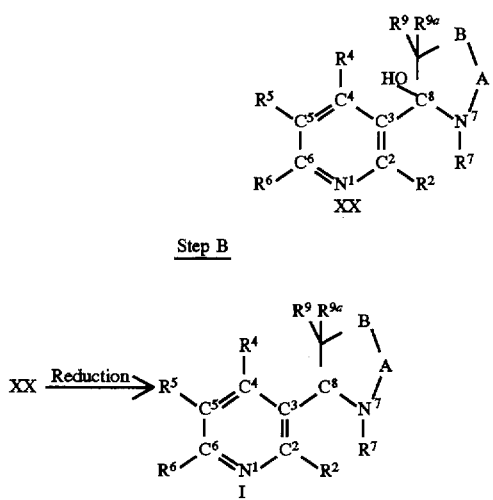

In the above scheme, Tf represents the trifluoromethylsulfonyl group. In Step A, pyridines of Formula VII are coupled with an enol triflate of Formula XVII in the presence of a suitable organometallic catalyst (e.g., PdDBA, Pd(PPh$_3$)$_4$, PdCl$_2$(PPh$_3$)$_2$, and the like), triphenylphosphine or triphenylarsine, and lithium chloride in an aprotic solvent (e.g., dimethylformamide, THF, dimethoxyethane, N-methylpyrrolidone, and the like). Reaction temperatures typically fall in the range of about 0° C. up to 140° C. (with about 80° C. being preferred). Reaction times generally fall in the range of about 4 up to 72 hours (with about 12 hours generally being sufficient). The coupling reaction product can then be isolated and purified employing standard techniques (e.g., extraction, chromatography, recrystallization, and the like).

In Step B, catalytic hydrogenation of compound of Formula XVIII in the presence of suitable hydrogenation catalyst (e.g., Pd/C, PtO$_2$, and the like) simultaneously saturates the double bond in XVIII, and removes the benzyloxycarbonyl protecting group, thereby producing compounds of Formula I. As noted above, asymmetric hydrogenation techniques can be employed in Step B to afford substantially optically pure compounds of Formula I.

Another synthetic strategy which can be employed for the preparation of compounds of Formula I is presented in Scheme VII. See, for example, Huang, Chu and Fowler in J. Org. Chem. 1985 50:3885.

Scheme VII

Step A

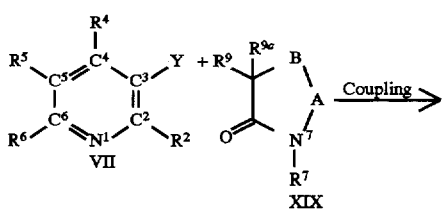

In Step A of Scheme VII, the lithium derivative of pyridine VII is coupled with lactam XIX. This coupling reaction is carried out in an aprotic solvent as follows. Pyridine VII in suitable solvent (e.g., diethyl ether) is contacted with an alkyllithium (e.g., tert-butyllithium) at a temperature in the range of about −78° C. up to 0° C. Lactam XIX is then added to the reaction mixture and the coupling reaction allowed to proceed for a time in the range of about 15 minutes up to about 8 hours. The reaction mixture is then neutralized and alcohol XX recovered by solvent extraction.

In Step B, the alcohol group of compound XX is removed by reduction thereof. While hydride reduction or hydrogenation conditions can be employed, the choice of reduction conditions is based, at least in part, on the chemical nature of the substituents on compound XX. For example, alcohol XX can be treated with lithium aluminum hydride in ether for 1–12 hours at temperatures in the range of about 20° C. up to reflux. Alternatively, alcohol XX can be dissolved in a suitable solvent (e.g., ethanol, acetic acid, and the like) and then exposed to hydrogen under hydrogenation conditions in the presence of a suitable catalyst (e.g., Pd/C, PtO$_2$, and the like). Hydrogenation conditions typically comprise ambient temperature at pressures in the range of about 1–10 atmospheres of hydrogen (with 2–3 atmospheres being preferred).

In addition to the above-described synthetic procedures, those of skill in the art have access to numerous other synthetic procedures which can be employed for the preparation of invention compounds. Indeed, the literature is replete with methodologies useful for the preparation of the basic nicotine and anabasine nuclei, which can then be modified to introduce the necessary substituents to satisfy the requirements of Formula I.

In accordance with another embodiment of the present invention, there are provided pharmaceutical compositions comprising pyridine compounds as described above, in combination with pharmaceutically acceptable carriers. Optionally, invention compounds can be converted into non-toxic acid addition salts, depending on the substituents thereon. Thus, the above-described compounds (optionally in combination with pharmaceutically acceptable carriers) can be used in the manufacture of a medicament for modulating the activity of acetylcholine receptors.

Pharmaceutically acceptable carriers contemplated for use in the practice of the present invention include carriers suitable for oral, intravenous, subcutaneous, transcutaneous, intramuscular, intracutaneous, inhalation, and the like administration. Administration in the form of creams, lotions, tablets, dispersible powders, granules, syrups, elixirs, sterile aqueous or non-aqueous solutions, suspensions or emulsions, patches, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Invention compounds can optionally be converted into non-toxic acid addition salts. Such salts are generally prepared by reacting the compounds of this invention with a suitable organic or inorganic acid. Representative salts include the hydrochloride, hydrobromide, sulfate, bisulfate, methanesulfonate, acetate, oxalate, valerate, oleate, laurate, borate, benzoate, lactate, phosphate, tosylate, citrate, maleate, fumarate, succinate, tartrate, napsylate, and the like. Such salts can readily be prepared employing methods well known in the art.

In accordance with yet another embodiment of the present invention, there are provided methods of modulating the activity of acetylcholine receptors, said method comprising:
  contacting cell-associated acetylcholine receptors with a concentration of a pyridine compound as described above sufficient to modulate the activity of said acetylcholine receptors.

As employed herein, the phrase "modulating the activity of acetylcholine receptors" refers to a variety of therapeutic applications, such as the treatment of Alzheimer's disease and other disorders involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulemia and anorexia; disorders of nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardiac arrhythmias, comedication in surgical procedures, and the like.

The compounds of the present invention are especially useful for the treatment of Alzheimer's disease as well as other types of dementia (including dementia associated with AIDS), Parkinson's disease, cognitive dysfunction (including disorders of attention, focus and concentration), attention deficit syndrome, affective disorders, and for the control of pain. Thus modulation of the activity of acetylcholine receptors present on or within the cells of a patient suffering from any of the above-described indications will impart a therapeutic effect.

As employed herein, the phrase "an effective amount", when used in reference to compounds of the invention, refers to doses of compound sufficient to provide circulating concentrations high enough to impart a beneficial effect on the recipient thereof. Such levels typically fall in the range of about 0.001 up to 100 mg/kg/day; with levels in the range of about 0.05 up to 10 mg/kg/day being preferred.

The invention will now be described in greater detail by reference to the following non-limiting examples.

EXAMPLE 1

Ethyl 5-bromo-3-pyridinecarboxylate

To a slurry of 5-bromo-3-pyridinecarboxylic acid (100.0 g, 0.495 mol) in 1,2-dichloroethane (200 mL), thionyl chloride (108 mL, 1.485 mmol) was slowly added over a period of 30 min with intermittent cooling in an ice bath to maintain a temperature below 20° C. The reaction mixture was allowed to warm to room temperature, and heated to reflux for 18 h. The reaction mixture was cooled to 10° C., and additional thionyl chloride (14.7 g, 0.12 mmol) was added dropwise. The reaction was warmed to reflux for 6 h, then allowed to cool to room temperature. Residual thionyl chloride and solvent were removed by rotary evaporation followed by high vaccum to provide 5-bromo-3-pyridinecarbacyl chloride hydrochloride as a colorless solid (128 g, 101%).

To a suspension of 5-bromo-3-pyridinecarbacyl chloride (98.5 g, 0.39 mmol) in 1,2-dichloromethane at 0° C. absolute ethanol (50 mL) was added dropwise over period of 1.5 h. The resulting clear solution was stirred at room temperature for 2 h and the unreacted ethanol and solvent were removed by rotary evaporation followed by high vacuum. The off-white solid remaining was dissolved in 1N aqueous hydrochloric acid and washed with three 75 mL portions of dichloromethane. The aqueous phase was adjusted to pH 12 by the addition of solid sodium hydroxide and extracted three times with 75 mL portions of dichloromethane. The combined organic phases from the basic extraction were treated with magnesium sulfate and activated charcoal, and filtered through Celite™. Heptane (250 mL) was added and the pale yellow solution of crude product was concentrated to 300 mL by rotary evaporation then slowly cooled to $-20°$ C. to induce crystallization. An initial crop of colorless crystals (51.5 g) was collected. Several further crops were produced by concentration of the remaining mother liquors which after further purification by fractional crystallization from heptane provided additional product (18.9 g). The purified later crops were combined with the the initial crop to provide ethyl 5-bromo-3-pyridinecarboxylate (70.4 g, net 78%) as a colorless crystalline solid. M.p. 40°–41° C. (heptane); $^1$HNMR (CDCl$_3$, 300 MHz) δ 9.13 (d, J=1.8 Hz, 1 H), 8.84 (d, J=2.3 Hz, 1 H), 8.44 (t, J=2.0 Hz, 1 H), 4.43 (q, J=7.2 Hz, 2 H), 1.42 (t, J=7.2 Hz, 3 H).

EXAMPLE 2

5-Bromo-3-(2-pyrrolin-1-yl)pyridine

A mixture of lithium bis(trimethylsilyl)amide (300 mL of a 1M solution in THF, 300 mmol) and t-butyl methyl ether (250 mL) under inert atmosphere was cooled to −50° C. (internal temperature) and N-vinylpyrrolidinone (32 mL, 300 mmol) was added. Stirring was continued for 30 minutes at −50° C. and ethyl 5-bromo-3-pyridinecarboxylate (44.5 g, 193 mmol) in t-butyl methyl ether (100 mL) was added. The reaction mixture was allowed to warm to 25° C. and stirred for 18 h before quenching the reaction with a mixture acetic acid (20 mL) and methanol (20 mL). The solvents were removed in vacuo, water (100 mL) and concentrated HCl (100 mL) were added and the mixture heated under reflux for 18 h.

The reaction flask was cooled to 0° C. and basified with sodium hydroxide solution (60 g in 250 mL water) and extracted with dichloromethane (3×200 mL). The combined organic extracts were washed with brine (100 mL), dried (MgSO$_4$) and concentrated in vacuo. The residue was dissolved in the minimum amount of dichloromethane and filtered through a pad of silica gel with ethyl acetate as the eluant. The filtrate was concentrated in vacuo and the solid which crystallized out during this process was collected, washed with ethyl acetate and dried to afford 5-bromo-3-(2-pyrrolin-1-yl)pyridine (26 g, 60%) as a solid. M.p. 98°–99° C. (EtOAc); $^1$H NMR (CDCl$_3$, 300 MHz) δ 8.88 (s, 1 H), 8.71 (s, 1 H), 8.35 (d, J=2 Hz, 1 H), 4.10 (td, J=8, 2 Hz, 2 H), 2.94 (td, J=8, 2 Hz, 1 H), 2.09 (quintet, J=8 Hz, 2 H).

EXAMPLE 3

5-Bromo-3-(2-pyrrolidinyl)pyridine

To a stirred slurry of 5-bromo-3-(2-pyrrolin-1-yl)pyridine (23.25 g, 0.103 mol) in 8:2 methanol:acetic acid (250 mL) at −78° C. under inert atmosphere was slowly added solid sodium borohydride (1.96 g, 0.052 mol) in several portions over 1.5 h so as to maintain an internal temperature below −60° C. The reaction mixture was allowed to warm to 0° C. and stirred for 3 h, followed by an additional 17 h at room temperature.

The reaction mixture was diluted with 75 mL of water and the organic solvents were removed by rotary evaporation to leave an orange solution which was then diluted with water to 300 mL providing a solution of pH 3.5. The acidic solution was washed 4 times with 75 mL portions of methylene chloride, the pH of the aqueous phase was adjusted to 12 with solid sodium hydroxide, then extracted twice with 100 mL portions of chloroform. The combined chloroform fractions were treated with magnesium sulfate and activated charcoal, filtered through Celite™, and the solvent was removed by rotary evaporation followed high vacuum. 5-Bromo-3-(2-pyrrolidinyl)pyridine (20.34 g, 88%) was obtained as a pale yellow oil. LRMS (EI) m/e 227 (C$_9$H$_{11}$N$_2$$^{81}$Br—H$^+$), 225 (C$_9$H$_{11}$N$_2$$^{79}$Br—H$^+$); $^1$H NMR (DMSO-d$_6$, 300 MHz) δ 8.53 (d, J=2.2 Hz, 1 H), 8.49 (d, J=1.8 Hz, 1 H), 7.91 (t, J=2.0 Hz, 1 H), 4.17 (t, J=7.7 Hz, 1 H), 3.18 (m, 1 H), 3.06 (m, 1 H), 2.00 (m, 1 H), 2.07 (s, 1 H), 2.00–1.77 (m, 2 H), 1.63 (m, 1 H).

EXAMPLE 4

5-Bromo-3-(1-methyl-2-pyrrolidinyl)pyridine

To a solution of 5-bromo-3-(2-pyrrolidinyl) pyridine (18.14 g, 80.6 mmol) in acetonitrile (250 mL) at a temperature of 0° C. was added an aqueous solution of formaldehyde (60.4 mL, 37% by weight, 806 mmol) and the mixture was stirred for 20 min. Solid sodium cyanoborohydride (7.60 g, 120 mmol) was added in several portions over 30 min, and the reaction mixture was stirred at 0° C. for an additional 90 min, then 3.0 mL of acetic acid was added and the reaction was allowed to warm to room temperature and stirred for 15 h.

The reaction mixture was diluted with 75 mL of 1M aqueous hydrochloric acid and the organic solvents were removed by rotary evaporation. The residue was adjusted to pH 2.5 by the addition of 1N HCl and extracted three times with 75 mL portions of methylene chloride. The aqueous phase was basified to pH 12 by the addition of solid sodium hydroxide and extracted three times with 75 mL portions of methylene chloride. The organic phases from the basic extraction were combined and treated with magnesium sulfate and activated charcoal, then filtered through Celite™. The solvent was removed by rotary evaporation, and the residual solvent was removed under high vacuum to provide 5-bromo-3 (1-methyl-2-pyrrolidinyl)pyridine (18.19 g, 95%) as a pale yellow oil. LRMS (EI) m/e 242 (C$_{10}$H$_{13}$N$_2$$^{81}$Br), 241 (C$_{10}$H$_{13}$N$_2$$^{79}$Br—$^+$H), 240 (C$_{10}$H$_{13}$N$_2$$^{79}$Br), 239 (C$_{10}$H$_{13}$N$_2$$^{79}$Br—$^+$H); $^1$H NMR (DMSO-d$_6$, 300 MHz) δ 8.55 (d, J=2.1 Hz, 1 H), 8.44 (d, J=1.9 Hz, 1 H), 7.88 (t, J=1.9 Hz, 1 H), 3.24 (bd-t, J=8.1 Hz, 1 H), 3.10 (t, J=8.0 Hz, 1 H), 2.36 (m, 1 H), 2.18 (s, 3 H), 1.95 (m, 1 H), 1.85 (m, 1 H), 1.70 (m, 1 H).

EXAMPLE 5

5-Bromo-3-(2-piperidin-1-yl)pyridine

δ-Valerolactam (5.95 g, 60 mmol) in anhydrous THF (15 mL) was added to a stirred solution of lithium diisopropylamide (30 mL of a 2M solution in THF/heptane/ethylbenzene, 60 mmol) in THF (40 mL) at −78° C. under inert atmosphere. After 10 minutes, chlorotrimethylsilane (7.6 mL, 60 mmol) was added and the reaction mixture was allowed to warm to 25° C. for 2 h. The reaction mixture was again cooled to −78° C. and a further equivalent of lithium diisopropylamide (30 mL of a 2M solution in THF/heptane/ethylbenzene, 60 mmol) was added. A solution of ethyl 5-bromo-3-pyridinecarboxylate (9.2 g, 40 mmol) in anhydrous THF (15 mL) was added at −78° C. and the mixture was stirred at 25° C. for 18 h.

The reaction was quenched with methanol (50 mL) and the solvents removed in vacuo. Concentrated HCl (30 mL) and water (10 mL) were carefully added and the mixture was heated under reflux for 2 h. Analysis by thin layer chromatography and GC/MS indicated the presence of product and the cooled (0° C.) mixture was basified with solid sodium hydroxide pellets. The aqueous mixture was extracted with chloroform (3×100 mL), the combined organic extracts washed with brine (50 mL), dried (Na$_2$SO$_4$) and concentrated in vacuo. The residue was chromatographed using "flash" silica gel with ethyl acetate as eluant to afford a product which became dark and gummy on standing. This was therefore used in the next step without further purification. LRMS (EI) m/e 240 (C$_{10}$H$_{11}$N$_2$$^{81}$Br), 239 (C$_{10}$H$_{11}$N$_2$$^{79}$Br—$^+$H), 238 (C$_{10}$H$_{11}$N$_2$$^{79}$Br), 237 (C$_{10}$H$_{11}$N$_2$$^{79}$Br—$^+$H).

EXAMPLE 6

5-Bromo-3-(2-piperidinyl)pyridine

5-Bromo-3- (2-piperdine-1-yl) pyridine was dissolved in a mixture of methanol (50 mL) and acetic acid (12 mL) and cooled to −40° C. Sodium borohydride (3.2 g, 85 mmol) was added in portions keeping the internal temperature below −20° C. The reaction mixture was then stirred at 25° C. for 1 h before the addition of 1M HCl (10 mL) and evaporation of the solvents in vacuo. Water (100 mL) was added and the resulting solution made basic with solid NaOH. The aqueous mixture was extracted with dichloromethane (3×100 mL), the combined organic extracts washed with brine (50 mL), dried (Na$_2$SO$_4$) and concentrated in vacuo. The residue was chromatographed using "flash" silica gel with ethyl acetate followed by 10% methanol in ethyl acetate as eluants to afford the title compound as colorless needles, 2.76 g, 41%. M.p. 97°–97.5° C. (EtOAc); $^1$H NMR (CDCl$_3$, 300 MHz): δ 8.54 (d, J=2 Hz, 1 H), 8.48 (d, J=2 Hz, 1 H), 7.91 (t, J=2 Hz, 1 H), 3.62 (dd, J=10, 2.5 Hz, 1 H), 3.19 (dm, J=12 Hz, 1 H), 2.78 (ddd, J=12, 12, 3 Hz 1 H), 1.4–2.0 (m, 7 H).

EXAMPLE 7

5-Bromo-3-(2-N-tert-butoxycarbonylpiperidinyl) pyridine

5-Bromo-3-(2-piperidinyl)pyridine (3.01 g, 12.5 mmol), di-tert-butyl dicarbonate (2.84 g, 13 mmol) and triethylamine (1.81 mL, 13 mmol) were dissolved in dichloromethane (50 mL) and stirred at 0° C. under a drying tube. 4-Dimethylaminopyridine (80 mg, 0.65 mmol) was added and the mixture was stirred at 25° C. for 18 h. The solvents were removed in vacuo and the residue chromatographed on "flash" silica gel with ethyl acetate:hexane (1:3) as eluant to afford the title compound as a solid, 3.7 g, 87%. $^1$H NMR (CDCl$_3$, 300 MHz): δ 8.51 (s, 1 H), 8.38 (s, 1 H), 7.62 (m, 1 H), 5.40 (bs, 1 H), 4.03 (d, J=13 Hz, 1 H), 2.68 (app. t, J=13 Hz, 1 H), 2.20 (d, J=14 Hz, 1 H), 1.89 (m, 1 H), 1.43 (d, 9 H), 1.2–1.7 (m, 4 H).

EXAMPLE 8

5-(4-Chlorophenyl)-3-(1-methyl-2-pyrrolidinyl) pyridine fumarate

To a stirred solution of 4-bromochlorobenzene (1.91 g, 10 mmol) in anhydrous diethyl ether (10 mL) at –78 ° C. under inert atmosphere was slowly added t-butyllithium (11.76 mL of a 1.7M solution in pentane, 20 mmol). This was stirred at –78° C. for 30 minutes and zinc chloride (10 mL of a 1M solution in diethyl ether, 10 mmol) was added. The reaction mixture was allowed to warm to 25° C. over 30 minutes before being cannulated into a stirred solution of 5-bromo-3-(1-methyl-2-pyrrolidinyl)pyridine (1 g, 4.16 mmol) and bis(triphenylphosphine)palladium(II) chloride (175 mg, 0.25 mmol) in anhydrous THF (10 mL) at 25° C. under inert atmosphere. The reaction mixture was stirred for 18 h before being poured into a saturated solution of potassium sodium tartrate (50 mL).

The solids were removed by filtration, the organic phase separated and the aqueous phase washed with ethyl acetate (2×100 mL). The combined organic layers were washed with brine (50 mL), dried (MgSO$_4$) and the solvents removed in vacuo. The resulting oil was dissolved in methanol (50 mL) and filtered through paper to remove residual solid catalyst. The filtrate was concentrated under reduced pressure before purification using "flash" silica gel column chromatography with ethyl acetate:hexane (1:4, 1:3, 1:1) as eluant to afford 5-(4-chlorophenyl)-3-(1-methyl-2-pyrrolidinyl) pyridine, 1.01 g, 91% as an oil.

The above-referenced pyridine was converted into invention compound of Formula I by the addition of one equivalent of fumaric acid to a methanol (15 mL) solution of the free amine at 25° C. After 30 minutes the solvent was removed in vacuo and the residue pumped under high vacuum. Trituration with diethyl ether followed by recrystallization from ethyl acetate afforded 5-(4-chlorophenyl)-3-(1-methyl-2-pyrrolidinyl)pyridine fumarate, (72%) as a colorless solid. M.p. 159°–160° C. (EtOAc); $^1$H NMR (DMSO-d$_6$, 300 MHz): δ 8.84 (d, J=3 Hz, 1 H), 8.58 (d, J=3 Hz, 1 H), 8.08 (t, J=2 Hz, 1 H), 7.79 (d, J=8 Hz, 2 H), 7.56 (d, J=8 Hz, 2 H), 6.62 (s, 2 H), 3.49 (t, J=6 Hz, 1 H), 3.32 (m, 1 H), 2.52 (m, 1 H), 2.28 (m, 1 H), 2.24 (s, 3 H), 1.9 (m, 3 H).

EXAMPLE 9

Synthesis of Additional Compounds of Formula I

Repeating the procedure of Example 8, but using the appropriate starting materials in place of 4-bromochlorobenzene, the following compounds were obtained:

(a) 5-(4-Chloro-3-fluorophenyl)-3-(1-methyl-2-pyrrolidinyl)pyridine fumarate;
M.P. 183°–184° C. (EtOAc); $^1$H NMR (DMSO-d$_6$, 300 MHz): δ 8.89 (s, 1 H), 8.61 (s, 1 H), 8.15 (s, 1 H), 7.90 (d, J=12 Hz, 1 H), 7.70 (m, 2 H), 6.61 (s, 2 H), 3.55 (m, 1 H), 3.37 (m, 1 H), 2.53 (m, 1 H), 2.26 (s, 3 H), 1.90 (m, 4 H).

b) 5-(3-Fluorophenyl)-3-(1-methyl-2-pyrrolidinyl) pyridine fumarate;
M.P. 153°–185° C. (EtOAc); $^1$H NMR (DMSO-d$_6$, 300 MHz): δ 8.86 (d, J=3 Hz, 1 H), 8.58 (d, J=2 Hz, 1 H), 8.10 (t, J=3 Hz, 1 H), 7.60 (m, 3 H), 7.28 (m, 1 H), 6.63 (s, 3 H), 3.47 (t, J=6 Hz, 1 H), 3.32 (m, 1 H), 2.49 (m, 1 H), 2.28 (m, 1 H), 2.23 (s, 3 H), 1.10 (m, 3 H).

c) (E)-5-(2-Phenyl-1-ethenyl)-3-(1-methyl-2-pyrrolidinyl)pyridine fumarate;
M.P. 162°–163° C. (EtOH-EtOAc); $^1$H NMR (DMSO-d$_6$, 300 MHz): δ 8.68 (d, J=2 Hz, 1 H), 8.42 (d, J=2 Hz, 1 H), 8.02 (app. t, J=2 Hz, 1 H), 7.64 (d, J=7 Hz, 2 H), 7.42 (d, J=16.5 Hz, 1 H), 7.40 (t, J=7.5 Hz, 2 H), 7.30 (d, J=16.5 Hz, 1 H), 7.30 (t, J=7 Hz, 1 H), 6.62 (s, 3 H), 3.28 (m, 2 H), 2.39 (q, J=9 Hz, 1 H), 2.24 (m, 1 H), 2.17 (s, 3 H), 1.7–1.9 (m, 3 H).

d) 5-(3-Chlorophenyl)-3-(1-methyl-2-pyrrolidinyl) pyridine fumarate;
M.P. 139°–141° C. (EtOH); $^1$H NMR (CD$_3$OD, 300 MHz): δ 8.78 (d, J=2 Hz, 1 H), 8.57 (d, J=2 Hz, 1 H), 8.21 (t, J=2 Hz, 1 H), 7.66 (m, 1 H), 7.56 (m, 1 H), 7.38 (m, 2 H), 6.60 (s, 2 H), 4.12 (t, J=6 Hz, 1 H), 3.66 (m, 1 H), 3.0 (m, 1 H), 2.58 (s, 3 H), 2.20 (m, 4 H).

e) 5-(3-Fluoro-4-methoxyphenyl)-3-(1-methyl-2-pyrrolidinyl)pyridine fumarate;
M.P. 162°–164° C. (EtOH); $^1$H NMR (CD$_3$OD, 300 MHz): δ 8.87 (d, J=3 Hz, 1 H), 8.62 (d, J=3 Hz, 1 H), 8.34 (t, J=3 Hz, 1 H), 7.50 (m, 2 H), 7.21 (m, 1 H), 6.70 (s, 4 H), 4.44 (dd, J=10, 7.5 Hz, 1 H), 3.90 (s, 3 H), 3.90 (m, 1 H), 3.26 (m, 1 H), 2.76 (s, 3 H), 2.2–2.7 (m, 4 H).

f) 5-Phenyl-3-(1-methyl-2-pyrrolidinyl)pyridine fumarate;
M.P. 145°–146° C. (EtOAc); $^1$H NMR (D$_2$O, 300 MHz): δ 8.55 (s, 1 H), 8.33 (s, 1 H), 8.03 (s, 1 H), 7.32 (m, 2 H), 7.17 (m, 3 H), 6.28 (s, 3 H), 4.21 (bm, 1 H), 3.53 (bm, 1 H), 3.03 (bm, 1 H), 2.46 (s, 3 H), 2.28 (m, 1 H), 1.9–2.15 (m, 3 H).

EXAMPLE 10

5-(4-Fluorophenyl)-3-(1-methyl-2-pyrrolidinyl) pyridine fumarate

To a stirred solution of 4-bromofluorobenzene (1.75 g, 10 mmol) in anhydrous diethyl ether (5 mL) at –10° C. under inert atmosphere was slowly added n-butyllithium (6.25 mL of a 1.6M solution in hexanes, 10 mmol). This was stirred at −10° C. for 30 minutes and zinc chloride (10 mL of a 1M solution in diethyl ether, 10 mmol) was added. The mixture was allowed to warm to 25° C. over 30 minutes before being cannulated into a stirred solution of 5-bromo-3-(1-methyl-2-pyrrolidinyl)pyridine (1.1 g, 4.6 mmol) and bis(triphenylphosphine)palladium(II) chloride (175 mg, 0.25 mmol) in anhydrous THF (10 mL) at 25° C. under inert atmosphere. The reaction mixture was stirred for 18 h before being poured into a saturated solution of potassium sodium tartrate (50 mL).

The organic phase was separated and the aqueous phase washed with ethyl acetate (2×100 mL). The combined organic layers were washed with brine (50 mL), dried ($Na_2SO_4$) and the solvents removed in vacuo. The resulting oil was dissolved in methanol (50 mL) and filtered through paper to remove residual solid catalyst. The filtrate was concentrated under reduced pressure before purification using "flash" silica gel column chromatography with ethyl acetate:hexane (1:4, 1:3, 1:1) as eluant to afford 5-(4-fluorophenyl)-3-(1-methyl-2-pyrrolidinyl) pyridine, 793 mg, 63% as an oil.

The pyridine derivative described above was converted to a compound of the invention having Formula I by the addition of one equivalent of fumaric acid to a methanol (15 mL) solution of the free amine at 25° C. After 30 minutes the solvent was removed in vacuo and the residue pumped under high vacuum. Trituration with diethyl ether followed by recrystallization from ethyl acetate afforded 5-(4-fluorophenyl)-3-(1-methyl-2-pyrrolidinyl) pyridine fumarate, (63%). M.p. 159°–160° C. (EtOAc); $^1$H NMR ($D_2O$, 300 MHz): δ 8.87 (s, 1 H), 8.68 (s, 1 H), 8.26 (s, 1 H), 7.73 (dd, J=8, 6 Hz, 2 H), 7.30 (app. t, J=8 Hz, 2 H), 6.61 (s, 2H), 4.56 (bm, 1 H), 3.91 (bm, 1 H), 3.41 (bm, 1 H), 2.83 (s, 3 H), 2.67 (m, 1 H), 2.3–2.5 (m, 3 H).

EXAMPLE 11

Synthesis of Additional Compounds of Formula I

Repeating the procedure of Example 10, but using the appropriate starting materials in place of 4-bromofluorobenzene, the following compounds were obtained:

(a) 5-(4-Methylthiophenyl)-3-(1-methyl-2-pyrrolidinyl) pyridine fumarate;
M.P. 133°–134° C. (EtOAc); $^1$H NMR (DMSO-$d_6$, 300 MHz): δ 8.81 (d, J=2 Hz, 1 H), 8.52 (d, J=2 Hz, 1 H), 8.26 (app. t, J=2 Hz, 1 H), 7.70 (d, J=8 Hz, 2 H), 7.38 (d, J=8 Hz, 2 H), 6.61 (s, 2 H), 3.42 (t, J=8 Hz, 1 H), 3.30 (app. t, J=8.5 Hz, 1 H), 2.53 (s, 3 H), 2.44 (q, J=8 Hz, 1 H), 2.26 (m, 1 H), 2.21 (s, 3 H), 1.7–2.0 (m, 3 H).

(b) 5-(3-Methylphenyl)-3-(1-methyl-2-pyrrolidinyl) pyridine fumarate;
M.P. 144.5°–145.5° C. (EtOAc); $^1$H NMR (DMSO-$d_6$, 300 MHz): δ 8.78 (d, J=2 Hz, 1 H), 8.52 (d, J=2 Hz, 1 H), 8.00 (t, J=2 Hz, 1 H), 7.55 (bs, 1 H), 7.52 (d, J=8 Hz, 1 H), 7.39 (t, J=8 Hz, 1 H), 7.25 (d, J=7.5 Hz, 1 H), 6.62 (s, 3 H), 3.37 (t, J=8 Hz, 1 H), 3.27 (app. t, J=8 Hz, 1 H), 2.40 (q, J=8.5 Hz, 1 H), 2.39 (s, 3 H), 2.26 (m, 1 H), 2.19 (s, 3 H), 1.7–2.0 (m, 3 H).

(c) 5-(3-Trifluoromethylphenyl)-3-(1-methyl-2-pyrrolidinyl) pyridine fumarate;
M.P. 157.5°–158.5° C. (EtOH); $^1$H NMR (DMSO-$d_6$, 300 MHz): δ 8.86 (d, J=2.5 Hz, 1 H), 8.60 (d, J=2 Hz, 1 H), 8.10 (m, 3 H), 7.78 (m, 2 H), 6.62 (s, 4 H), 3.43 (t, J=8 Hz, 1 H), 3.27 (dt, J=8, 2 Hz, 1 H), 2.41 (q, J=9 Hz, 1 H), 2.25 (m, 1 H), 2.20 (s, 3 H), 1.8–2.0 (m, 3 H).

(d) 5-(2-Methylphenyl)-3-(1-methyl-2-pyrrolidinyl) pyridine fumarate;
M.P. 141°–142° C. (EtOH-EtOAc); $^1$H NMR (DMSO-$d_6$, 300 MHz): δ 8.56 (d, J=2 Hz, 1 H), 8.50 (d, J=2 Hz, 1 H), 7.79 (t, J=2 Hz, 1 H), 7.29 (m, 4 H), 6.61 (s, 3 H), 3.51 (app. t, J=8 Hz, 1 H), 3.32 (d t, J=8, 2 Hz, 1 H), 2.49 (q, J=8.5 Hz, 1 H), 2.28 (m, 1 H), 2.26 (s, 3 H), 2.25 (s, 3 H), 1.8–1.9 (m, 3 H).

(e) 5-(2-Methoxyphenyl)-3-(1-methyl-2-pyrrolidinyl) pyridine fumarate;
M.P. 132°–133° C. (EtOAc); $^1$H NMR (DMSO-$d_6$, 300 MHz): δ 8.60 (d, J=2 Hz, 1 H), 8.48 (d, J=2 Hz, 1 H), 7.85 (t, J=2 Hz, 1 H), 7.38 (m, 2 H), 7.16 (d, J=8 Hz, 1 H), 7.07 (t, J=7.5 Hz, 1 H), 6.61 (s, 3 H), 3.79 (s, 3 H), 3.38 (t, J=8 Hz, 1 H), 3.27 (app. t, J=8.5 Hz, 1 H), 2.42 (q, J=9 Hz, 1 H), 2.25 (m, 1 H), 2.21 (s, 3 H), 1.7–1.9 (m, 3 H).

(f) 5-(4-Methoxyphenyl)-3-(1-methyl-2-pyrrolidinyl) pyridine fumarate;
M.P. 97°–98° C. (EtOH); $^1$H NMR ($CD_3OD$, 300 MHz): δ 8.67 (d, J=2 Hz, 1 H), 8.40 (d, J=2 Hz, 1 H), 8.14 (t, J=3 Hz, 1 H), 7.45 (bd, J=9 Hz, 2 H), 6.86 (bd, J=9 Hz, 2 H), 6.51 (s, 4 H), 4.25 (q, J=6 Hz, 1 H), 3.70 (m, 1 H), 3.64 (s, 3 H), 3.12 (m, 1 H), 2.58 (s, 3 H), 2.0–2.4 (m, 4 H).

(g) 5-(4-Phenoxyphenyl)-3-(1-methyl-2-pyrrolidinyl) pyridine fumarate;
M.P. 126°–128° C. (EtOAc); $^1$H NMR ($CD_3OD$, 300 MHz): δ 8.79 (d, J=2 Hz, 1 H), 8.54 (d, J=3 Hz, 1 H), 8.26 (t, J=3 Hz, 1 H), 7.61 (bd, J=9 Hz, 2 H), 7.28 (app. t, J=9 Hz, 2 H), 6.9–7.1 (m, 5 H), 6.60 (s, 4 H), 4.34 (dd, J=12, 9 Hz, 1 H), 3.79 (m, 1 H), 3.20 (m, 1 H), 2.51 (s, 3 H), 2.3–2.5 (m, 2 H), 2.1–2.3 (m, 2 H).

(h) 5-(3,4-Methylenedioxyphenyl)-3-(1-methyl-2-pyrrolidinyl)pyridine fumarate;
M.P. 168°–170° C. (EtOH); $^1$H NMR ($CD_3OD$, 300 MHz): δ 8.71 (s, 1 H), 8.47 (s, 1 H), 8.15 (s, 1 H), 7.08 (m, 2 H), 6.82 (m, 1 H), 6.58 (s, 3 H), 5.90 (s, 2 H), 4.30 (app. t, J=7 Hz, 1 H), 3.75 (m, 1 H), 3.14 (m, 1 H), 2.63 (s, 3 H), 2.1–2.5 (m, 4 H).

(i) 5-(3,4-Difluorophenyl)-3-(1-methyl-2-pyrrolidinyl) pyridine fumarate;
M.P. 158°–160° C. (EtOH); $^1$H NMR ($CD_3OD$, 300 MHz): δ 8.61 (d, J=2 Hz, 1 H), 8.42 (d, J=2 Hz, 1 H), 8.12 (t, J=2 Hz, 1 H), 7.40 (m, 1 H), 7.28 (m, 1 H), 7.10 (m, 1 H), 6.60 (s, 2 H), 4.13 (app. t, J=7 Hz, 1 H), 3.64 (m, 1 H), 2.99 (m, 1 H), 2.49 (s, 3 H), 2.25 (m, 2 H), 2.03 (m, 2 H).

(j) 5-(2-Trifluoromethylphenyl)-3-(1-methyl-2-pyrrolidinyl)pyridine fumarate;
M.P. 141°–143° C. (EtOH); $^1$H NMR ($CD_3OD$, 300 MHz): δ 8.81 (d, J=3 Hz, 1 H), 8.62 (s, 1 H), 8.12 (s, 1 H), 7.88 (d, J=6 Hz, 1 H), 7.76 (t, J=7 Hz, 1 H), 7.67 (t, J=7 Hz, 1 H), 7.50 (d, J=6 Hz, 1 H), 6.69 (s, 3 H), 4.46 (dd, J=12, 7.5 Hz, 1 H), 3.86 (m, 1 H), 3.27 (m, 1 H), 2.77 (s, 3 H), 2.60 (m, 1 H), 2.2–2.5 (m, 3 H).

(k) 5-(4-Trifluoromethylphenyl)-3-(1-methyl-2-pyrrolidinyl)pyridine fumarate;
M.P. 159°–160° C. (EtOH); $^1$H NMR ($CD_3OD$, 300 MHz): δ 8.98 (d, J=2 Hz, 1 H), 8.74 (d, J=2 Hz, 1 H), 8.46 (t, J=2 Hz, 1 H), 7.93 (d, J=9 Hz, 2 H), 7.81 (d, J=9 Hz, 2 H), 6.67 (s, 3 H), 4.46 (dd, J=10.5, 7.5 Hz, 1 H), 3.90 (m, 1 H), 3.29 (m, 1 H), 2.77 (bs, 3 H), 2.60 (m, 1 H), 2.2–2.7 (m, 4 H).

(l) 5-(2-Naphthyl)-3-(1-methyl-2-pyrrolidinyl)pyridine fumarate;

M.P. 142°–145° C. (EtOH); $^1$H NMR (CD$_3$OD, 300 MHz): δ 8.95 (d, J=2 Hz, 1 H), 8.58 (d, J=2 Hz, 1 H), 8.35 (t, J=2 Hz, 1 H), 8.14 (bs, 1 H), 7.7–8.0 (m, 4 H), 7.45 (m, 2 H), 6.62 (s, 3 H), 4.24 (dd, J=10, 7.5 Hz, 1 H), 3.70 (m, 1 H), 3.09 (m, 1 H), 2.63 (s, 3 H), 2.48 0 (m, 1 H), 2.1–2.4 (m, 3 H).

(m) 5-(4-Biphenyl)-3-(1-methyl-2-pyrrolidinyl)pyridine fumarate;

M.P. 193°–194° C. (EtOH); $^1$H NMR (DMSO-d$_6$, 300 MHz): δ 8.89 (s, 1 H), 8.57 (s, 1 H), 8.12 (s, 1 H), 7.84 (dd, J=15, 9 Hz, 4 H), 7.74 (d, J=9 Hz, 2 H), 7.50 (app. t, J=9 Hz, 2 H), 7.40 (app. t, J=9 Hz, 1 H), 6.63 (s, 2 H), 3.48 (app. t, J=9, Hz, 1 H), 3.34 (app. t, J=9, Hz, 1 H), 2.5 (m, 1 H), 2.30 (m, 1 H), 2.25 (s, 3 H), 1.75–2.05 (m, 3 H).

EXAMPLE 12

5-(4-Methylphenyl)-3-(1-methyl-2-pyrrolidinyl) pyridine fumarate

5-Bromo-3-(1-methyl-2-pyrrolidinyl)pyridine (1.2 g, 5 mmol) and bis(triphenylphosphine)palladium(II) chloride (175 mg, 0.25 mmol) were stirred in anhydrous THF (10 mL) at 25° C. under inert atmosphere. p-Tolylmagnesium bromide (10 mL of a 1M solution in diethyl ether, 10 mmol) was added and the reaction mixture was stirred at 25° C. for 18 h.

The reaction mixture was filtered through celite, methanol (10 mL) was added and the solvents removed in vacuo. Concentrated HCl (10 mL) in water (50 mL) was added to the residue and this was washed with hexane (2×30 mL). The aqueous phase was carefully basified (Na$_2$CO$_3$) and extracted with ethyl acetate (3×30 mL). The combined organic extracts were washed with water (10 mL), brine (10 mL), dried (Na$_2$SO$_4$) and concentrated.

The resulting oil was dissolved in methanol (50 mL) and filtered through paper to remove residual solid catalyst. The filtrate was concentrated under reduced pressure before purification using "flash" silica gel column chromatography with ethyl acetate:hexane (1:3, 1:2) as eluant to afford 5-(4-methylphenyl)-3-(1-methyl-2-pyrrolidinyl)pyridine, 740 mg, 59% as an oil. This was converted to the title compound by the addition of one equivalent of fumaric acid to a methanol (15 mL) solution of the free amine at 25° C. After 30 minutes the solvent was removed in vacuo and the residue pumped under high vacuum. Trituration with diethyl ether followed by recrystallization from ethyl acetate afforded 5-(4-methylphenyl)-3-(1-methyl-2-pyrrolidinyl) pyridine fumarate, (20%). A second crop of crystalline product was obtained from the mother liquors by recrystallization (40%). M.p. 155°–157° C. (EtOAc); $^1$H NMR (D$_2$O, 300 MHz): δ 8.79 (d, J=2 Hz, 1 H), 8.56 (d, J=2 Hz, 1 H), 8.18 (s, 1 H), 7.53 (d, J=8 Hz, 2 H), 7.29 (d, J=8 Hz, 2 H), 6.54 (s, 2 H), 4.45 (bm, 1 H), 3.81 (bm, 1 H), 3.31 (bm, 1 H), 2.72 (s, 3 H), 2.55 (m, 1 H), 2.2–2.4 (s, 3 H), (m, 6 H).

EXAMPLE 13

5-benzyl-3-(1-methyl-2-pyrrolidinyl)pyridine fumarate

Repeating the procedure of Example 12, but using benzylmagnesium chloride in place of p-tolylmagnesium bromide, 5-benzyl-3-(1-methyl-2-pyrrolidinyl)pyridine fumarate was obtained:

M.P. 151° C. (EtOAc); $^1$H NMR (DMSO-d$_6$, 300 MHz): δ 8.69 (s, 1 H), 8.39 (d, J=3 Hz, 1 H), 7.33 (m, 2 H), 7.21 (m, 4 H), 6.63 (s, 3 H), 4.10 (s, 2 H), 3.60 (t, J=7 Hz, 1 H), 3.27 (m, 1 H), 2.35 (q, J=8 Hz, 1 H), 2.10 (s, 3 H), 2.05 (m, 1 H), 1.80 (m, 3 H), 1.55 (m, 1 H).

EXAMPLE 14

5-(2-Furanyl)-3-(1-methyl-2-pyrrolidinyl)pyridine fumarate

To a stirred solution of furan (0.73 mL, 10 mmol) in anhydrous diethyl ether (10 mL) at −78° C. under inert atmosphere was slowly added t-butyllithium (5.9 mL of a 1.7M solution in pentane, 10 mmol). This was stirred at −78° C. for 2 h and zinc chloride (10 mL of a 1M solution in diethyl ether, 10 mmol) was added. The reaction mixture was stirred at −78° C. for 1.5 h and then allowed to warm to 25° C. before cannulation into a stirred solution of 5-bromo-3-(1-methyl-2-pyrrolidinyl)pyridine (964 mg, 4 mmol) and bis(triphenylphosphine)palladium(II) chloride (175 mg, 0.25 mmol) in anhydrous THF (20 mL) at 25° C. under inert atmosphere. The reaction mixture was stirred for 18 h before being poured into a saturated solution of potassium sodium tartrate (100 mL) and ethyl acetate (50 mL) was added.

The organic phase was separated and the aqueous phase washed with ethyl acetate (3×50 mL). The combined organic layers were washed with brine (40 mL), dried (Na$_2$SO$_4$) and the solvents removed in vacuo. The resulting oil was dissolved in methanol (50 mL) and filtered through paper to remove residual solid catalyst. The filtrate was concentrated under reduced pressure before purification using "flash" silica gel column chromatography with ethyl acetate:hexane (1:4, 1:2) as eluant to afford 5-(furanyl)-3-(1-methyl-2-pyrrolidinyl)pyridine, 734 mg, 80%.

The above-described pyridine derivative was converted to invention compound of Formula I by the addition of one equivalent of fumaric acid to a methanol (15 mL) solution of the free amine at 25° C. After 30 minutes the solvent was removed in vacuo and the residue pumped under high vacuum. Trituration with diethyl ether followed by recrystallization from ethyl acetate afforded 5-(2-furanyl)-3-(1-methyl-2-pyrrolidinyl)pyridine fumarate, (43%). M.p. 147°–148° C. (EtOAc); $^1$H NMR (DMSO-d$_6$, 300 MHz): δ 8.71 (s, 1 H), 8.29 (s, 1 H), 7.93 (bs, 1 H), 7.64(s, 1 H), 6.95 (d, J=3 Hz, 1 H), 6.46 (bm, 1 H), 6.42 (s, 3 H), 3.40 (m, 1 H), 3.20 (m, 1 H), 2.39 (m, 1 H), 2.08 (m, 4 H), 1.74 (m, 3 H).

EXAMPLE 15

5-(Trimethylsilyl)-3-(1-methyl-2-pyrrolidinyl) pyridine fumarate

To a stirred solution of 5-bromo-3-(1-methyl-2-pyrrolidinyl)pyridine (1.2 g, 5 mmol) in anhydrous diethylether (20 mL) at −78° C. under inert atmosphere was slowly added n-butyllithium (3.2 mL of a 1.6M solution in hexanes, 5 mmol). This was stirred at −78° C. for 30 minutes and chlorotrimethylsilane (0.63 mL, 5 mmol) was added. The reaction mixture was allowed to warm to 25° C. and stirred for 2 h under inert atmosphere. The reaction was quenched with a mixture of saturated NaHCO$_3$ solution (10 mL) and water (10 mL) and ethyl acetate (10 mL) was added.

The organic phase was separated and the aqueous phase washed with ethyl acetate (3×20 mL). The combined organic extracts were washed with brine (20 mL), dried (Na$_2$SO$_4$) and the solvents removed in vacuo. Purification was accomplished using "flash" silica gel column chromatography twice with ethyl acetate:hexane (1:3, 1:2) as eluant to afford 5-(trimethylsilyl)-3-(1-methyl-2-pyrrolidinyl) pyridine, 385 mg, 33% as an oil.

The above-described pyridine derivative was converted into invention compound of Formula I by the addition of one equivalent of fumaric acid to a methanol (5 mL) solution of the free amine at 25° C. After 30 minutes the solvent was removed in vacuo and the residue pumped under high vacuum. Trituration with diethyl ether followed by recrystallization from ethyl acetate afforded 5-trimethylsilyl-3-(1-methyl-2-pyrrolidinyl)pyridine fumarate, (51%). M.p. 161°–162° C. (EtOAc); $^1$H NMR (D$_2$O, 300 MHz): δ 8.48 (s, 2 H), 8.26 (s, 1 H), 6.25 (s, 3 H), 4.24 (bm, 1 H), 3.53 (bm, 1 H), 3.03 (bm, 1 H), 2.43 (s, 3 H), 2.27 (m, 1 H), 1.9–2.1 (m, 3 H), 0.0 (s, 9 H).

EXAMPLE 16

5-Phenylethynyl-3-(1-methyl-2-pyrrolidinyl)pyridine fumarate

Phenylacetylene (2.2 mL, 20 mmol) was added to a stirred solution of 5-bromo-3-(1-methyl-2-pyrrolidinyl) pyridine (2.17 g, 9 mmol), bis(triphenylphosphine) palladium(II) chloride (700 mg, 1 mmol), copper(I)iodide (380 mg, 2 mmol) and triethylamine (5.6 mL, 40 mmol) in anhydrous THF (20 mL) at 25° C. under inert atmosphere. The reaction mixture was stirred for 6 days before ethyl acetate (50 mL) was added and the mixture poured into water (50 mL).

The organic phase was separated and the aqueous layer extracted with isopropyl acetate (3×50 mL). The combined organic extracts were washed with brine (50 mL), dried (MgSO$_4$) and filtered through celite before the solvents were removed in vacuo. The dark residue was extracted several times with methanol and the combined extracts concentrated in vacuo. The resulting oil was purified using "flash" silica gel column chromatography with ethyl acetate:hexane (1:9, 1:4) as eluant to afford 5-phenylethynyl-3-(1-methyl-2-pyrrolidinyl)pyridine, 1.22 g, 52%.

The above-described pyridine derivative was converted into invention compound of Formula I by the addition of one equivalent of fumaric acid to a methanol (10 mL) solution of the free amine at 25° C. After 30 minutes the solvent was removed in vacuo and the residue pumped under high vacuum. Trituration with diethyl ether followed by recrystallization from isopropyl acetate afforded 5-(phenylethynyl)-3-(1-methyl-2-pyrrolidinyl)pyridine fumarate, (56%). M.p. 152°–154° C. (decorap., iPrOAc); $^1$H NMR (DMSO-d$_6$, 300 MHz): δ 9.6–10.4 (bs, 1 H), 8.5–8.9 (bs, 1 H), 8.00 (s, 1 H), 7.60(m, 2 H), 7.46 (m, 3 H), 6.63 (s, 3 H), 3.51 (app. t, J=8 Hz, 1 H), 3.33 (app. t, J=8 Hz, 1 H), 2.51 (m, 1 H), 2.24 (s, 3 H), 2.19–2.32 (m, 1 H), 1.7–2.0 (m, 3 H).

EXAMPLE 17

5-Ethynyl-3-(1-methyl-2-pyrrolidinyl)pyridine fumarate

Repeating the procedure of Example 16, but using trimethylsilylacetylene in place of phenylacetylene, 5-ethynyl-3-(1-methyl-2-pyrrolidinyl)pyridine and the fumarate derivative thereof were obtained as follows: 5-Trimethylsilylethynyl-3-(1-methyl-2-pyrrolidinyl) pyridine (516 mg, 2 mmol) and cesium carbonate (200 mg, 0.6 mmol) were dissolved in methanol (10 mL) and heated under reflux for 5 h. After cooling the solvents were removed in vacuo and the residue dissolved in ethyl acetate (40 mL) and washed with water (10 mL). The aqueous layer was extracted with ethyl acetate (40 mL) and the combined organic extracts washed with brine (10 mL), dried (Na$_2$SO$_4$) and concentrated in vacuo. The crude product was chromatographed on "flash" silica gel with ethyl acetate:hexane (1:9, 1:4, 1,3) to afford 5-ethynyl-3-(1-methyl-2-pyrrolidinyl)pyridine as an oil, 218 mg, 59%.

$^1$H NMR (CDCl$_3$, 300 MHz): δ 8.58 (d, J=2 Hz, 1 H), 8.48 (d, J=2 Hz, 1 H), 7.80 (app. t, J=2 Hz, 1 H), 3.23 (t, J=8 Hz, 1 H), 3.18 (s, 1 H), 3.08 (app. t, J=8.5 Hz, 1 H), 2.30 (dd, J=18, 9 Hz, 1 H), 2.21 (m, 1 H), 2.16 (s, 3 H), 1.65–2.00 (m, 3 H).

5-Ethynyl-3-(1-methyl-2-pyrrolidinyl)pyridine fumarate:

M.P. 148°–149° C. (EtOH/EtOAc); $^1$H NMR (DMSO-d$_6$, 300 MHz): δ 8.57 (d, J=2 Hz, 1 H), 8.54 (d, J=2 Hz, 1 H), 7.83 (app. t, J=2 Hz, 1 H), 6.61 (s, 2 H), 4.44 (s, 1 H), 3.25 (app. dd, J=16, 8 Hz, 1 H), 3.19 (dd, J=8, 3 Hz, 1 H), 2.33 (app. dd, J=16, 8 Hz, 1 H), 2.20 (m, 1 H), 2.12 (s, 3 H), 1.6–1.9 (m, 3 H).

EXAMPLE 18

4-Bromophenyl-tert-butyldimethylsilyl ether

4-Bromophenol (5.76 g, 30 mmol), imidazole (4.08 g, 60 mmol) and tert-butyldimethylsilyl chloride (5.02 g, 33 mmol) were stirred in anhydrous DMF (100 mL) at 25° C. for 18 h. The reaction mixture was then poured into water (100 mL) and extracted with ethyl acetate (2×75 mL). The combined extracts were washed with water (2×75 mL), brine (75 mL) and dried (MgSO$_4$) before concentration in vacuo. The crude product was purified using "flash" silica gel column chromatography with ethyl acetate:hexane (1:4) as eluant to afford the title compound as an oil, 7.9 g, 92%. $^1$H NMR (CDCl$_3$, 300 MHz): δ 7.33 (app. dt, J=9, 3, 1 Hz, 2 H), 6.73 (app. dt, J=9, 3, 1 Hz, 2 H) 0.98 (s, 9 H),0.21 (s, 6 H).

EXAMPLE 19

4-Bromo-3-halophenyl-tert-butyldimethylsilyl ethers

Repeating the procedure of Example 18, but using the appropriate starting materials in place of 4-bromophenol, the following compounds were obtained:

(a) 4-Bromo-3-chlorophenyl-tert-butyldimethylsilyl ether $^1$H NMR (CDCl$_3$, 300 MHz): δ 7.47 (d, J=2 Hz, 1 H), 7.24 (dd, J=9, 2 Hz, 1 H), 6.75 (d, J=9 Hz, 1 H), 1.02 (s, 9 H), 0.22 (s, 6 H).

(b) 4-Bromo-3-fluorophenyl-tert-butyldimethylsilyl ether $^1$H NMR (CDCl$_3$, 300 MHz): δ 7.61 (m, 1 H), 7.31 (m, 1 H), 6.91 (m, 1 H), 1.01 (s, 9 H), 0.23 (s, 6 H).

EXAMPLE 20

5-(4-Hydroxyphenyl)-3-(1-methyl-2-pyrrolidinyl) pyridine fumarate

To a stirred solution of 4-bromophenyl-tert-butyldimethylsilyl ether (2.87 g, 10 mmol) in anhydrous diethyl ether (10 mL) at –78° C. under inert atmosphere was slowly added t-butyllithium (11.75 mL of a 1.7M solution in pentane, 20 mmol). This was stirred at –78° C. for 30 minutes and zinc chloride (10 mL of a 1M solution in diethyl ether, 10 mmol) was added. The mixture was allowed to warm to 25° C. over 30 minutes before being cannulated into a stirred solution of 5-bromo-3-(1-methyl-2-pyrrolidinyl) pyridine (1 g, 4.16 mmol) and bis(triphenylphosphine) palladium(II) chloride (175 mg, 0.25 mmol) in anhydrous THF (10 mL) at 25° C. under inert atmosphere. The reaction mixture was stirred for 18 h before being poured into a saturated solution of potassium sodium tartrate (50 mL).

The solids were removed by filtration, the organic phase separated and the aqueous phase washed with ethyl acetate (2×100 mL). The combined organic layers were washed with brine (50 mL), dried ($MgSO_4$) and the solvents removed in vacuo. The resulting oil was dissolved in methanol (50 mL) and filtered through paper to remove residual solid catalyst. The filtrate was concentrated under reduced pressure before purification using "flash" silica gel column chromatography with ethyl acetate:hexane (1:4, 1:3, 1:1) as eluant to afford 5-(4-tert-butyldimethylsilyloxyphenyl)-3-(1-methyl-2-pyrrolidinyl)pyridine, 890 mg, 58% as an oil.

The above-described pyridine derivative (750 mg, 2.04 mmol) was dissolved in methanol (40 mL) and cesium fluoride (620 mg, 4.08 mmol) was added. The stirred mixture was heated at reflux for 18 h under inert atmosphere. After cooling the solvent was removed in vacuo and the resulting oil was dissolved in ethyl acetate (50 mL). This was washed with water (20 mL), brine (20 mL), dried ($MgSO_4$) and concentrated. The crude material was chromatographed on "flash" silica gel with ethyl acetate:hexane (1:2) to 10% methanol:ethyl acetate as eluant to afford 5-(4-hydroxyphenyl)-3-(1-methyl-2-pyrrolidinyl)pyridine 480 mg, 93% as a colorless foam, $^1$H NMR ($CDCl_3$, 300 MHz): δ 8.66 (d, J=2 Hz, 1 H), 8.43 (d, J=2 Hz, 1 H), 7.90 (s, 1 H), 7.32 (d, J=9 Hz, 2 H), 6.81 (d, J=9 Hz, 2 H), 3.33 (t, J=8 Hz, 1 H), 3.22 (t, J=8 Hz, 1 H), 2.41 (m, 1 H), 2.28 (s, 3 H), 2.10 (m, 2 H), 1.93 (m, 2 H).

The above-described pyridine derivative was converted into invention compound of Formula I by the addition of one equivalent of fumaric acid to a methanol (15 mL) solution of the free amine at 25° C. After 30 minutes the solvent was removed in vacuo and the residue pumped under high vacuum. Trituration with diethyl ether followed by recrystallization from ethyl acetate afforded 5-(4-hydroxyphenyl)-3-(1-methyl-2-pyrrolidinyl)pyridine fumarate, (46%). M.p. 136°–137° C. (EtOAc); $^1$H NMR (DMSO-$d_6$, 300 MHz): δ 8.76 (s, 1 H), 8.47 (s, 1 H), 8.00 (s, 1 H), 7.58 (d, J=6 Hz, 2 H), 6.90 (d, J=6 Hz, 2 H), 6.62 (s, 2 H), 3.53 (m, 1 H), 3.37 (m, 1 H), 2.55 (m, 1 H), 2.30 (s, 3 H), 1.9 (m, 4 H).

EXAMPLE 21

5-(4-Hydroxy-3-halophenyl)-3-(1-methyl-2-pyrrolidinyl)pyridine fumarates

Repeating the procedure of Example 20, but using the appropriate starting materials in place of 4-bromophenyl-tert-butyldimethylsilyl ether, the following compounds were obtained:

(a) 5-(4-Hydroxy-3-chlorophenyl)-3-(1-methyl-2-pyrrolidinyl)pyridine $^1$H NMR ($CDCl_3$, 300 MHz): δ 8.62 (d, J=2 Hz, 1 H), 8.41 (d, J=2 Hz, 1 H), 7.92 (t, J=2 Hz, 1 H), 7.60 (d, J=3 Hz, 1 H), 7.37 (dd, J=9, 3 Hz, 1 H), 7.03 (d, J=9 Hz, 1 H) 4.10 (s, 1 H), 3.29 (t, J=8 Hz, 1 H), 3.20 (t, J=8 Hz, 1 H), 2.35 (m, 1 H), 2.23 (s, 3 H), 2.03 (m, 1 H), 1.87 (m, 3 H);

5-(4-hydroxy-3-chlorophenyl)-3-(1-methyl-2-pyrrolidinyl) pyridine fumarate;

M.P. 199°–201° C. (decomp., EtOAc); $^1$H NMR (DMSO-$d_6$, 300 MHz): δ 8.81 (d, J=2 Hz, 1 H), 8.52 (s, 1 H), 8.08 (s, 1 H), 7.77 (d, J=2 Hz, 1 H), 7.57 (dd, J=5, 2 Hz, 1 H), 7.12 (d, J=8 Hz, 1 H), 6.62 (s, 2 H), 3.65 (t, J=7 Hz, 1 H), 3.42 (t, J=5 Hz, 1 H), 2.59 (m, 1 H), 2.30 (s, 3 H), 1.95 (m, 4 H).

(b) 5-(4-Hydroxy-3-fluorophenyl)-3-(1-methyl-2-pyrrolidinyl)pyridine, $^1$H NMR ($CDCl_3$, 300 MHz): δ 8.65 (d, J=2 Hz, 1 H), 8.44 (d, J=2 Hz, 1 H), 7.81 (t, J=2 Hz, 1 H), 7.16 (m, 1 H), 7.10 (m, 1 H), 6.90 (t, J=9 Hz, 1 H), 3.36 (t, J=9 Hz, 1 H), 3.22 (t, J=9 Hz, 1 H), 2.40 (dd, J=12, 6 Hz, 1 H), 2.31 (m, 1 H), 2.26 (s, 3 H), 2.11 (m, 1 H), 1.93 (m, 2 H);

5-(4-hydroxy-3-fluorophenyl)-3-(1-methyl-2-pyrrolidinyl) pyridine fumarate;

M.P. 192°–193° C. (EtOH); $^1$H NMR ($CD_3OD$, 300 MHz): δ 8.66 (d, J=3 Hz, 1 H), 8.42 (d, J=3 Hz, 1 H), 8.13 (t, J=3 Hz, 1 H), 7.32 (m, 1 H), 7.19 (m, 1 H), 6.86 (t, J=9 Hz, 1 H), 6.49 (s, 2 H), 4.18 (t, J=10, 9 Hz, 1 H), 3.67 (m, 1 H), 3.03 (m, 1 H), 2.55 (s, 3 H), 2.05–2.45 (m, 4 H).

EXAMPLE 22

5-(4-Fluorophenyl)-3-(2-piperidinyl)pyridine fumarate

To a stirred solution of 4-bromofluorobenzene (1.75 g, 10 mmol) in anhydrous diethyl ether (5 mL) at −10° C. under inert atmosphere was slowly added n-butyllithium (6.25 mL of a 1.6M solution in hexanes, 10 mmol). This was stirred at −10° C. for 30 minutes and zinc chloride (10 mL of a 1M solution in diethyl ether, 10 mmol) was added. The mixture was allowed to warm to 25° C. over 30 minutes before being cannulated into a stirred solution of 5-bromo-3-(2-N-t-butoxycarbonylpiperidinyl)pyridine (1.53 g, 4.5 mmol) and bis(triphenylphosphine) palladium(II) chloride (175 mg, 0.25 mmol) in anhydrous THF (15 mL) at 0° C. under inert atmosphere. The reaction mixture was then stirred at 25° C. for 18 h before being poured into a saturated solution of potassium sodium tartrate (100 mL) and ethyl acetate (50 mL).

The organic phase was separated and the aqueous phase washed with ethyl acetate (2×50 mL). The combined organic layers were washed with saturated sodium carbonate solution (40 mL), brine (50 mL), dried ($Na_2SO_4$) and the solvents removed in vacuo. The resulting oil was dissolved in methanol (50 mL) and filtered through paper to remove residual solid catalyst. The filtrate was concentrated under reduced pressure before purification using "flash" silica gel column chromatography with ethyl acetate:hexane (1:9, 1:4) as eluant to afford 5-(4-fluorophenyl)-3-(2-N-tert-butoxycarbonylpiperidinyl) pyridine, 1.45 g, 90% as an oil.

The above-described pyridine derivative (1.25 g, 3.5 mmol) was dissolved in a mixture of dichloromethane (10 mL) and trifluoroacetic acid (10 mL) and this was stirred at 25° C. for 18 h. The solvents were removed in vacuo and the crude material dissolved in ethyl acetate (50 mL). Saturated sodium carbonate solution (30 mL) was added and the organic layer separated. The aqueous phase was extracted with two further portions of ethyl acetate (2×30 mL), the combined organic extracts washed with brine (20 mL), dried ($Na_2SO_4$) and concentrated in vacuo. The residue was chromatographed on silica gel with ethyl acetate, then methanol:ethyl acetate (1:9) as eluant to afford 5-(4-fluorophenyl)-3-(2-piperidinyl)pyridine, 940 mg, 100%. $^1$H NMR ($CDCl_3$, 300 MHz): δ 8.69 (d, J=2 Hz, 1 H), 8.55 (d, J=2 Hz, 1 H), 7.93 (t, J=2 Hz, 1 H), 7.56 (m, 2 H), 7.16 (app.

tm, J=9 Hz, 2 H), 3.18 (d, J=12 Hz, 1 H), 2.83 (td, J=12, 3 Hz, 1 H), 2.61 (bs exch., 1 H), 1.92 (m, 2 H), 1.45–1.75 (m, 6 H).

The above described pyridine derivative was converted into invention compound of Formula I by the addition of one equivalent of fumaric acid to a methanol (15 mL) solution of the free amine at 25° C. After 30 minutes the solvent was removed in vacuo and the residue pumped under high vacuum. Trituration with diethyl ether resulted in the formation of 5-(4-fluorophenyl)-3-(2-piperidinyl)pyridine fumarate (70%) as a colorless solid. M.p. 209°–210° C. (decomp., Et$_2$O); $^1$H NMR (DMSO-d$_6$, 300 MHz): δ 8.86 (s, 1 H), 8.63 (s, 1 H), 8.32 (s, 1 H), 7.81 (dd, J=8, 5 Hz, 2 H), 7.32 (app. t, J=8 Hz, 2 H), 6.49 (s, 2 H), 4.24 (dd, J=10, 4 Hz, 1 H), 3.37 (d, J=12 Hz, 1 H), 2.97 (m, 1 H), 1.5–2.1 (m, 6 H).

EXAMPLE 23

5-[3-(1-Hydroxy-2-propynyl)]-3-(1-methyl-2-pyrrolidinyl)pyridine fumarate

A mixture of 5-bromo-3-(1-methyl-2-pyrrolidinyl)pyridine (1 g, 4.15 mmol), 10% palladium on charcoal (106 mg, 0.1 mmol), copper(I)iodide (38 mg, 0.2 mmol), triphenylphosphine (104 mg, 0.4 mmol) and potassium carbonate (1.38 g, 10 mmol) in DME (10 mL) and water (10 mL) was stirred at 25° C. After 0.5 h, propargyl alcohol (0.58 mL, 10 mmol) was added and the reaction flask was heated at 80° C. for 18 h. The cooled mixture was then filtered through celite and the filtrate concentrated in vacuo. The mixture was then acidified with 1M HCl (50 mL) and extracted with toluene (50 mL). The aqueous layer was made basic with solid potassium carbonate and extracted with ethyl acetate (2×100 mL). The combined ethyl acetate extracts were washed with water (50 mL), dried (MgSO$_4$) and concentrated to afford an oil (858 mg, 96%). The crude product was purified by silica gel column chromatography with ethyl acetate:hexane (1:1) to ethyl acetate as eluants to afford 5-(2-propyn-1-ol)-3-(1-methyl-2-pyrrolidinyl)pyridine (660 mg, 73%). This was converted to the title compound by the addition of one equivalent of fumaric acid to a methanol (10 mL) solution of the free amine at 25° C. After 30 minutes the solvent was removed in vacuo and the residue pumped under high vacuum. Trituration with diethyl ether followed by recrystallization from ethyl acetate afforded 5-[3-(1-hydroxy-2-propynyl)]-3-(1-methyl-2-pyrrolidinyl)pyridine fumarate, (96%). M.p. 167°–168° C. (EtOAc); $^1$H NMR (DMSO-d$_6$, 300 MHz): δ 8.52 (m, 2H), 7.80 (app t, J=2 Hz, $^1$H), 6.61 (s, 2H), 4.43 (s, 2H), 3.31 (app. t, J=8 Hz, $^1$H), 3.23 (td, J=8, 2 Hz, $^1$H), 2.37 (dd, J=9, 7.5 Hz, 1H), 2.20 (m, 1H), 2.15 (s, 3H), 1.84 (m, 2H), 1.66 (m, 1H).

EXAMPLE 24

Repeating the procedure of Example 23, but using the appropriate substituted acetylene in place of propargyl alcohol the following compounds were obtained:

(a) 5-[4-(2-Hydroxy-3-butynyl)]-3-(1-methyl-2-pyrrolidinyl)pyridine fumarate.

M.p. 132°–133° C. (EtOH); $^1$H NMR (DMSO-d$_6$, 300 MHz): δ 8.49 (s, 2H), 7.77 (s, 1H), 6.60 (s, 2H), 4.41 (app. dd, J=14, 7 Hz, 1H), 3.29 (app. t, J=8 Hz, 1H), 3.22 (td, J=9, 2 Hz, 1H), 2.35 (app. dd, J=9, 9 Hz, 1H), 2.20 (m, 1H), 2.13 (s, 3H), 1.82 (m, 2H), 1.67 (m, 1H), 1.38 (d, J=7 Hz, 3H).

(b) 5-[4-(1-Hydroxy-3-butynyl)]-3-(1-methyl-2-pyrrolidinyl)pyridine fumarate.

M.p. 145°–147° C. (EtOH); $^1$H NMR (DMSO-d$_6$, 300 MHz): δ 8.50 (s, 1H), 8.48 (s, 1H), 7.79 (s, 1H), 6.60 (s, 3H), 3.59 (t, J=7 Hz, 2H), 3.37 (app. t, J=8 Hz, 1H), 3.26 (td, J=9, 2 Hz, 1H), 2.58 (t, J=7 Hz, 2H), 2.42 (app. dd, J=9, 9 Hz, 1H), 2.23 (m, 1H), 2.17 (s, 3H), 1.84 (m, 2H), 1.68 (m, 1H).

(c) 5-[1-(1-Pentynyl)]-3-(1-methyl-2-pyrrolidinyl)pyridine fumarate.

M.p. 105°–107° C. (EtOAc); $^1$H NMR (DMSO-d$_6$, 300 MHz): δ 8.53 (m, 2H), 7.83 (s, 1H), 6.64 (bs, 2H), 3.43 (app. t, J=9 Hz, 1H), 3.32 (app. t, J=8 Hz, 1H), 2.47 (m 3H), 2.25 (m, 1H), 2.23 (s, 3H), 1.92 (m, 2H), 1.75 (m, 1H), 1.60 (m, 2H), 1.03 (t, J=8 HZ, 3H).

(d) 5-[4-(2-Hydroxy-2-methyl-3-butynyl)]-3-(1-methyl-2-pyrrolidinyl)pyridine fumarate.

M.p. 143°–144° C. (EtOAc); $^1$H NMR (DMSO-d$_6$, 300 MHz): δ 8.56 (b, 2H), 7.81 (s, 1H), 6.64 (s, 2H), 3.39 (app. t, J=8 Hz, 1H), 3.27 (td, J=7, 2 Hz, 1H), 2.44 (app. dd, J=8, 8 Hz, 1H), 2.24 (m, 1H), 2.18 (s, 3H), 1.84 (m, 2H), 1.71 (m, 1H), 1.48 (s, 6H).

(e) 5-[3-(1-Dimethylamino-2-propynyl)]-3-(1-methyl-2-pyrrolidinyl)pyridine fumarate.

M.p. 167°–168° C. (EtOAc); $^1$H NMR (DMSO-d$_6$, 300 MHz): δ 8.54 (s, 1H), 8.50 (s, 1H), 7.80 (s, 1H), 6.60 (s, 3H), 3.57 (s, 2H), 3.25 (m, 1H), 3.20 (m, 1H), 2.34 (m, 1H), 2.30 (s, 6H), 2.20 (s, 3H), 2.13 (s, 3H), 1.83 (m, 2H), 1.62 (m, 1H).

(f) 5-[3-(1-Methoxy-2-propynyl)]-3-(1-methyl-2-pyrrolidinyl)pyridine fumarate

M.p. 116°–118° C. (EtOAc); $^1$H NMR (DMSO-d$_6$, 300 MHz): δ 8.57 (d, J=2 Hz, 1H), 8.54 (d, J=2 Hz, 1H), 7.85 (m, 1H), 6.62 (s, 3H), 4.36 (s, 2H), 3.35 (s, 3H), 3.30 (m, 1H), 3.23 (b-td, J=8, 2.5 Hz, 1H), 2.38 (dd, J=9, 9 Hz, 1H), 2.21 (m, 1H), 2.15 (s, 3H), 1.84 (m, 2H), 1.69 (m, 1H).

EXAMPLE 25

5-[1-(1-Propynyl)]-3-(1-methyl-2-pyrrolidinyl)pyridine fumarate

A Parr hydrogenation vessel was charged with 5-bromo-3-(1-methyl-2-pyrrolidinyl)pyridine (1 g, 4.15 mmol), 10% palladium on charcoal (106 mg, 0.1 mmol), copper(I)iodide (38 mg, 0.2 mmol), triphenylphosphine (104 mg, 0.4 mmol) and potassium carbonate (1.38 g, 10 mmol), DME (10 mL) and water (10 mL). The vessel was evacuated and propyne gas was introduced to a pressure of 20 p.s.i. The mixture was agitated and heated at 90° C. for 6 days, readmitting propyne gas as necessary. Analysis by GC at this stage indicated about 40% completion and the cooled mixture was filtered through celite and the filtrate concentrated in vacuo. The mixture was then acidified with 1M HCl (50 mL) and extracted with toluene (50 mL). The aqueous layer was made basic with solid potassium carbonate and extracted with ethyl acetate (2×100 mL). The combined ethyl acetate extracts were washed with water (50 mL), dried (MgSO$_4$) and concentrated to afford an oil. The crude product was purified by silica gel column chromatography with ethyl acetate:hexane (1:1) as eluant to afford 5-propynyl-3-(1-methyl-2-pyrrolidinyl)pyridine (250 mg, 30%). A portion (225 mg) of this material was converted to the title compound by the addition of one equivalent of fumaric acid to a methanol (10 mL) solution of the free amine at 25° C. After 30 minutes the solvent was removed in vacuo and the residue pumped under high vacuum. Trituration with diethyl ether followed by recrystallization from ethyl acetate afforded 5-[1-(1-propynyl)]-3-(1-methyl-2-pyrrolidinyl) pyridine fumarate, 180 mg, 50%. M.p. 188°–189° C. (EtOAc); $^1$H NMR (DMSO-d$_6$, 300 MHz): δ 8.49 (s, 1H), 8.47 (s, 1H), 7.77 (s, 1H), 6.60 (s, 2H), 3.34 (t, J=9 Hz, 1H), 3.25 (app. t, J=9 Hz, 1H), 2.41 (dd, J=9, 9 Hz, 1H), 2.22 (m, 1H), 2.16 (s, 3H), 2.08 (s, 3H), 1.85 (m, 2H), 1.69 (m, 1H).

EXAMPLE 26

5-Bromo-3-(1-tert-butyloxycarbonyl-2-pyrrolidinyl) pyridine

5-Bromo-3-(1-H-pyrrolidinyl)pyridine (4.54 g, 20 mmol), di-tert-butyl dicarbonate (4.80 g, 22 mmol) and triethylamine (3.1 mL, 22 mmol) were dissolved in methylene chloride (50 mL) and stirred at 0° C. under a drying tube. 4-Dimethylaminopyridine (122 mg, 1 mmol) was added and the mixture was stirred at 25° C. for 18 h. The mixture was concentrated in vacuo, then water (20 mL) and methylene chloride (20 mL) were added. The organic phase was separated and the aqueous layer washed with methylene chloride (2×20 mL). The combined organic extracts were washed with brine (20 mL) and dried (MgSO$_4$). The solvents were removed in vacuo and the residue chromatographed on "flash" silica gel with ethyl acetate:hexane (1:9 to 1:4) as eluants to afford the title compound as an oil, 3.38 g, 52%. $^1$H NMR (CDCl$_3$, 300 MHz): δ 8.55 (b-s, 1H), 8.39 (d, J=2 Hz, 1H), 7.64 (b-s, 1H), 4.92 (b-m, 0.5H), 4.76 (b-m, 0.5H), 3.5–3.7 (b-m, 2H), 2.39 (b-m, 1H), 1.75–2.0 (m, 3H), 1.46 (s, 3H), 1.22 (s, 6H).

EXAMPLE 27

5-[4-(2-Hydroxy-2-methyl-3-butynyl)]-3-(1-tert-butyloxycarbonyl-2-pyrrolidinyl)pyridine A mixture of 5-bromo-3-(1-tert-butyloxycarbonyl-2-pyrrolidinyl)pyridine (1 g, 3.06 mmol), 10% palladium on charcoal (80 mg, 0.077 mmol), copper(I)iodide (58 mg, 0.30 mmol), triphenylphosphine (80 mg, 0.30 mmol) and potassium carbonate (1.06 g, 7.65 mmol) in DME (5 mL) and water (5 mL) was stirred at 25° C. After 0.75 h 2-methyl-3-butyn-2-ol (0.74 mL, 7.65 mmol) was added and the reaction flask was heated at 80° C. for 18 h. Water (30 mL) and ethyl acetate (30 mL) were added to the cooled mixture and this was filtered through celite. The organic phase was separated and the aqueous layer extracted with ethyl acetate (3×20 mL) and the combined ethyl acetate extracts were washed with brine (20 mL), dried (MgSO$_4$) and concentrated in vacuo. The crude product was purified by silica gel column chromatography with ethyl acetate:hexane (1:3 to 1:1) as eluants to afford 5-(2-hydroxy-2-methyl-3-butynyl)-3-(1-tert-butyloxycarbonyl-2-pyrrolidinyl)pyridine as an oil (772 mg, 76%). LRMS (EI) m/e 231 (M$^+$+H —CO$_2$ and isobutylene), 230 (M$^+$—CO$_2$ and isobutylene), 229 (M$^+$—CO$_2$tBu); $^1$H NMR (CDCl$_3$, 300 MHz): δ 8.56 (b-s, 1H), 8.37 (b-d, J=1.5 Hz, 1H), 7.53 (m, 1H), 4.93 (b-m, 0.5H), 4.76 (b-m, 0.5H), 3.5–3.7 (b-m, 2H), 2.36 (m, 1H), 1.75–2.0 (b-m, 3H), 1.72 (b-s, 1H), 1.63 (s, 6H), 1.45 (b-s, 3H), 1.21 (b-s, 6H).

EXAMPLE 28

5-Ethynyl-3-(1-tert-butyloxycarbonyl-2-pyrrolidinyl) pyridine 5-(2-Hydroxy-2-methyl-3-butynyl)-3-(1-tert-butyloxycarbonyl-2-pyrrolidinyl)pyridine (495 mg, 1.5 mmol) was dissolved in toluene (30 mL) and catalytic sodium hydride (10 mg) was added. The solution was heated until several milliliters of toluene-acetone mixture was removed by distillation. The mixture was cooled to 25° C. and water (20 mL) and ethyl acetate (40 mL) were added. The organic phase was separated and the aqueous layer extracted with ethyl acetate (2×40 mL) and the combined organic extracts were washed with brine (20 mL), dried (MgSO$_4$) and concentrated in vacuo. The crude product was purified by silica gel column chromatography with ethyl acetate:hexane (1:3) as eluant to afford 5-ethynyl-3-(1-tert-butyloxycarbonyl-2-pyrrolidinyl)pyridine as an oil (250 mg, 61%). LRMS (EI) m/e 217 (M$^+$+H—isobutylene), 216 (M$^+$—isobutylene); $^1$H NMR (CDCl$_3$, 300 MHz): δ 8.59 (b-s, 1H), 8.42 (d, J=1.5 Hz, 1H), 7.59 (b-s, 1H), 4.94 (b-m, 0.5H), 4.77 (b-m, 0.5H), 3.64 (b-m, 2H), 3.21 (s, 1H), 2.39 (m, 1H), 1.75–2.0 (b-m, 3H), 1.46 (s, 3H), 1.21 (s, 6H).

EXAMPLE 29

5-Ethynyl-3-(1-H-2-pyrrolidinyl)pyridine fumarate

5-Ethynyl-3-(1-tert-butyloxycarbonyl-2-pyrrolidinyl) pyridine (217 mg, 0.8 mmol) was dissolved in a mixture of methylene chloride (9 mL) and trifluoroacetic acid (6 mL). The solution was stirred for 3 h at 25° C. and then concentrated in vacuo. Methanol (20 mL) and solid potassium carbonate were added and the mixture was stirred, filtered and concentrated. Water (5 mL) and ammonium hydroxide (5 mL) were added and the aqueous phase was extracted with methylene chloride (5×10 mL). The organic extracts were washed with brine (10 mL), dried (MgSO$_4$) and concentrated to afford crude product (67 mg). The aqueous phase was concentrated in vacuo and extracted with methylene chloride (3×10 mL). The organic extracts were dried (MgSO$_4$), filtered and concentrated to afford a second crop of product (26 mg). The crude material was combined and purified by silica gel column chromatography with methanol:methylene chloride (1:19 to 1:9) as eluants to afford 5-ethynyl-3-(1-1H-2-pyrrolidinyl)pyridine as an oil (76 mg, 67%). This was converted to the title compound by the addition of one equivalent of fumaric acid to a methanol (5 mL) solution of the free amine at 25° C. After 30 minutes the solvent was removed in vacuo and the residue pumped under high vacuum. Trituration with diethyl ether followed by recrystallization from ethyl acetate afforded 5-ethynyl-3-(1-H-2-pyrrolidinyl)pyridine fumarate, (123 mg, 97%). M.p. 152°–153° C. (EtOAc); $^1$H NMR (DMSO-d$_6$, 300 MHz): δ 8.65 (d, J=2 Hz, 1H), 8.63 (d, J=2 Hz, 1H), 8.02 (t, J=2 Hz, 1H), 6.48 (s, 2H), 4.51 (s, 1H), 4.46 (app. t, J=8 Hz, 1H), 3.1–3.3 (m, 1H), 2.30 (m, 1H), 1.80–2.05 (m, 2H).

EXAMPLE 30

5-Bromo-3-(3,3-dibromo-1-methyl-5-pyrrolidin-2-onyl)pyridine

To a solution of 5-bromo-3-(1-methyl-2-pyrrolidinyl) pyridine (1.57 g, 6.5 mmol) in glacial acetic acid (12 mL) and water (3 mL) was added bromine (2 mL) dropwise at 25° C. Stirring was continued for 18 h and the solution was then heated at 85° C. for 2 h. Water (30 mL) was added to the cooled solution and the mixture was adjusted to pH 11 by the addition of solid potassium carbonate. Ethyl acetate (50 mL) was added and the organic phase was separated. The aqueous phase was extracted with ethyl acetate (2×20 mL) and the combined extracts were washed with brine (20 mL), dried (MgSO$_4$) and concentrated in vacuo. The crude material was chromatographed on silica gel with ethyl acetate:hexane (1:1) as eluant to afford the product as a solid (1.63 g, 60%). M.p. 139°–140° C.; $^1$H NMR (DMSO-$d_6$, 300 MHz): δ 8.73 (d, J=2 Hz, 1H), 8.63 (d, J=2 Hz, 1H), 8.20 (t, J=2 Hz, 1H), 4.84 (dd, J=7.5, 6 Hz, 1H), 3.56 (dd, J=15, 6 Hz, 1H), 3.04 (dd, J=15, 7.5 Hz, 1H), 2.64 (s, 3H).

EXAMPLE 31

5-Bromo-3-(1-methyl-5-pyrrolidin-2-onyl)pyridine

Sodium borohydride (862 mg, 22.8 mmol) was dissolved in ethanol (20 mL) and tellurium metal powder (1.45 g, 11.4 mmol) was added in portions. The mixture was heated under reflux for 0.25 h and 5-bromo-3-(3,3-dibromo-1-methyl-5-pyrrolidin-2-onyl)pyridine (775 mg, 1.9 mmol) was added to the solution at 25° C. After stirring for 2 h, ethyl acetate (50 mL) was added and the solution was filtered through Celite and concentrated in vacuo. 1M HCl (10 mL) was added to the residue and the solution was adjusted to pH 11 with solid potassium carbonate. After extraction with ethyl acetate (50 mL) the organic phase was separated. The aqueous phase was extracted with ethyl acetate (2×50 mL) and the combined organic phases were washed with brine (30 mL), dried (MgSO$_4$) and concentrated. This material was chromatographed on silica gel with ethyl acetate:hexane (1:1) as eluant to afford 5-bromo-3-(1-methyl-5-pyrrolidin-2-onyl) pyridine as a solid (329 mg, 68%). M.p. 85°–87° C.; $^1$H NMR (CDCl$_3$, 300 MHz): δ 8.66 (d, J=2 Hz, 1H), 8.42 (d, J=2 Hz, 1H), 7.68 (t, J=2 Hz, 1H), 4.56 (t, J=7 Hz, 1H), 2.71 (s, 3H), 2.45–2.65 (m, 2H), 1.80–1.95 (m, 2H).

EXAMPLE 32

5-[4-(2-Hydroxy-2-methyl-3-butynyl)]-3-(1-methyl-5-pyrrolidin-2-onyl)pyridine

A mixture of 5-bromo-3-(1-methyl-5-pyrrolidin-2-onyl) pyridine (255 mg, 1 mmol), 10% palladium on charcoal (26 mg, 0.025 mmol), copper(I)iodide (19 mg, 0.1 mmol), triphenylphosphine (26 mg, 0.1 mmol) and potassium carbonate (345 mg, 2.5 mmol) in DME (3 mL) and water (3 mL) was stirred at 25° C. After 0.75 h 2-methyl-3-butyn-2-ol (0.24 mL, 2.5 mmol) was added and the reaction flask was heated at 80° C. for 7 h. Water (5 mL) and ethyl acetate (20 mL) were added to the cooled mixture and this was filtered through celite. The organic phase was separated and the aqueous phase was extracted with ethyl acetate (3×10 mL). The combined ethyl acetate extracts were washed with brine (20 mL), dried (MgSO$_4$), filtered and concentrated. The crude product was purified by silica gel column chromatography with ethyl acetate:hexane (1:1) and (3:1) to ethyl acetate as eluants to afford 5-[4-(2-hydroxy-2-methyl-3-butynyl)]-3-(1-methyl-5-pyrrolidin-2-onyl)pyridine as an oil (227 mg, 88%). LRMS (EI) m/e 259 (M$^+$+H), 258 (M$^+$), 257 (M$^+$−H); $^1$H NMR (CDCl$_3$, 300 MHz): δ 8.67 (d, J=2 Hz, 1H), 8.41 (d, J=2 Hz, 1H), 7.55 (t, J=2 Hz, 1H), 4.56 (app t, 1H), 2.69 (s, 1H), 2.45–2.65 (m, 3H), 1.86 (m, 1H), 1.81 (s, 1H), 1.64 (s, 6H).

EXAMPLE 33

5-Ethynyl-3-(1-methyl-5-pyrrolidin-2-onyl)pyridine 5-(2-Hydroxy-2-methyl-3-butynyl)-3-(1-methyl-5-pyrrolidin-2-onyl)pyridine (200 mg, 0.77 mmol) was dissolved in toluene (20 mL) and catalytic sodium hydride (5 mg) was added. The solution was heated until several milliliters of toluene-acetone mixture were removed by distillation. The mixture was cooled to 25° C. and water (10 mL) and ethyl acetate (20 mL) were added. The organic phase was separated and the aqueous layer extracted with ethyl acetate (2×20 mL) and the combined organic extracts were washed with brine (10 mL), dried (MgSO$_4$) and concentrated in vacuo. The crude product was purified by silica gel column chromatography with ethyl acetate as eluant to afford 5-ethynyl-3-(1-methyl-5-pyrrolidin-2-onyl) pyridine as a solid (125 mg, 81%). M.p. 83°–84° C.; $^1$H NMR (CDCl$_3$, 300 MHz): δ 8.69 (d, J=2 Hz, 1H), 8.46 (d, J=2 Hz, 1H), 7.62 (t, J=2 Hz, 1H), 4.57 (dd, J=7, 6 Hz, 1H), 3.28 (s, 1H), 2.70 (s, 3H), 2.45–2.65 (m, 3H), 1.88 (m, 1H).

EXAMPLE 34

1,10-Bis-5-[3-(1-methyl-2-pyrrolidinyl)pyridine]-deca-1,9-diyne fumarate

A mixture of 5-bromo-3-(1-methyl-2-pyrrolidinyl) pyridine (1.2 g, 5 mmol), 10% palladium on charcoal (160 mg, 0.15 mmol), copper(I)iodide (57 mg, 0.3 mmol), triphenylphosphine (157 mg, 0.6 mmol) and potassium carbonate (1.73 g, 12.5 mmol) in DME (10 mL) and water (5 mL) was stirred at 25° C. After 1 h 1,9-decadiyne (335 mg, 2.5 mmol) was added and the reaction flask was heated at 80° C. for 18 h. The cooled mixture was then filtered through celite and the filtrate concentrated in vacuo. The mixture was then acidified with 1M HCl (50 mL) and extracted with toluene (50 mL). The aqueous layer was made basic with solid potassium carbonate and extracted with ethyl acetate (2×100 mL). The combined ethyl acetate extracts were washed with water (50 mL), dried (MgSO$_4$) and concentrated. The crude product was purified by silica gel column chromatography with methanol: methylene chloride (1:19) as eluant to afford the product as an oil (710 mg, 63%). This material (690 mg) was converted to the title compound by the addition of two equivalents of fumaric acid to a methanol (10 mL) solution of the free amine at 25° C. After 30 minutes the solvent was removed in vacuo and the residue pumped under high vacuum. Trituration with diethyl ether followed by recrystallization from ethyl acetate afforded 1,10-bis-5-[3-(1-methyl-2-pyrrolidinyl)pyridine]-deca-1,9-diyne fumarate, 420 mg, 31%. M.p. 170°–172° C. (EtOAc); $^1$H NMR (CD$_3$OD, 300 MHz): δ 8.70 (bs, 4H), 7.93 (s, 2H), 6.55 (s, 8H), 4.16 (app. t, J=9 Hz, 2H), 3.66 (m, 2H), 3.06 (m, 2H), 2.54 (s, 6H), 2.33 (m, 6H), 2.11 (s, 6H), 1.46 (m, 4H), 1.35 (m, 4H).

EXAMPLE 35

Enantiomerically enriched 5-bromo-3-(2-pyrrolidinyl)pyridine

Carbobenzyloxy-L-proline (37.4 g, 150 mmol) was dissolved in DME (100 mL) and cooled to 0° C. with stirring. Sodium borohydride (1.89 g, 50 mmol) was added in portions (gas evolution) and the resulting mixture was stirred for 2 h at 25° C. affording a colorless solution. The solvents were removed in vacuo and the resulting gum dissolved in methylene chloride (50 mL). To this solution was added a mixture of 5-bromo-3-(2-pyrrolin-1-yl) pyridine (5.63 g, 25 mmol) and carbobenzyloxy-L-proline (6.23 g, 25 mmol) in methylene chloride (50 mL) and this was stirred at 25° C. for 36 h. The solvent was removed in vacuo and 6M HCl (200 mL) was added to the residue. The resulting solution was extracted with isopropyl acetate (200 mL) and the phases separated. The acidic aqueous phase was basified with solid NaOH to pH 14 and then extracted with methylene chloride (3×200 mL). The combined methylene chloride extracts were washed with brine (150 mL), dried (MgSO$_4$) and concentrated in vacuo. The crude product was chromatographed on silica gel with ethyl acetate, then methanol:ethyl acetate (1:19 to 1:9) as eluants to afford 5-bromo-3-(2-pyrrolidinyl)pyridine (4.1 g, 72%) obtained as a pale yellow oil. LRMS (EI) m/e 227 ($C_9H_{11}N_2{}^{81}Br$—$H^+$), 225 ($C_9H_{11}N_2{}^{79}Br$—$H^+$); $^1H$ NMR (DMSO-$d_6$, 300 MHz) δ 8.53 (d, J=2.2 Hz, 1H), 8.49 (d, J=1.8 Hz, 1H), 7.91 (t, J=2.0 Hz, 1H), 4.17 (t, J=7.7 Hz, 1H), 3.18 (m, 1H), 3.06 (m, 1H), 2.00 (m, 1H), 2.07 (s, 1H), 2.00–1.77 (m, 2H), 1.63 (m, 1H).

The enantiomeric enrichment of this material (30% ee) was assessed using $^1H$ NMR with (R)-(+)-α-methoxy-α-(trifluoromethyl)phenylacetic acid as a chiral shift reagent.

EXAMPLE 36

Enantiomerically enriched 5-bromo-3-(1-methyl-2-pyrrolidinyl)pyridine

Enantiomerically enriched 5-bromo-3-(2-pyrrolidinyl) pyridine (1.82 g, 8 mmol) was dissolved in a mixture of 98% formic acid (16 mL) and 37% aqueous formaldehyde (8 mL). The solution was heated with stirring for 3 h at 80° C. After cooling to 25° C. the mixture was concentrated in vacuo and water (30 mL) added. The mixture was basified with solid NaOH to pH 12 and extracted with methylene chloride (3×40 mL). The combined organic extracts were washed with brine (20 mL), dried (MgSO$_4$) and concentrated in vacuo. The crude material was chromatographed on silica gel with ethyl acetate:hexane (1:3) as eluant to afford 5-bromo-3-(1-methyl-2-pyrrolidinyl)pyridine as an oil, 1.63 g, 84%. LRMS (EI) m/e 242 ($C_{10}H_{13}N_2{}^{81}Br$), 241 ($C_{10}H_{13}N_2{}^{79}Br$—$^+H$), 240 ($C_{10}H_{13}N_2{}^{79}Br$), 239 ($C_{10}H_{13}N_2{}^{79}Br$—$^+H$); $^1H$ NMR (DMSO-$d_6$, 300 MHz) δ 8.55 (d, J=2.1 Hz, 1H), 8.44 (d, J=1.9 Hz, 1H), 7.88 (t, J=1.9 Hz, 1H), 3.24 (b-dt, J=8.1 Hz, 1H), 3.10 (t, J=8.0 Hz, 1H), 2.36 (m, 1H), 2.18 (s, 3H), 1.95 (m, 1H), 1.85 (m, 1H), 1.70 (m, 1H).

A portion of this material (482 mg) was treated with di-p-toluoyl-D-tartaric acid monohydrate (534 mg) and recrystallized from ethanol-ethyl acetate (1:4) to afford 5-bromo-3-(1-methyl-2-pyrrolidinyl)pyridine of approximately 90% ee as determined by chiral GC. This material, as the free amine, was elaborated as described in Example 37.

EXAMPLE 37

Repeating the procedure of Example 23 but using 2-methyl-3-butyn-2-ol in place of propargyl alcohol the following enantiomerically enriched compound was obtained:

5-[4-(2-Hydroxy-2-methyl-3-butynyl)]-3-(1-methyl-2-pyrrolidinyl)pyridine.

M.p. 79°–81° C. (Cyclohexane); $^1H$ NMR (CDCl$_3$, 300 MHz): δ 8.65 (d, J=2 Hz, 1H), 8.41 (d, J=2 Hz, 1H), 7.80 (t, J=2 Hz, 1H), 4.71 (bs, 1H), 3.24 (app. td, J=7.2 Hz, 1H), 3.07 (app. t, J=9 Hz, 1H), 2.31 (app. dd, J=9, 9 Hz, 1H), 2.19 (m, 1H), 2.16 (s, 3H), 1.9–2.1 (m, 1H), 1.77–1.90 (m, 1H), 1.65–1.77 (m, 1H), 1.62 (s, 6H).

EXAMPLE 38

Repeating the procedure of Example 28 but using 5-[4-(2-hydroxy-2-methyl-3-butynyl)]-3-(1-methyl-2-pyrrolidinyl)pyridine in place of 5-(2-hydroxy-2-methyl-3-butynyl)-3-(1-tert-butyloxycarbonyl-2-pyrrolidinyl) pyridine the following product was obtained:
5-Ethynyl-3-(1-methyl-2-pyrrolidinyl)pyridine.

LRMS (EI) m/e 187 ($M^+$+H), 186 ($M^+$), 185 ($M^+$–H); $^1H$ NMR (CDCl$_3$, 300 MHz): δ 8.58 (d, J=2 Hz, 1H), 8.48 (d, J=2 Hz, 1H), 7.80 (app. t, J=2 Hz, 1H), 3.23 (t, J=8 Hz, 1H), 3.18 (s, 1H), 3.08 (app. t, J=8.5 Hz, 1H), 2.30 (dd, J=9, 9 Hz, 1H), 2.21 (m, 1H), 2.16 (s, 3H), 1.65–2.00 (m, 3H).

A portion of this material (248 mg) was treated with di-p-toluoyl-D-tartaric acid monohydrate (485 mg) and recrystallized from ethanol to afford 5-ethynyl-3-(1-methyl-2-pyrrolidinyl)pyridine di-p-toluoyl-D-tartrate (452 mg, 66%).M.p. 163°–164° C. (EtOH); $^1H$ NMR (DMSO-$d_6$, 300 MHz): δ 8.66 (d, J=2 Hz, 1H), 8.63 (d, J=2 Hz, 1H), 7.99 (t, J=2 Hz, 1H), 7.88 (d, J=8 Hz, 2H), 7.37 (d, J=8 Hz, 2H), 5.74 (s, 2H), 4.48 (s, 1H), 3.8 (b-m, 1H), 3.4 (b-m, 1H), 2.73 (dd, J=9, 9 Hz, 1H), 2.39 (s, 6H), 2.35 (s, 3H), 2.3 (m, 1H), 1.8–2.0 (m, 3H).

This product possessed a 97% enantiomeric excess as determined by chiral GC.

EXAMPLE 39

Repeating the procedures of Example 36 to Example 38 but using the appropriate compounds of opposite configuration the following product was obtained:
5-Ethynyl-3-(1-methyl-2-pyrrolidinyl)pyridine di-p-toluoyl-L-tartrate.

M.p. 158°–159° C. (EtOH); $^1H$ NMR (DMSO-$d_6$, 300 MHz): δ 8.65 (d, J=2 Hz, 1H), 8.60 (d, J=2 Hz, 1H), 7.97 (t, J=2 Hz, 1H), 7.87 (d, J=8 Hz, 2H), 7.36 (d, J=8 Hz, 2H), 5.74 (s, 2H), 4.50 (s, 1H), 3.71 (m, 1H), 3.39 (m, 1H), 2.65 (dd, J=9, 9 Hz, 1H), 2.38 (s, 6H), 2.29 (s, 3H), 2.23 (m, 1H), 1.75–1.95 (m, 3H).

This product possessed a 95% enantiomeric excess as determined by chiral GC.

EXAMPLE 40

Radioligand Binding $^3H$-Nicotine binding to rat cerebral membranes was performed according to modifications of the method of Flyn and Mash (*J. Neurochem.* 47:1948 (1986)). $^3H$-Nicotine (80 ci/mmol; New England Nuclear Corporation, Boston, Mass.) was used as the ligand for nicotinic acetylcholine receptor binding assays. All other reagents were purchased from the Sigma Chemical Co. (St. Louis, Mo.).

Male Sprague-Dawley rats (250–400 gm) were sacrificed by decapitation, the brains removed and the cerebral cortex dissected on ice. Synaptic membranes were prepared by homogenizing the cortical tissue in 20 volumes of ice-cold modified Tris buffer (50 mM Tris pH 7.4, 120 mM NaCl, 5 mM KCl, 2 mM EDTA, 1 mM PMSF) with a polytron (20 sec at setting 5–6) followed by centrifugation (15 min at 5,000×g) at 4° C. The resultant pellet was rehomogenized and centrifuged twice. The final pellet was resuspended in ice-cold assay buffer (50 mM Tris pH 7.4, 120 mM NaCl, 5 mM KCl, 2 mM CaCl$_2$, 1 mM MgCl$_2$) at a concentration of membrane equivalent to 1 gm wet weight cortex per 10 ml buffer. After protein determination the final membrane preparation was diluted with buffer to 3 mg protein/ml. This membrane preparation was used in either the fresh state or frozen (–70° C.) then thawed.

The binding assay is performed manually using 96-well plates, or using a Biomek automated work station (Beckman Instrument Co.). $^3H$-Nicotine was diluted in assay buffer to give a final concentration of 1.9 nM. The Biomek automated work station was programmed to automatically transfer 750 μl of assay buffer with $^3H$-nicotine, 230 μl of membrane preparation and 20 μl of solution containing the compound of interest in assay buffer, DMSO, ethanol:DMSO (1:1) or appropriate vehicle to the 96-well plate. Atropine was added to the incubation buffer at a final concentration of 3 µM to block binding to muscarinic acetylcholine receptor sites. The plates were maintained on ice for 60 min and the tissue-bound radioactivity was separated from the free by rapid filtration in a Brandel Harvester onto GF/C filters presoaked in 0.5% polyethyleneimine for at least 2 hr. The filters were washed with 4×2 ml of ice-cold assay buffer and filters were transferred to vials to which 4 ml of scintillation cocktail was added. The radioactivity was measured in a LS-6500 Beckman Liquid Scintillation Counter in an autodpm mode. Data were analyzed bylog-logit transformation or non-linear regression analysis (e.g., employing GraphPad Prism, available from GraphPad Software, San Diego, Calif.) to give $IC_{50}$ values. Non-specific binding was defined by 10 µM cytisine.

The ability of invention compounds to displace $^3$H-QNB (quinuclidinyl benzilate; 43 Ci/mmol, 60 pM) from muscarinic acetylcholine receptors in rat cerebral membranes can also be tested using the above-described method in which $^3$H-nicotine is replaced with any radiolabeled acetylcholine receptor ligand.

The results of $^3$H-nicotine and $^3$H-QNB binding/displacment assays of several invention compounds are summarized in Table I.

TABLE I

| Compound Tested, Formula I, wherein ... | $IC_{50}$ (µM) | |
|---|---|---|
| | Nicotine | Quinuclidinyl benzilate |
| $A = CH_2$; $B = CH_2$; $R^2, R^4, R^6, R^9, R^{9a} = H$; $R^7 = CH_3$; $R^5 = 4$-biphenyl | 0.047 | 9.5 |
| $A = CH_2$; $B = CH_2$; $R^2, R^4, R^6, R^9, R^{9a} = H$; $R^7 = CH_3$; $R^5 = 3$-chloro-4-hydroxyphenyl | 0.028 | >10 |
| $A = CH_2$; $B = CH_2$; $R^2, R^4, R^6, R^9, R^{9a} = H$; $R^7 = CH_3$; $R^5 = 4$-methylphenyl | 0.031 | 14 |
| $A = CH_2$; $B = CH_2$; $R^2, R^4, R^6, R^9, R^{9a} = H$; $R^7 = CH_3$; $R^5 = 4$-methyoxyphenyl | 0.018 | 37.7 |
| $A = CH_2$; $B = CH_2$; $R^2, R^4, R^6, R^9, R^{9a} = H$; $R^7 = CH_3$; $R^5 = 4$-hydroxyphenyl | 0.0054 | 19.1 |
| $A = CH_2$; $B = CH_2$; $R^2, R^4, R^6, R^9, R^{9a} = H$; $R^7 = CH_3$; $R^5 = 3$-chlorophenyl | 0.12 | 3.7 |
| $A = -CH_2CH_2-$; $B = CH_2$; $R^2, R^4, R^6, R^9, R^{9a} = H$; $R^7 = H$; $R^5 = 4$-fluorophenyl | 0.49 | 24.9 |
| $A = CH_2$; $B = CH_2$; $R^2, R^4, R^6, R^9, R^{9a} = H$; $R^7 = CH_3$; $R^5 =$ ethynyl (racemic) | 0.0046 | 10.1 |
| $A = CH_2$; $B = CH_2$; $R^2, R^4, R^6, R^9, R^{9a} = H$; $R^7 = CH_3$; $R^5 = 3$-fluoro-4-hydroxyphenyl | 0.029 | 35 |
| $A = CH_2$; $B = CH_2$; $R^2, R^4, R^6, R^9, R^{9a} = H$; $R^7 = CH_3$; $R^5 = 3$-fluoro-4-methoxyphenyl | 0.027 | 30.5 |
| $A = CH_2$; $B = CH_2$; $R^2, R^4, R^6, R^9, R^{9a} = H$; | 0.0036 | >100 |

TABLE I-continued

| Compound Tested, Formula I, wherein ... | $IC_{50}$ (µM) | |
|---|---|---|
| | Nicotine | Quinuclidinyl benzilate |
| $R^7 = CH_3$; $R^5 = 5$-(1-hydroxy-2-propynyl) $A = CH_2$; $B = CH_2$; $R^2, R^4, R^6, R^9, R^{9a} = H$; | 0.011 | >100 |
| $R^7 = CH_3$; $R^5 = 5$-(2-hydroxy-3-butynyl) $A = CH_2$; $B = CH_2$; $R^2, R^4, R^6, R^9, R^{9a} = H$; | 0.006 | >100 |
| $R^7 = CH_3$; $R^5 = 5$-(1-hydroxy-3-butynyl) $A = CH_2$; $B = CH_2$; $R^2, R^4, R^6, R^9, R^{9a} = H$; | 0.0042 | 39 |
| $R^7 = CH_3$; $R^5 = 5$-(1-pentynyl) $A = CH_2$; $B = CH_2$; $R^2, R^4, R^6, R^9, R^{9a} = H$; | 0.038 | >100 |
| $R^7 = CH_3$; $R^5 = 5$-(2-hydroxy-2-methyl-3-butynyl) $A = CH_2$; $B = CH_2$; $R^2, R^4, R^6, R^9, R^{9a} = H$; | 0.025 | 100 |
| $R^7 = CH_3$; $R^5 = 5$-(1-dimethylamino-2-propynyl) $A = CH_2$; $B = CH_2$; $R^2, R^4, R^6, R^9, R^{9a} = H$; | 0.0026 | >100 |
| $R^7 = CH_3$; $R^5 = 5$-(1-methoxy-2-propynyl) $A = CH_2$; $B = CH_2$; $R^2, R^4, R^6, R^9, R^{9a} = H$; | 0.029 | >100 |
| $R^7 = CH_3$; $R^5 = 5$-(1-propynyl) $A = CH_2$; $B = CH_2$; $R^2, R^4, R^6, R^9, R^{9a} = H$; | 0.058 | 8.9 |
| $R^7 = H$; $R^5 = 5$-(1-ethynyl) $A = C(O)$; $B = CH_2$; $R^2, R^4, R^6, R^9, R^{9a} = H$; | >100 | >100 |
| $R^7 = CH_3$; $R^5 = 5$-(1-ethynyl) $A = CH_2$; $B = CH_2$; $R^2, R^4, R^6, R^9, R^{9a} = H$; | 0.0026 | n.d. |
| $R^7 = CH_3$; $R^5 = 5$-(1-ethynyl) Di-p-toluoyl-L-tartrate $A = CH_2$; $B = CH_2$; $R^2, R^4, R^6, R^9, R^{9a} = H$; | 0.078 | 4.7 |
| $R^7 = CH_3$; $R^5 = 5$-(1-ethynyl) Di-p-toluoyl-D-tartrate $A = CH_2$; $B = CH_2$; $R^2, R^4, R^6, R^9, R^{9a} = H$; | 0.0052 | 7.5 |
| $R^7 = CH_3$; $R^5 =$ See below* | | |

*$R^5 = 5$-[1-(10-[5-(3-[1-methyl-2-pyrrolidinyl]pyridine)-deca-1,9-diynyl

As evidenced by the $IC_{50}$ values in the Table, each of the compounds tested was able to displace acetylcholine receptor ligands from their binding sites in rat cerebral membranes.

EXAMPLE 41

Neurotransmitter Release

Measurement of $^3$H-dopamine release from rat striatal slices was performed according to the method of Sacaan et al. (*J. Neurochem.* 59:245 (1992)). Male Sprague-Dawley rats (250–300 g) were decapitated and the striata or olfactory tubercles dissected quickly on a cold glass surface. The tissue was chopped to a thickness of 300 µm with a McIlwain tissue chopper. After chopping again at right angles the tissue was dispersed and incubated for 10 min. at 37° C. in oxygenated Kreb's buffer. $^3$H-Dopamine (40 Ci/mmol, NEN- Dupont, Boston, Mass.) was added (50 nM) and the tissue was incubated for 30 min. in Kreb's buffer containing 10 μM pargyline and 0.5 mM ascorbic acid. Aliquots of the minced tissue were then transferred to chambers of a Brandel Superfusion system in which the tissue was supported on Whatman GF/B filter discs. The tissue was then superfused with buffer at a constant flow rate of 0.3 ml/min by means of a Brandel peristaltic pump. The perfusate was collected in plastic scintillation vials in 3-min fractions, and the radioactivity was estimated by scintillation spectrophotometry. The superfusate for the first 120 min was discarded. After two baseline fractions had been collected, the superfusion buffer was switched to fresh buffer with or without compound of interest. At the end of the experiment the filter and the tissue were removed, and the radiolabeled neurotransmitter content was estimated after extraction into scintillation fluid. The fractional efflux of radiolabeled neurotransmitter was estimated as the amount of radioactivity in the perfusate fraction relative to the total amount in the tissue.

Following essentially the same procedure as set forth above, the amount of $^3$H-norepinephrine released from rat hippocampus, thalamus and prefrontal cortex slices superfused with buffer containing (or lacking) compounds of interest was also measured.

Results of studies of the effects of an invention compound (as compared to the effect of nicotine) on the release of neurotransmitters from rat brain slices are presented in Table II. Results presented in Part A of the Table are expressed as the percent fractional release and results presented in Part B of the Table are expressed as a percentage, relative to nicotine response.

TABLE II

Part A
Ligand-stimulated $^3$H-neurotransmitter Release in vitro from Slices of Different Rat Brain Regions

| Ligand or Compound Tested, Formula I, wherein... | $^3$H-Dopamine Striatum | $^3$H-Norepinephrine Hippocampus | $^3$H-Norepinephrine Thalamus | $^3$H-Norepinephrine Prefrontal Cortex | $^3$H-Dopamine Olfactory Tubercles |
|---|---|---|---|---|---|
| Nicotine | 1.84[a] | 6.19[b] | 1.83[a] | 2.32[b] | 5.61[a] |
| A = CH$_2$; B = CH$_2$; R$^2$, R$^4$, R$^6$, R$^9$, R$^{9a}$ = H; R$^7$ = CH$_3$; R$^5$ = 4-biphenyl (300 μM) | 2.2 | 2.9 | 1.1 | 3.4 | 6.3 |
| A = CH$_2$; B = CH$_2$; R$^2$, R$^4$, R$^6$, R$^9$, R$^{9a}$ = H; R$^7$ = CH$_3$; R$^5$ = 3-chloro-4-hydroxyphenyl (300 μM) | 8.34 | 2.5 | 3.23 | 2.94 | 11.4 |
| A = CH$_2$; B = CH$_2$; R$^2$, R$^4$, R$^6$, R$^9$, R$^{9a}$ = H; R$^7$ = CH$_3$; R$^5$ = 4-methylphenyl (300 μM) | 0.74 | 0.52 | 0.31 | NT[c] | 1.0 |
| A = CH$_2$; B = CH$_2$; R$^2$, R$^4$, R$^6$, R$^9$, R$^{9a}$ = H; R$^7$ = CH$_3$; R$^5$ = 4-methyoxyphenyl (300 μM) | 2.1 | 0.99 | 0.52 | 1.04 | 4.0 |
| A = CH$_2$; B = CH$_2$; R$^2$, R$^4$, R$^6$, R$^9$, R$^{9a}$ = H; R$^7$ = CH$_3$; R$^5$ = 4-hydroxyphenyl (300 μM) | 3.73 | 3.03 | 2.3 | 3.16 | 6.62 |
| A = CH$_2$; B = CH$_2$; R$^2$, R$^4$, R$^6$, R$^9$, R$^{9a}$ = H; R$^7$ = CH$_3$; R$^5$ = 3-chlorophenyl (300 μM) | 2.0 | 1.45 | 1.48 | 1.7 | 3.25 |
| A = CH$_2$; B = CH$_2$; R$^2$, R$^4$, R$^6$, R$^9$, R$^{9a}$ = H; R$^7$ = CH$_3$; R$^5$ = 4-fluorophenyl (300 μM) | 1.96 | 0.58 | 0.9 | 1.23 | 2.68 |
| A = CH$_2$; B = CH$_2$; R$^2$, R$^4$, R$^6$, R$^9$, R$^{9a}$ = H; R$^7$ = CH$_3$; R$^5$ = ethynyl (300 μM) | 2.56 | 0.69 | 0.31 | 0.97 | 6.68 |
| A = CH$_2$; B = CH$_2$; R$^2$, R$^4$, R$^6$, R$^9$, R$^{9a}$ = H; R$^7$ = CH$_3$; R$^5$ = 3-fluoro-4-hydroxyphenyl (300 μM) | 3.33 | 1.47 | NT[c] | 1.14 | 7.07 |
| A = CH$_2$; B = CH$_2$; R$^2$, R$^4$, R$^6$, R$^9$, R$^{9a}$ = H; R$^7$ = CH$_3$; R$^5$ = 3-fluoro-4-methoxyphenyl (300 μM) | 3.1 | 0.73 | 1.75 | 2.0 | 2.3 |

[a]Nicotine concentration was 100 μM.
[b]Nicotine concentration was 300 μM.
[c]NT = not tested.

TABLE II

Part B
Ligand-stimulated Neurotransmitter Release Data

| | % of Nicotine Response[a] | |
|---|---|---|
| Ligand or Compound Tested | $^3$H-Dopamine Striatum | $^3$H-Norepinephrine Hippocampus |
| Nicotine | 100 (10 μM) | 100 (300 μM) |
| A = $CH_2$; B = $CH_2$; $R^2$, $R^4$, $R^6$, $R^9$, $R^{9a}$ = H; $R^7$ = $CH_3$; $R^5$ = 5-[3-(1-hydroxy-2-propynyl)] | 156.8 | 39.0 |
| A = $CH_2$; B = $CH_2$; $R^2$, $R^4$, $R^6$, $R^9$, $R^{9a}$ = H; $R^7$ = $CH_3$; $R^5$ = 5-[3-(2-hydroxy-3-butynyl)] | 98.0 | 30.5 |
| A = $CH_2$; B = $CH_2$; $R^2$, $R^4$, $R^6$, $R^9$, $R^{9a}$ = H; $R^7$ = $CH_3$; $R^5$ = 5-[3-(1-hydroxy-3-butynyl)] | 100.0 | 36.3 |
| A = $CH_2$; B = $CH_2$; $R^2$, $R^4$, $R^6$, $R^9$, $R^{9a}$ = H; $R^7$ = $CH_3$; $R^5$ = 5-(1-pentynyl) | 27.7 | n.d.[b] |
| A = $CH_2$; B = $CH_2$; $R^2$, $R^4$, $R^6$, $R^9$, $R^{9a}$ = H; $R^7$ = $CH_3$; $R^5$ = 5-[4-(2-hydroxy-2-methyl-3-butynyl) | 118.3 | 18.3 |
| A = $CH_2$; B = $CH_2$; $R^2$, $R^4$, $R^6$, $R^9$, $R^{9a}$ = H; $R^7$ = $CH_3$; $R^5$ = 5-[3-(1-dimethylamino-2-propynyl)] | 235.2 | n.d. |
| A = $CH_2$; B = $CH_2$; $R^2$, $R^4$, $R^6$, $R^9$, $R^{9a}$ = H; $R^7$ = $CH_3$; $R^5$ = 5-[3-(1-methoxy-2-propynyl)] | 61.7 | 7.4 |
| A = $CH_2$; B = $CH_2$; $R^2$, $R^4$, $R^6$, $R^9$, $R^{9a}$ = H; $R^7$ = H; $R^5$ = 5-(1-ethynyl) | 61.7 | 13.4 |
| A = $CH_2$; B = $CH_2$; $R^2$, $R^4$, $R^6$, $R^9$, $R^{9a}$ = H; $R^7$ = $CH_3$; $R^5$ = 5-(1-ethynyl) Di-p-toluoyl-L-tartrate | 155[c] | 17.4 |
| A = $CH_2$; B = $CH_2$; $R^2$, $R^4$, $R^6$, $R^9$, $R^{9a}$ = H; $R^7$ = $CH_3$; $R^5$ = 5-(1-ethynyl) Di-p-toluoyl-D-tartrate | 33 | 3.7 |

[a]All compounds were tested at 300 μM, unless noted otherwise.
[b]n.d. = not determined
[c]Nicotine concentration was 300 μM As shown in Table II, invention compound selectively induces release of catecholamines in different brain regions.

EXAMPLE 42

6-Hydroxydopamine Lesion Model of Parkinsonism

Selective lesions of the brain dopamine pathway using the neurotoxin 6-hydroxydopamine (6-OHDA) in rats can be used as an experimental approach to Parkinson's disease. Unilateral lesions of the nigrostriatal dopamine pathway induce a postural asymmetry which becomes manifested as rotation when the animals are activated by dopamine releasers or dopamine agonists. When amphetamine and other stimulant drugs that induce pre-synaptic release of dopamine from intact nerve terminals are administered, the rats rotate in a direction ipsilateral to the lesion. In contrast, when the rats are injected with post-synaptic dopamine receptor agonists, such as apomorphine, they turn in a contralateral direction, due to the development of supersensitive dopamine receptors in the lesioned side. Thus, the 6-OHDA model can be used to determine if a suspected dopaminergic agent is active, and to differentiate whether such action is pre- or post-synaptic.

The effects of invention compounds on rotational behavior in 6-hydroxydopamine denervated rats were evaluated using the procedure of Ungerstedt and Arbutknott, Brain Res. 24:485–493 (1970). Male Sprague-Dawley rats (Zivic Miller) weighing 170–200 gm were used in the 6-OHDA procedure. The ascending nigrostriatal dopamine pathway was lesioned by unilateral stereotaxic injection of 6-OHDA (8.0 μg) into one substantia nigra. All injections of 6-OHDA were preceded by desmethylimipramine (25 mg/kg i.p.) and pargyline (75 mg/kg i.p.) approximately 30 minutes prior to undergoing stereotaxic surgery for 6-OHDA infusion into the substantia nigra. After one week of recovery from surgery, the effectiveness of the lesions was verified by noting the response of the animals to apomorphine (0.2 mg/kg, s.c.). Only rats with a minimum rate of 80 contralateral turns per 30 minutes (a sign of more than 80–90% dopamine depletion after a 6-OHDA lesion) were used. Two weeks later, the selected rats were tested with invention and reference compounds using an automated rotometer system to record the number and direction of rotations. In order to distinguish spontaneous (non-specific) rotations from induced rotations (specific to the effect of the drug), each rat was used as its own control, employing the following procedure:

The rat was placed in the rotometer system for acclimatation for 15 minutes, the vehicle administered subcutaneously, the rat's rotations recorded for one hour, then test compound was administered s.c. and rotations again recorded for one hour. The number of ipsilateral rotations induced by vehicle was then compared to the number of ipsilateral rotations induced by test compound. Statistical analysis of the data was carried out using Student's t-test (paired).

The results of one such study are shown in Table III. Results are reported as the percentage change of ipsilateral rotations, relative to control, per one hour interval. No contralateral rotations were observed with the tested compounds.

TABLE III

Induction of turning in rats with unilateral 6-hydroxydopamine lesions of the nigrostriatal dopamine pathway

| Ligand or Compound Tested | Percent change from control[a] |
|---|---|
| Nicotine (1 mg/kg salt, s.c.) | +357 |
| Amphetamine (1 mg/kg base, s.c.) | +487 |
| Compound I (20 mg/kg), wherein A = $CH_2$, B = $CH_2$, $R^2$, $R^4$, $R^6$, $R^9$, $R^{9a}$ = H $R^7$ = $CH_3$ $R^5$ = ethynyl | +406 |
| Compound I (20 mg/kg), wherein A = $CH_2$, B = $CH_2$, $R^2$, $R^4$, $R^6$, $R^9$, $R^{9a}$ = H $R^7$ = $CH_3$ $R^5$ = 3-fluoro-4-methoxyphenyl | −3 |
| Compound I (20 mg/kg), wherein | −40 |

TABLE III-continued

Induction of turning in rats with unilateral 6-hydroxydopamine lesions of the nigrostriatal dopamine pathway

| Ligand or Compound Tested | Percent change from control[a] |
| --- | --- |
| $A = CH_2$, $B = CH_2$, $R^2$, $R^4$, $R^6$, $R^9$, $R^{9a} = H$ $R^7 = CH_3$ $R^5 = 3$-chloro-4-hydroxyphenyl Compound I (20 mg/kg), wherein $A = CH_2$, $B = CH_2$, $R^2$, $R^4$, $R^6$, $R^9$, $R^{9a} = H$ $R^7 = CH_3$ $R^5 = 3$-chlorophenyl | +62 |

[a]n = 6–18 rats per group

As shown in Table III, invention compounds may induce significant turning towards the lesioned side. The direction of the rotations suggest increased release of dopamine from the remaining dopamine nerve terminals in the non-lesioned side of the brain. These data are consistent with in vitro release of $^3$H-dopamine from rat striatal slices (see Example 41).

EXAMPLE 43

Locomotor Activity Assay

The effects of invention compounds on locomotor activity of rats were evaluated using the procedure of O'Neill et al. *Psychopharmacology* 104:343–350 (1991). This assay can be used to assess the primary effect of a compound on general motor activity. A decrease in locomotor activity is indicative of a possible sedative effect on the animal, whereas an increase in locomotor activity is indicative of a stimulant effect on the animal.

Locomotor activity of rats (male Sprague-Dawley (Harlan) weighing 200–250 gm) was measured for 2 hrs in photocell cages immediately after administration of the invention compound. Prior to the test day, the animals were placed in the activity cages for 3 hrs to familiarize them with the experimental environment. On the test day, the animals were placed in the photocell cages and then injected with compound 1.5 hrs later.

The photocell cages were standard rodent cages (30 cm×20 cm×40 cm) with four infrared beams crossing the long axis. The animals were under no motivational constraints and were free to move around. Movements from one infrared beam to another (ambulation) were called "crossover"; successive interruptions of the same beam (vertical and other movements such as grooming) were called "general activity."

The results of one such study are shown in Table IV. Results are reported as the percent of change from control values (i.e., saline injection) for two post-injection periods: 0–60 minutes and 60–120 minutes, respectively.

TABLE IV

Locomotor activity assay with various invention compounds

| Ligand or Compound Tested | General Activity[a] (beam breaks) | | Ambulation[a] (cross overs) | |
| --- | --- | --- | --- | --- |
| | 0–60 min | 60–120 min | 0–60 min | 60–120 min |
| Nicotine (1 mg/kg salt, s.c.) | +27% | +71% | +169% | +163% |
| Amphetamine (0.5 mg/kg salt, s.c.) | +1112% | +456% | +2598% | +1217% |
| Compound I[b] wherein $A = CH_2$; $B = CH_2$; $R^2$, $R^4$, $R^6$, $R^9$, $R^{9a} = H$; $R^7 = CH_3$; $R^5 = 4$-biphenyl | −17% | +98 | −9% | +73% |
| Compound I[b] wherein $A = CH_2$; $B = CH_2$; $R^2$, $R^4$, $R^6$, $R^9$, $R^{9a} = H$; $R^7 = CH_3$; $R^5 = $ phenylethynyl | +3% | −11% | +7% | −16% |
| Compound I[b] wherein $A = CH_2$; $B = CH_2$; $R^2$, $R^4$, $R^6$, $R^9$, $R^{9a} = H$; $R^7 = CH_3$; $R^5 = 3$-fluoro-4-hydroxyphenyl | +63% | +26% | +49% | −14% |
| Compound I[b] wherein $A = CH_2$; $B = CH_2$; $R^2$, $R^4$, $R^6$, $R^9$, $R^{9a} = H$; $R^7 = CH_3$; $R^5 = 4$-methyoxyphenyl | +83% | +22% | +58% | +31% |
| Compound I[b] wherein $A = CH_2$; $B = CH_2$; $R^2$, $R^4$, $R^6$, $R^9$, $R^{9a} = H$; $R^7 = CH_3$; $R^5 = 4$-hydroxyphenyl | 96% | +7% | +74% | +110% |
| Compound I[b] wherein $A = CH_2$; $B = CH_2$; $R^2$, $R^4$, $R^6$, $R^9$, $R^{9a} = H$; $R^7 = CH_3$; $R^5 = 3$-chlorophenyl | +70% | +220% | +48% | +268% |
| Compound I[b] wherein $A = CH_2$; $B = CH_2$; $R^2$, $R^4$, $R^6$, $R^9$, $R^{9a} = H$; $R^7 = CH_3$; $R^5 = $ ethynyl | +509% | +628% | +631% | +1252% |
| Compound I[b] wherein $A = CH_2$; $B = CH_2$; $R^2$, $R^4$, $R^6$, $R^9$, $R^{9a} = H$; $R^7 = CH_3$; $R^5 = 4$-fluorophenyl | +95% | +173% | +21% | +14% |
| Compound I[b] wherein $A = CH_2$; $B = CH_2$; $R^2$, $R^4$, $R^6$, $R^9$, $R^{9a} = H$; $R^7 = CH_3$; $R^5 = 3$-fluoro-4-methoxyphenyl | +78% | +202% | +58% | +268% |
| Compound I[b] wherein $A = CH_2$; $B = CH_2$; $R^2$, $R^4$, $R^6$, $R^9$, $R^{9a} = H$; $R^7 = CH_3$; $R^5 = 3$-chloro-4-hydroxyphenyl | +68% | −17% | +63% | −36% |

[a]n = 8 animals per group except for the amphetamine group, for which n = 3
[b]Dosage is 20 mg/kg, s.c.

As shown in Table IV, invention compounds may induce an increase in locomotor activity of rats.

While the invention has been described in detail with reference to certain preferred embodiments thereof, it will be understood that modifications and variations are within the spirit and scope of that which is described and claimed.

That which is claimed is:

1. A method for the preparation of compounds having the structure I:

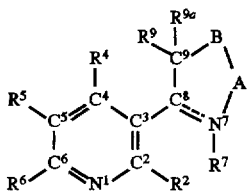

wherein:

A is a 1, 2 or 3 atom bridging species which forms part of a saturated or monosaturated 5-, 6- or 7-membered ring including $N^7$, $C^8$, $C^9$ and B, B is selected from —O—, —S—, —$NR^{10}$—, wherein $R^{10}$ is selected from hydrogen, lower alkyl, aryl, substituted aryl, alkylaryl, substituted alkylaryl, arylalkyl, substituted arylalkyl; —$C^{10}HR^{10a}$—, wherein $R^{10a}$ is selected from hydrogen, lower alkyl, hydroxyalkyl, aryl, aryloxyalkyl, fluoro, trifluoromethyl, cyano, cyanomethyl, —OR', —NR'$_2$, or —SR', wherein each R' is independently hydrogen, lower alkyl, alkenyl, alkynyl or aryl, provided, however, that neither the —NR'$_2$ nor the —SR' functionality is conjugated with an alkenyl or alkynyl functionality; or B is =$C^{10}R^{10a}$— or =N—, provided there is no double bond in the ring between A and B, or between B and $C^9$ when there is a double bond between $N^7$ and $C^8$, and provided that B is not a heteroatom when A is a 1 atom bridging species, $R^2$, $R^4$, $R^5$ and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is S(O)$_2$NHR', R' is not alkenyl or alkynyl;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR'", wherein R'" is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR'" functionality is not conjugated with an alkenyl or alkynyl functionality;

—NR'"$_2$, wherein each R'" is independently as defined above, or each R'" and the N to which they are attached can cooperate to form a 4-, 5-, 6- or 7-membered ring; provided, however, that the —NR'"$_2$ functionality is not conjugated with an alkenyl or alkynyl functionality;

—SR"", wherein R"" is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR"" functionality is not conjugated with an alkenyl or alkynyl functionality; or —SiR""$_3$, wherein R"" is selected from alkyl or aryl, $R^7$ is selected from hydrogen, lower alkyl, aryl, substituted aryl, alkylaryl, or substituted alkylaryl, or $R^7$ is absent when there is a double bond between $N^7$ and $C^8$, and $R^9$ and $R^{9a}$ are each independently selected from hydrogen, lower alkyl, hydroxyalkyl, aryl, aryloxyalkyl, fluoro, trifluoromethyl, cyano, cyanomethyl, —OR', —NR'$_2$, or —SR', wherein each R' is as defined above, provided, however, that neither the —NR'$_2$ nor the —SR' functionality is conjugated with an alkenyl or alkynyl functionality, said method comprising (a) contacting acyl pyridine precursor of Formula II with lactam of Formula III in the presence of a strong base, to produce pyridoyllactam of Formula IV, wherein II is:

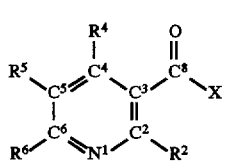

wherein III is:

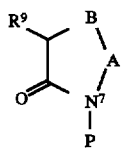

and wherein IV is:

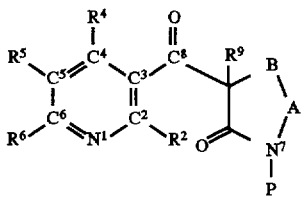

(b) rearranging IV into cyclic imine V:

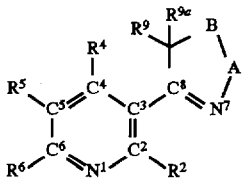

(c) reducing cyclic imine V to produce cyclic amine VI:

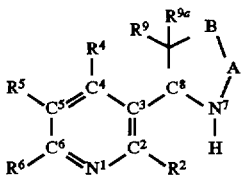

and thereafter, optionally (d) alkylating VI to produce I.

2. A method according to claim 1 wherein $R^5$ is selected from bromine, iodine or trifluoromethylsulfonyloxy.

3. A method according to claim 2 further comprising:
(e) contacting compound VI or compound I with an acetylenic compound in the presence of a suitable catalyst under conditions suitable to produce a 5-alkynyl derivative of compound VI or compound I, and thereafter, optionally
(f) contacting the product of step (e) under conditions suitable to remove any protecting group(s) present on the alkynyl moiety or the core of compound VI or compound I.

4. A method according to claim 3 wherein said acetylenic compound has the structure:

wherein $R^{5'}$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkylene, substituted alkylene, arylene, substituted arylene, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is —S(O)$_2$NHR', R' is not alkenyl or alkynyl;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''$_2$, wherein each R''' is independently as defined above, or each R''' and the N to which they are attached can cooperate to form a 4-, 5-, 6- or 7-membered ring; provided, however, that the —NR'''$_2$ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR''''$_3$, wherein R'''' is selected from alkyl or aryl.

5. A method according to claim 4 wherein said acetylenic compound is selected from acetylene, phenylacetylene, propargyl alcohol, 3-hydroxy-1-butyne, 4-hydroxy-1-butyne, 3-methyl-3-hydroxy-1-butyne, 1-pentyne, 3-dimethylamino propyne or 3-hydroxypropyne.

6. A method according to claim 3 wherein said suitable catalyst comprises a combination of palladium on carbon, copper(I)iodide, triphenylphosphine and base.

7. A method according to claim 3 further comprising:
(g) contacting the product of step (e) or step (f) with an acid capable of forming an optically pure acid addition salt with an enantiomeric mixture of said 5-alkynyl derivative of compound VI or compound I.

8. A method according to claim 7 further comprising separating the optically pure acid addition salt of said 5-alkynyl derivative of compound VI or compound I from the non-crystallized enantiomer of the 5-alkynyl derivative of compound VI or compound I.

9. A method according to claim 3 further comprising:
(g) converting the product of step (e) or step (f) into a diastereomeric derivative of racemic amines.

10. A method comprising separating the diastereomeric derivatives produced by claim 9.

11. A method according to claim 1 wherein the strong base employed in step (a) is lithium hexamethyldisilazide, sodium hydride or lithium diisopropylamide.

12. A method according to claim 1 wherein step (b) is promoted by contact with strong acid.

13. A method according to claim 1 wherein step (c) is catalyzed by sodium borohydride, sodium cyanoborohydride, lithium aluminum hydride, sodium triacetoxyborohydride, lithium tri-tert-butoxy aluminum hydride, sodium trimethoxy borohydride, diisobutylaluminum hydride, formic acid, or by contacting the imine with hydrogen in the presence of a transition metal catalyst.

14. A method according to claim 1 wherein step (c) is catalyzed by sodium borohydride.

15. A method according to claim 1 wherein step (d) N-alkylation reaction is carried out by contacting compounds of formula VI with an aldehyde in the presence of a suitable reducing agent.

16. A method according to claim 15 wherein said aldehyde is selected from formaldehyde, acetaldehyde or benzaldehyde.

17. A method for the preparation of compounds having the structure I:

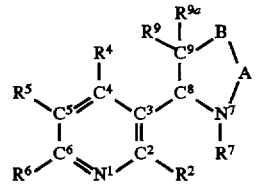

wherein

A is a 1, 2 or 3 atom bridging species which forms part of a saturated or monounsaturated 5-, 6- or 7-membered ring including $N^7$, $C^8$, $C^9$ and B, B is selected from —O—, —S—, —NR$^{10}$—, wherein R$^{10}$ is selected from hydrogen, lower alkyl, aryl, substituted aryl, alkylaryl, substituted alkylaryl, arylalkyl, substituted arylalkyl; —C$^{10}$HR$^{10a}$—, wherein R$^{10a}$ is selected from hydrogen, lower alkyl, hydroxyalkyl, aryl, aryloxyalkyl, fluoro, trifluoromethyl, cyano, cyanomethyl, —OR', —NR'$_2$, or —SR', wherein each R' is independently hydrogen, lower alkyl, alkenyl, alkynyl or aryl, provided, however, that neither the —NR'$_2$ nor the —SR' functionality is conjugated with an alkenyl or alkynyl functionality; or B is =C$^{10}$R$^{10a}$— or =N—, provided there is no double bond in the ring between A and B, or between B and C$^9$ when there is a double bond between $N^7$ and $C^8$, and provided that B is not a heteroatom when A is a 1 atom bridging species, $R^2$, $R^4$, and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is S(O)$_2$NHR', R' is not alkenyl or alkynyl;

—C(O)R'', wherein R'' is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''$_2$, wherein each R''' is independently as defined above, or each R''' and the N to which they are attached can cooperate to form a 4-, 5-, 6- or 7-membered ring; provided, however, that the —NR'''$_2$ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR''''$_3$, wherein R'''' is selected from alkyl or aryl, $R^5$ is alkynyl or substituted alkynyl having the structure:

—C≡C—R$^{5'}$ wherein R$^{5'}$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkylene, substituted alkylene, arylene, substituted arylene, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is —S(O)$_2$NHR', R' is not alkenyl or alkynyl;

—C(O)R'', wherein R'' is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''$_2$, wherein each R''' is independently as defined above, or each R''' and the N to which they are attached can cooperate to form a 4-, 5-, 6- or 7-membered ring; provided, however, that the —NR'''$_2$ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR''''$_3$, wherein R'''' is selected from alkyl or aryl, $R^7$ is selected from hydrogen, lower alkyl, aryl, substituted aryl, alkylaryl, or substituted alkylaryl, or $R^7$ is absent when there is a double bond between $N^7$ and $C^8$, and $R^9$ and $R^{9a}$ are each independently selected from hydrogen, lower alkyl, hydroxyalkyl, aryl, aryloxyalkyl, fluoro, trifluoromethyl, cyano, cyanomethyl, —OR', —NR'$_2$, or —SR', wherein each R' is as defined above, provided, however, that neither the —NR'$_2$ nor the —SR' functionality is conjugated with an alkenyl or alkynyl functionality, said method comprising (a) contacting acyl pyridine precursor of Formula II with lactam of Formula III in the presence of a strong base, to produce pyridoyllactam of Formula IV, wherein II is:

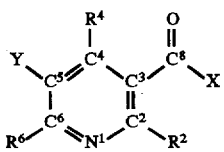

II wherein Y is selected from bromine, iodine or trifluoromethylsulfonyloxy, and III is:

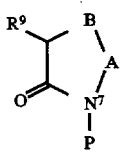

III and wherein IV is:

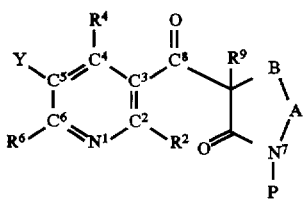

(b) rearranging IV into cyclic imine V:

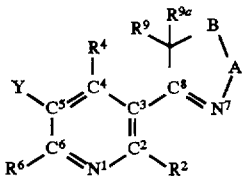

(c) reducing cyclic imine V to produce cyclic amine VI:

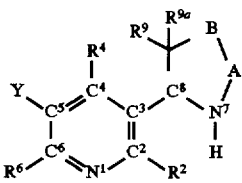

(d) alkylating VI to produce I,
(e) contacting compound I with an acetylenic compound in the presence of a suitable catalyst under conditions suitable to produce a 5-alkynyl derivative of compound I, and thereafter, optionally
(f) contacting the product of step (e) under conditions suitable to remove any protecting group(s) present on the alkynyl moiety or the core of compound I.

18. A method according to claim 17 further comprising:
(g) contacting the product of step (e) or step (f) with an acid capable of forming an optically pure acid addition salt with an enantiomeric mixture of said 5-alkynyl derivative of compound VI or compound I.

19. A method according to claim 18 further comprising separating the optically pure acid addition salt of said 5-alkynyl derivative of compound VI or compound I from the non-crystallized enantiomer of the 5-alkynyl derivative of compound VI or compound I.

20. A method according to claim 17 further comprising:
(g) converting the product of step (e) or step (f) into a diastereomeric derivative of racemic amines.

21. A method comprising separating the diastereomeric derivatives produced by claim 20.

22. A method for the preparation of compounds having the structure I:

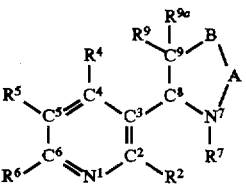

wherein
A is a 1, 2 or 3 atom bridging species which forms part of a saturated or monounsaturated 5-, 6- or 7-membered ring including $N^7$, $C^8$, $C^9$ and B, B is selected from —O—, —S—, —$NR^{10}$—, wherein $R^{10}$ is selected from hydrogen, lower alkyl, aryl, substituted aryl, alkylaryl, substituted alkylaryl, arylalkyl, substituted arylalkyl; —$C^{10}HR^{10a}$—, wherein $R^{10a}$ is selected from hydrogen, lower alkyl, hydroxyalkyl, aryl, aryloxyalkyl, fluoro, trifluoromethyl, cyano, cyanomethyl, —OR', —$NR'_2$, or —SR', wherein each R' is independently hydrogen, lower alkyl, alkenyl, alkynyl or aryl, provided, however, that neither the —$NR'_2$ nor the —SR' functionality is conjugated with an alkenyl or alkynyl functionality; or B is =$C^{10}R^{10a}$— or =N—, provided there is no double bond in the ring between A and B, or between B and $C^9$ when there is a double bond between $N^7$ and $C^8$, and provided that B is not a heteroatom when A is a 1 atom bridging species, $R^2$, $R^4$, and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is S(O)$_2$NHR', R' is not alkenyl or alkynyl;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR''', wherein R''' is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR''' functionality is not conjugated with an alkenyl or alkynyl functionality;

—NR'''$_2$, wherein each R''' is independently as defined above, or each R''' and the N to which they are attached can cooperate to form a 4-, 5-, 6- or 7-membered ring; provided, however, that the —NR'''$_2$ functionality is not conjugated with an alkenyl or alkynyl functionality;

—SR'''', wherein R'''' is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR'''' functionality is not conjugated with an alkenyl or alkynyl functionality; or —SiR'''''$_3$, wherein R''''' is selected from alkyl or aryl, $R^5$ is alkynyl or substituted alkynyl having the structure:

wherein $R^{5'}$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkylene, substituted alkylene, arylene, substituted arylene, heterocyclic, substituted heterocyclic, trifluoromethyl, halogen, cyano, nitro;

—S(O)R', —S(O)$_2$R' or —S(O)$_2$NHR', wherein each R' is as defined above, provided, however, that when $R^2$, $R^4$, $R^5$ or $R^6$ is —S(O)R', R' is not hydrogen, alkenyl or alkynyl, and provided that when $R^2$, $R^4$, $R^5$ or $R^6$ is —S(O)$_2$NHR', R' is not alkenyl or alkynyl;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, provided, however, that the carbonyl functionality is not conjugated with an alkenyl or alkynyl functionality;

—OR'", wherein R'" is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heterocyclic, substituted heterocyclic, acyl, trifluoromethyl, alkylsulfonyl or arylsulfonyl, provided, however, that the —OR'" functionality is not conjugated with an alkenyl or alkynyl functionality;

—NR'"$_2$, wherein each R'" is independently as defined above, or each R'" and the N to which they are attached can cooperate to form a 4-, 5-, 6- or 7-membered ring; provided, however, that the —NR'"$_2$ functionality is not conjugated with an alkenyl or alkynyl functionality;

—SR"", wherein R"" is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic or trifluoromethyl, provided, however, that the —SR"" functionality is not conjugated with an alkenyl or alkynyl functionality; or —SiR""'$_3$, wherein R""' is selected from alkyl or aryl, $R^7$ is selected from hydrogen, lower alkyl, aryl, substituted aryl, alkylaryl, or substituted alkylaryl, or $R^7$ is absent when there is a double bond between $N^7$ and $C^8$, and $R^9$ and $R^{9a}$ are each independently selected from hydrogen, lower alkyl, hydroxyalkyl, aryl, aryloxyalkyl, fluoro, trifluoromethyl, cyano, cyanomethyl, —OR', —NR'$_2$, or —SR', wherein each R' is as defined above, provided, however, that neither the —NR'$_2$ nor the —SR' functionality is conjugated with an alkenyl or alkynyl functionality, said method comprising (a) contacting a compound having the structure:

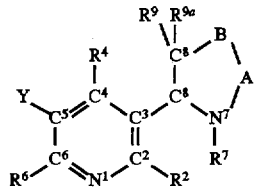

wherein Y is selected from bromine, iodine or trifluoromethylsulfonyloxy, with an acetylenic compound in the presence of a suitable catalyst under conditions suitable to produce a 5-alkynyl derivative thereof, and thereafter, optionally (b) contacting the product of step (a) under conditions suitable to remove any protecting group(s) present on the alkynyl moiety or the core of said compound.

23. A method according to claim 22 further comprising:
(c) contacting the product of step (a) or step (b) with an acid capable of forming an optically pure acid addition salt with an enantiomeric mixture of said 5-alkynyl derivative.

24. A method according to claim 23 further comprising separating the optically pure acid addition salt of said 5-alkynyl derivative from the non-crystallized enantiomer of said 5-alkynyl derivative.

25. A method according to claim 22 further comprising:
(c) converting the product of step (a) or step (b) into a diastereomeric derivative of racemic amines.

26. A method comprising separating the diastereomeric derivatives produced by claim 25.

27. A method according to claim 1 wherein A, B, $R^2$, $R^4$, $R^5$, $R^6$, $R^7$, $R^9$ and $R^{9a}$ of said compound are defined as follows:

A=—CH$_2$—,
B=—CH$_2$—,
$R^2$=hydrogen,
$R^4$=hydrogen,
$R^5$=ethynyl,
$R^6$=hydrogen,
$R^7$=methyl,
$R^9$=hydrogen, and
$R^{9a}$=hydrogen.

* * * * *